US010471086B2

(12) United States Patent
Merali et al.

(10) Patent No.: US 10,471,086 B2
(45) Date of Patent: Nov. 12, 2019

(54) TREATMENT OF CHRONIC OBSTRUCTIVE PULMONARY DISEASE (COPD)

(71) Applicant: TEMPLE UNIVERSITY—OF THE COMMONWEALTH SYSTEM OF HIGHER EDUCATION, Philadelphia, PA (US)

(72) Inventors: Salim Merali, Bryn Mawr, PA (US); Steven G. Kelsen, Rydal, PA (US); Carlos A. Barrero, Philadelphia, PA (US)

(73) Assignee: Temple University—Of The Commonwealth System Of Higher Education, Philadelphia, PA (US)

(*) Notice: Subject to any disclaimer, the term of this patent is extended or adjusted under 35 U.S.C. 154(b) by 0 days.

(21) Appl. No.: 15/081,073

(22) Filed: Mar. 25, 2016

(65) Prior Publication Data
US 2016/0213700 A1 Jul. 28, 2016

Related U.S. Application Data

(63) Continuation of application No. 14/003,120, filed as application No. PCT/US2012/027998 on Mar. 7, 2012, now abandoned.

(60) Provisional application No. 61/449,879, filed on Mar. 7, 2011.

(51) Int. Cl.
G01N 33/53 (2006.01)
A61K 31/7072 (2006.01)
G01N 33/68 (2006.01)
A61K 31/365 (2006.01)

(52) U.S. Cl.
CPC ........ A61K 31/7072 (2013.01); A61K 31/365 (2013.01); G01N 33/6893 (2013.01); G01N 2800/122 (2013.01); G01N 2800/50 (2013.01); G01N 2800/56 (2013.01); G01N 2800/60 (2013.01)

(58) Field of Classification Search
CPC ............. A61K 31/7072; A61K 31/365; G01N 33/6893; G01N 2800/60; G01N 2800/50; G01N 2800/122; G01N 2800/56
See application file for complete search history.

(56) References Cited

U.S. PATENT DOCUMENTS

| 7,144,710 | B2 | 12/2006 | Guyre et al. | |
|---|---|---|---|---|
| 2008/0227117 | A1 | 9/2008 | Fehniger et al. | |
| 2009/0233300 | A1 | 9/2009 | Saavedra et al. | |
| 2010/0022495 | A1* | 1/2010 | Hotamisligil | A61K 31/397 514/182 |
| 2010/0119474 | A1 | 5/2010 | Crystal et al. | |
| 2010/0255486 | A1 | 10/2010 | Showe et al. | |
| 2010/0285477 | A1 | 11/2010 | Kouznetsov et al. | |
| 2013/0143752 | A1 | 6/2013 | Edmiston et al. | |

FOREIGN PATENT DOCUMENTS

| WO | 2007/084485 A2 | 7/2007 |
|---|---|---|
| WO | 2008/109773 A2 | 9/2008 |
| WO | 2009/114292 A1 | 9/2009 |

OTHER PUBLICATIONS

Delpino et al (Bioscience Reports, vol. 22, Nos. 3 and 4, Jun. and Aug. 2002).*
Lee et al. (TRENDS in Biochemical Sciences vol. 26 No. 8 Aug. 2001).*
Shamaei-Tous, (PLoS ONE 2007; 2(11): e1198.*
Laverriere ey al, Molecular Human Reproduction, vol. 15, No. 9 pp. 569-574, 2009.*
Barrero et al., (2010) "Proteomics Analysis Of Lung Nuclear Proteins In Chronic Obstructive Pulmonary Disease", Meeting Abstract A3830, American Thoracic Society 2010 International Conference, May 14-19, 2010, New Orleans; Published online: 10.1164/ajrccm-conference.2010.181.1_MeetingAbstracts.A3830A3830.
Bon et al., (2009) "The Influence of Radiographic Phenotype and Smoking Status on Peripheral Blood Biomarker Patterns in Chronic Obstructive Pulmonary Disease," PLoS ONE 4(8):e6865.
Chen et al., (2010) "Proteomics-Based Biomarkers in Chronic Obstructive Pulmonary Disease," J Proteome Res. 9(6):2798-2808.
Dahl et al., (2009) "Markers of Early Disease and Prognosis in COPD," International Journal of COPD 4:157-167.
Devanarayan et al., (2010) "Identification of Distinct Plasma Biomarker Signatures in Patients with Rapid and Slow Declining Forms of COPD," COPD: Journal of Chronic Obstructive Pulmonay Disease 7:51-58.
De Oca et al., (2005) "Skeletal muscle inflammation and nitric oxide in patients with COPD," Eur Respir J. 26(3):390-397.
Felgentreff et al., (2006) "The antimicrobial peptide cathelicidin interacts with airway mucus," Peptides 27: 3100-3106.
Garcia-Rio et al., (2010) "Systemic inflammation in chronic obstructive pulmonary disease: a population-based study," Respir Res. 11:63 doi:10.1186/1465-9921-11-63.
Hurst et al., (2006), "Use of Plasma Biomarkers at Exacerbation of Chronic Obstructive Pulmonary Disease," Am J Respir and Crit Care Med. 174 (8):867-874. doi: 10.1164/rccm.200604-506OC.

(Continued)

Primary Examiner — Julie Wu
Assistant Examiner — Carmencita M Belei
(74) Attorney, Agent, or Firm — Drinker Biddle & Reath LLP

(57) ABSTRACT

The methods described herein are based on the discovery that the plasma level of a panel of specific proteins differs between two subject populations: 1) subjects at risk for chronic obstructive pulmonary disease ("COPD") but not manifesting clinical symptoms of COPD; and 2) subjects having very severe COPD. The difference in plasma levels is statistically significant for each protein. The identification of these proteins thus facilitates susceptibility detection, early disease detection, disease severity assessment, disease progression monitoring, and therapy efficacy monitoring.

10 Claims, 11 Drawing Sheets
Specification includes a Sequence Listing.

(56) References Cited

OTHER PUBLICATIONS

Kelsen et al., (2008) "Cigarette Smoke Induces an Unfolded Protein Response in the Human Lung," Am J Respir Cell Mol Biol. 38:541-550.

Lau et al., (2009) "Biomarkers of Lung-Related Diseases: Current Knowledge by Proteomic Approaches," J. Cell. Physiol. 221:535-543.

Merali et al, (2010) "Plasma Markers in Chronic Obstructive Pulmonary Disease (COPD)" Poster, presented Sep. 22, 2010 at Human Proteome World Congress, Sydney Australia.

Merali et al, (2010) "Plasma Markers in Chronic Obstructive Pulmonary Disease" HUPO201 Poster Abstract Book, for Human Proteome World Congress meeting held Sep. 19-23, 2010, in Sydney Australia, Poster abstract PO168, p. 378.

Pinto-Plata et al., (2005) "C-reactive protein in patients with COPD, control smokers and non-smokers," Thorax 61:23-28. doi: 10.1136/thx.2005.042200.

Rana et al., (2010) "Proteomic biomarkers in plasma that differentiate rapid and slow decline in lung function in adult cigarette smokers with chronic obstructive pulmonary disease (COPD)," Anal Bioanal Chem. (2010) 397(5):1809-1819. Epub May 5, 2010.

Tagawa et al., (2008) "Induction of apoptosis by cigarette smoke via ROS-dependent endoplasmic reticulum stress and CCAAT/enhancer-binding protein-homologous protein (CHOP),",Free Radical Biology and Medicine 45:50-59.

International Search Report and Written Opinion dated Aug. 23, 2013, for PCT/US2010/27998, filed Mar. 7, 2012.

Jiang et al., 2009, "Glucose-regulated protein 78 antagonizes cisplatin and adriamycin in human melanoma cells," *Carcinogenesis* 30: 197-204.

Kim et al., 2005, "Valproate protects cells from ER stress-induced lipid accumulation and apoptosis by inhibiting glycogen synthase kinase-3," *J Cell Sci.* 118(Pt 1):89-99. Epub Dec. 7, 2004.

Mandic et al., 2003, "Cisplatin induces endoplasmic reticulum stress and nucleus-independent apoptotic signaling," *J Biol Chem.* 278: 9100-9106.

Nawrocki et al., 2005, "Bortezomib inhibits PKR-like endoplasmic reticulum (ER) kinase and induces apoptosis via ER stress in human pancreatic cancer cells," *Cancer Res* 65(24):11510-11519.

Sugawara et al., 1993, "Suppression of stress protein GRP78 induction in tumor B/C10ME eliminates resistance to cell mediated cytotoxicity," *Cancer Res.* 53: 6001-6005.

Wang et al., 2007, "Different induction of GRP78 and CHOP as a predictor of sensitivity to proteasome inhibitors in thyroid cancer cells," *Endocrinology* 148(7):3258-3270.

\* cited by examiner

FIGURE 1A

| Count | Gold# | Post FEV1% | Post FVC% | Post FEV1/FVC | Height (cm) | Weight (kg) | BMI | Pack Years | Quit Age | Age | Sex | Ethnicity | Quit Duration |
|---|---|---|---|---|---|---|---|---|---|---|---|---|---|
| 1 | 0 | 89 | 106 | 0.71 | 160 | 75 | 29.3 | 54 | 55 | 69 | M | C | 14 |
| 2 | 0 | 83 | 81 | 0.77 | 178.80 | 176.41 | 55.18 | 56 | 52 | 61 | M | C | 9 |
| 3 | 0 | 100 | 110 | 0.77 | 171.3 | 83.8 | 28.56 | 51 | 52 | 65 | M | C | 13 |
| 4 | 0 | 82 | 87 | 0.71 | 181.4 | 82.7 | 27.17 | 68 | 51 | 64 | M | C | 13 |
| 5 | 0 | 105 | 100 | 0.79 | 169.5 | 99 | 34.46 | 61 | 46 | 62 | M | C | 16 |
| 6 | 0 | 89 | 91 | 0.75 | 158.6 | 122.5 | 49.7 | 63 | 45 | 65 | M | C | 20 |
| 7 | 0 | 82 | 93 | 0.76 | 163 | 64.8 | 24.31 | 51 | 51 | 63 | M | C | 12 |
| 8 | 0 | 102 | 101 | 0.75 | 168.3 | 77.9 | 27.5 | 74 | 55 | 66 | M | C | 11 |
| 9 | 0 | 97 | 96 | 0.75 | 197.7 | 115.1 | 29.45 | 48 | 52 | 67 | M | C | 15 |
| 10 | 0 | 83 | 80 | 0.78 | 181.4 | 101.7 | 30.91 | 80 | 58 | 63 | M | C | 5 |
|  | Gold 0% |  |  |  |  |  |  |  |  |  |  |  |  |
|  | Mean | 94.1 | 94.5 | 0.754 | 173.0 | 100.9 | 33.7 | 60.5 | 51.7 | 64.4 |  |  | 12.7 |
|  | SEM | 3.1 | 3.2 | 0.008 | 3.6 | 10.1 | 3.2 | 3.4 | 1.2 | 0.8 |  |  | 1.2 |

FIGURE 1B

| Count | Gold# | Post FEV1% | Post FVC% | Post FEV1/FVC | Height (cm) | Weight (kg) | BMI | Pack Years | Quit Age | Age | Sex | Ethnicity | Quit Duration |
|---|---|---|---|---|---|---|---|---|---|---|---|---|---|
| 1 | 4 | 29 | 73 | 0.3 | 162 | 68 | 25.91 | 20 | 58 | 64 | M | C | 6 |
| 2 | 4 | 25 | 47 | 0.39 | 181 | 150.8 | 45.87 | 80 | 63 | 69 | M | C | 6 |
| 3 | 4 | 16 | 50 | 0.26 | 153.9 | 55.3 | 23.75 | 34 | 53 | 67 | M | C | 14 |
| 4 | 4 | 11 | 47 | 0.18 | 162.6 | | | 84 | 50 | 57 | M | C | 7 |
| 5 | 4 | 22 | 73 | 0.23 | 179.9 | 92.6 | 28.61 | 50 | 52 | 63 | M | C | 11 |
| 6 | 4 | 25 | 81 | 0.31 | 167.3 | 71.4 | 25.51 | 70 | 52 | 63 | M | C | 11 |
| 7 | 4 | 10 | 36 | 0.21 | 162.5 | 125.4 | 37.66 | 63 | 53 | 60 | M | C | 7 |
| 8 | 4 | 22 | 51 | 0.31 | 163.00 | 77.00 | 29.00 | 72 | 59 | 63 | M | C | 4 |
| 9 | 3 | 57 | 84 | 0.44 | 178.00 | 94.00 | 29.70 | 58.5 | 55 | 57 | M | C | 2 |
| 10 | 3 | 33 | 66 | 0.37 | 168.00 | 98.00 | 34.70 | 62.5 | 64 | 69 | M | C | 5 |
| 1.1 | Gold 4's | | | | | | | | | | | | |
| | Mean | 23.0 | 65.7 | 0.2991 | 170.0 | 92.3 | 31.1 | 58.9 | 55.9 | 63.1 | | | 7.2 |
| | SEM | 2.8 | 4.0 | 0.026 | 3.0 | 10.0 | 2.4 | 6.0 | 1.5 | 1.4 | | | 1.1 |

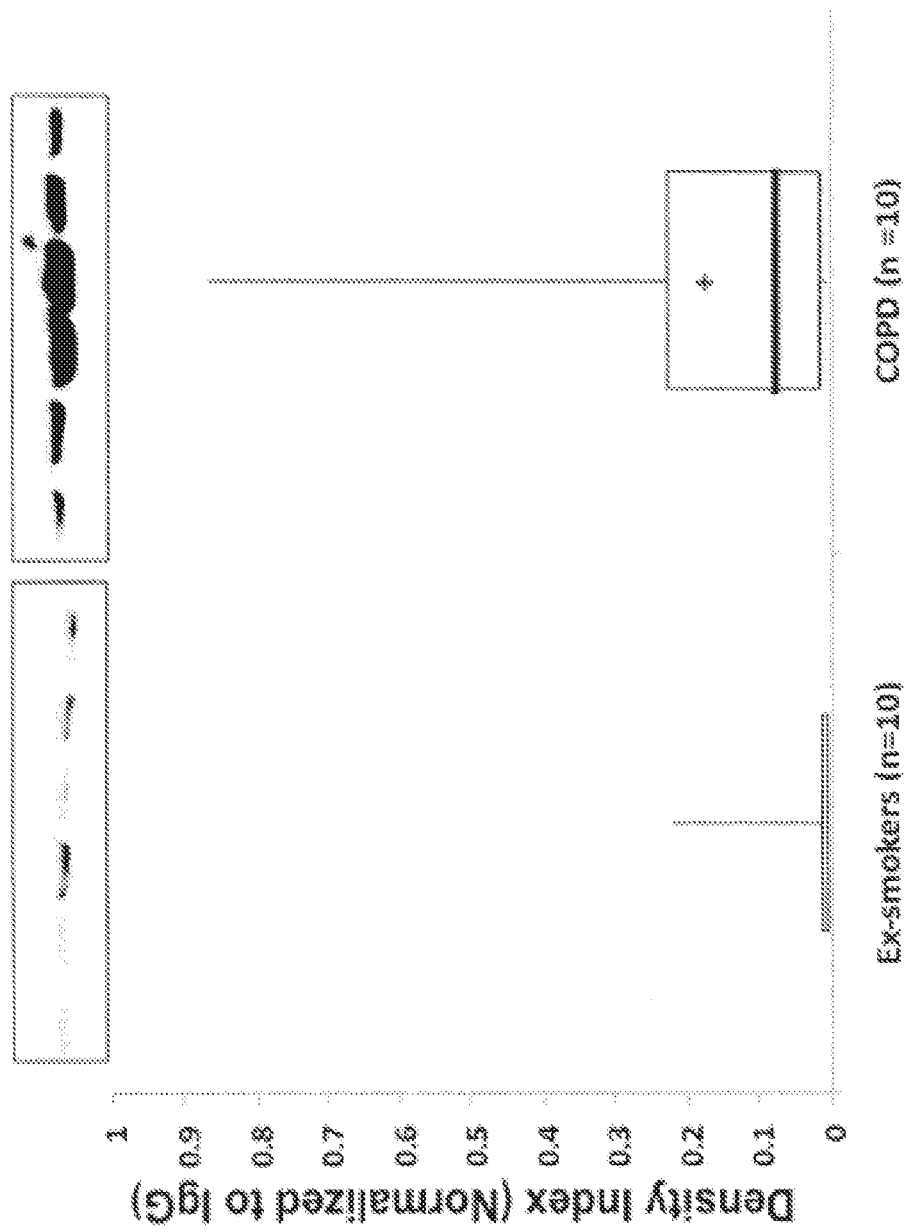

FIGURES 6A and 6B
6A
GOLD-0
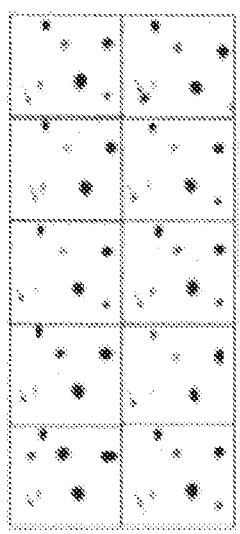
GOLD-IV
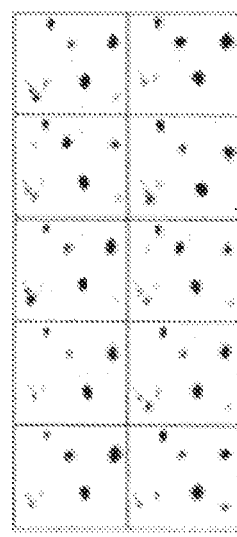
6B
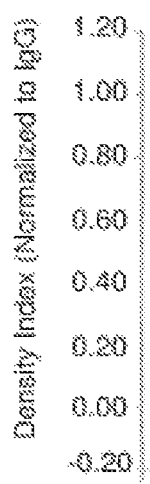
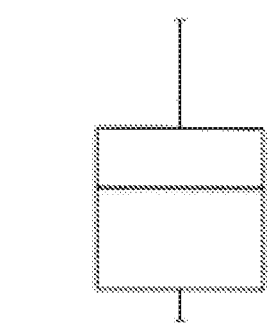

FIGURES 8A-8D
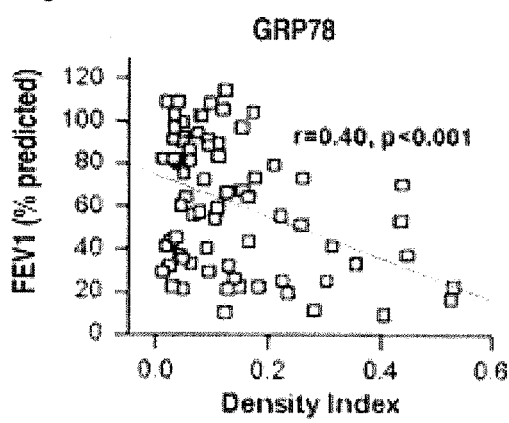
Fig. 8A
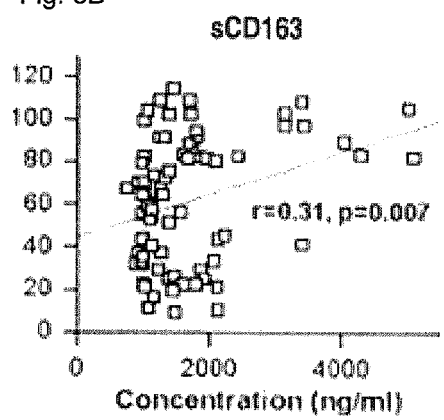
Fig. 8B
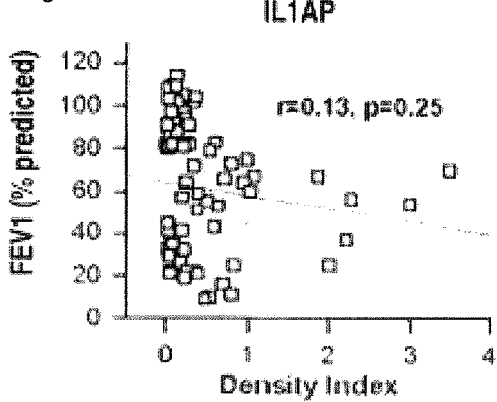
Fig. 8C
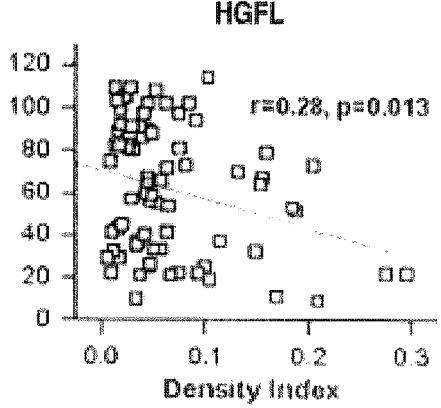
Fig. 8D

SEQUENCE LISTING

<160> NUMBER OF SEQ ID NOS: 32

<210> SEQ ID NO 1
<211> LENGTH: 780
<212> TYPE: PRT
<213> ORGANISM: Homo sapiens

<400> SEQUENCE: 1

Met Thr Glu Ser Ala Ser Ser Thr Ser Gly Gln Glu Phe Asp Val Phe
1               5                   10                  15

Ser Val Met Asp Trp Lys Asp Gly Val Gly Thr Leu Pro Gly Ser Asp
            20                  25                  30

Leu Lys Phe Arg Val Asn Glu Phe Gly Ala Leu Glu Val Ile Thr Asp
        35                  40                  45

Glu Asn Glu Met Glu Asn Val Lys Lys Ala Thr Ala Thr Thr Thr Trp
    50                  55                  60

Met Val Pro Thr Ala Gln Glu Ala Pro Thr Ser Pro Pro Ser Ser Arg
65                  70                  75                  80

Pro Val Phe Pro Pro Ala Tyr Trp Thr Ser Pro Pro Gly Cys Pro Thr
                85                  90                  95

Val Phe Ser Glu Lys Thr Gly Met Pro Phe Arg Leu Lys Asp Pro Val
            100                 105                 110

Lys Val Glu Gly Leu Gln Phe Cys Glu Asn Cys Gln Tyr Gly Asn
        115                 120                 125

Val Asp Glu Cys Leu Ser Gly Gly Asn Tyr Cys Ser Gln Asn Cys Ala
130                 135                 140

Arg His Ile Lys Asp Lys Asp Gln Lys Glu Glu Arg Asp Val Glu Glu
145                 150                 155                 160

Asp Asn Glu Glu Glu Asp Pro Lys Cys Ser Arg Lys Lys Pro Lys
                165                 170                 175

Leu Ser Leu Lys Ala Asp Thr Lys Glu Asp Gly Glu Glu Arg Asp Asp
            180                 185                 190

Glu Met Glu Asn Lys Gln Asp Val Arg Ile Leu Arg Gly Ser Gln Arg
        195                 200                 205

Ala Arg Arg Lys Arg Arg Gly Asp Ser Ala Val Leu Lys Gln Gly Leu
    210                 215                 220

Pro Pro Lys Gly Lys Lys Ala Trp Cys Trp Ala Ser Tyr Leu Glu Glu
225                 230                 235                 240

Glu Lys Ala Val Ala Val Pro Ala Lys Leu Phe Lys Glu His Gln Ser
                245                 250                 255

Phe Pro Tyr Asn Lys Asn Gly Phe Lys Val Gly Met Lys Leu Glu Gly
            260                 265                 270

Val Asp Pro Glu His Gln Ser Val Tyr Cys Val Leu Thr Val Ala Glu
        275                 280                 285

Val Cys Gly Tyr Arg Ile Lys Leu His Phe Asp Gly Tyr Ser Asp Cys
    290                 295                 300

Tyr Asp Phe Trp Val Asn Ala Asp Ala Leu Asp Ile His Pro Val Gly
305                 310                 315                 320

Trp Cys Glu Lys Thr Gly His Lys Leu His Pro Pro Lys Gly Tyr Lys
                325                 330                 335

Glu Glu Glu Phe Asn Trp Gln Thr Tyr Leu Lys Thr Cys Lys Ala Gln
            340                 345                 350

Ala Ala Pro Lys Ser Leu Phe Glu Asn Gln Asn Ile Thr Val Ile Pro
        355                 360                 365

```
Ser Gly Phe Arg Val Gly Met Lys Leu Glu Ala Val Asp Lys Lys Asn
    370                 375                 380

Pro Ser Phe Ile Cys Val Ala Thr Val Thr Asp Met Val Asp Asn Arg
385                 390                 395                 400

Phe Leu Val His Phe Asp Asn Trp Asp Glu Ser Tyr Asp Tyr Trp Cys
            405                 410                 415

Glu Ala Ser Ser Pro His Ile His Pro Val Gly Trp Cys Lys Glu His
                420                 425                 430

Arg Arg Thr Leu Ile Thr Pro Pro Gly Tyr Pro Asn Val Lys His Phe
            435                 440                 445

Ser Trp Asp Lys Tyr Leu Glu Glu Thr Asn Ser Leu Pro Ala Pro Ala
    450                 455                 460

Arg Ala Phe Lys Val Lys Pro Pro His Gly Phe Gln Lys Lys Met Lys
465                 470                 475                 480

Leu Glu Val Val Asp Lys Arg Asn Pro Met Phe Ile Arg Val Ala Thr
                485                 490                 495

Val Ala Asp Thr Asp Asp His Arg Val Lys Val His Phe Asp Gly Trp
            500                 505                 510

Asn Asn Cys Tyr Asp Tyr Trp Ile Asp Ala Asp Ser Pro Asp Ile His
            515                 520                 525

Pro Val Gly Trp Cys Ser Lys Thr Gly His Pro Leu Gln Pro Pro Leu
530                 535                 540

Ser Pro Leu Glu Leu Met Glu Ala Ser Glu His Gly Gly Cys Ser Thr
545                 550                 555                 560

Pro Gly Cys Lys Gly Ile Gly His Phe Lys Arg Ala Arg His Leu Gly
                565                 570                 575

Pro His Ser Ala Ala Asn Cys Pro Tyr Ser Glu Ile Asn Leu Asn Lys
            580                 585                 590

Asp Arg Ile Phe Pro Asp Arg Leu Ser Gly Glu Met Pro Pro Ala Ser
            595                 600                 605

Pro Ser Phe Pro Arg Asn Lys Arg Thr Asp Ala Asn Glu Ser Ser Ser
            610                 615                 620

Ser Pro Glu Ile Arg Asp Gln His Ala Asp Asp Val Lys Glu Asp Phe
625                 630                 635                 640

Glu Glu Arg Thr Glu Ser Glu Met Arg Thr Ser His Glu Ala Arg Gly
                645                 650                 655

Ala Arg Glu Glu Pro Thr Val Gln Gln Ala Gln Arg Arg Ser Ala Val
                660                 665                 670

Phe Leu Ser Phe Lys Ser Pro Ile Pro Cys Leu Pro Leu Arg Trp Glu
            675                 680                 685

Gln Gln Ser Lys Leu Leu Pro Thr Val Ala Gly Ile Pro Ala Ser Lys
            690                 695                 700

Val Ser Lys Trp Ser Thr Asp Glu Val Ser Glu Phe Ile Gln Ser Leu
705                 710                 715                 720

Pro Gly Cys Glu Glu His Gly Lys Val Phe Lys Asp Glu Gln Ile Asp
                725                 730                 735

Gly Glu Ala Phe Leu Leu Met Thr Gln Thr Asp Ile Val Lys Ile Met
            740                 745                 750

Ser Ile Lys Leu Gly Pro Ala Leu Lys Ile Phe Asn Ser Ile Leu Met
            755                 760                 765

Phe Lys Ala Ala Glu Lys Asn Ser His Asn Glu Leu
770                 775                 780
```

```
<210> SEQ ID NO 2
<211> LENGTH: 170
<212> TYPE: PRT
<213> ORGANISM: Homo sapiens

<400> SEQUENCE: 2

Met Lys Thr Gln Arg Asp Gly His Ser Leu Gly Arg Trp Ser Leu Val
 1               5                  10                  15

Leu Leu Leu Leu Gly Leu Val Met Pro Leu Ala Ile Ile Ala Gln Val
            20                  25                  30

Leu Ser Tyr Lys Glu Ala Val Leu Arg Ala Ile Asp Gly Ile Asn Gln
        35                  40                  45

Arg Ser Ser Asp Ala Asn Leu Tyr Arg Leu Leu Asp Leu Asp Pro Arg
    50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Phe Arg Lys Ser Lys Glu
    130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170

<210> SEQ ID NO 3
<211> LENGTH: 1018
<212> TYPE: PRT
<213> ORGANISM: Homo sapiens

<400> SEQUENCE: 3

Met Lys Met Trp Leu Leu Val Ser His Leu Val Ile Ile Ser Ile Thr
 1               5                  10                  15

Thr Cys Leu Ala Glu Phe Thr Trp Tyr Arg Arg Tyr Gly His Gly Val
            20                  25                  30

Ser Glu Glu Asp Lys Gly Phe Gly Pro Ile Phe Glu Glu Gln Pro Ile
        35                  40                  45

Asn Thr Ile Tyr Pro Glu Glu Ser Leu Glu Gly Lys Val Ser Leu Asn
    50                  55                  60

Cys Arg Ala Arg Ala Ser Pro Phe Pro Val Tyr Lys Trp Arg Met Asn
65                  70                  75                  80

Asn Gly Asp Val Asp Leu Thr Ser Asp Arg Tyr Ser Met Val Gly Gly
                85                  90                  95

Asn Leu Val Ile Asn Asn Pro Asp Lys Gln Lys Asp Ala Gly Ile Tyr
            100                 105                 110

Tyr Cys Leu Ala Ser Asn Asn Tyr Gly Met Val Arg Ser Thr Glu Ala
        115                 120                 125

Thr Leu Ser Phe Gly Tyr Leu Asp Pro Phe Pro Pro Glu Glu Arg Pro
    130                 135                 140

Glu Val Arg Val Lys Glu Gly Lys Gly Met Val Leu Leu Cys Asp Pro
145                 150                 155                 160
```

```
Pro Tyr His Phe Pro Asp Asp Leu Ser Tyr Arg Trp Leu Leu Asn Glu
            165                 170                 175
Phe Pro Val Phe Ile Thr Met Asp Lys Arg Arg Phe Val Ser Gln Thr
            180                 185                 190
Asn Gly Asn Leu Tyr Ile Ala Asn Val Glu Ala Ser Asp Lys Gly Asn
            195                 200                 205
Tyr Ser Cys Phe Val Ser Ser Pro Ser Ile Thr Lys Ser Val Phe Ser
            210                 215                 220
Lys Phe Ile Pro Leu Ile Pro Ile Pro Glu Arg Thr Thr Lys Pro Tyr
225                 230                 235                 240
Pro Ala Asp Ile Val Val Gln Phe Lys Asp Val Tyr Ala Leu Met Gly
            245                 250                 255
Gln Asn Val Thr Leu Glu Cys Phe Ala Leu Gly Asn Pro Val Pro Asp
            260                 265                 270
Ile Arg Trp Arg Lys Val Leu Glu Pro Met Pro Ser Thr Ala Glu Ile
            275                 280                 285
Ser Thr Ser Gly Ala Val Leu Lys Ile Phe Asn Ile Gln Leu Glu Asp
            290                 295                 300
Glu Gly Ile Tyr Glu Cys Glu Ala Glu Asn Ile Arg Gly Lys Asp Lys
305                 310                 315                 320
His Gln Ala Arg Ile Tyr Val Gln Ala Phe Pro Glu Trp Val Glu His
            325                 330                 335
Ile Asn Asp Thr Glu Val Asp Ile Gly Ser Asp Leu Tyr Trp Pro Cys
            340                 345                 350
Val Ala Thr Gly Lys Pro Ile Pro Thr Ile Arg Trp Leu Lys Asn Gly
            355                 360                 365
Tyr Ala Tyr His Lys Gly Glu Leu Arg Leu Tyr Asp Val Thr Phe Glu
            370                 375                 380
Asn Ala Gly Met Tyr Gln Cys Ile Ala Glu Asn Thr Tyr Gly Ala Ile
385                 390                 395                 400
Tyr Ala Asn Ala Glu Leu Lys Ile Leu Ala Leu Ala Pro Thr Phe Glu
            405                 410                 415
Met Asn Pro Met Lys Lys Lys Ile Leu Ala Ala Lys Gly Gly Arg Val
            420                 425                 430
Ile Ile Glu Cys Lys Pro Lys Ala Ala Pro Lys Pro Lys Phe Ser Trp
            435                 440                 445
Ser Lys Gly Thr Glu Trp Leu Val Asn Ser Ser Arg Ile Leu Ile Trp
            450                 455                 460
Glu Asp Gly Ser Leu Glu Ile Asn Asn Ile Thr Arg Asn Asp Gly Gly
465                 470                 475                 480
Ile Tyr Thr Cys Phe Ala Glu Asn Asn Arg Gly Lys Ala Asn Ser Thr
            485                 490                 495
Gly Thr Leu Val Ile Thr Asp Pro Thr Arg Ile Ile Leu Ala Pro Ile
            500                 505                 510
Asn Ala Asp Ile Thr Val Gly Glu Asn Ala Thr Met Gln Cys Ala Ala
            515                 520                 525
Ser Phe Asp Pro Ala Leu Asp Leu Thr Phe Val Trp Ser Phe Asn Gly
            530                 535                 540
Tyr Val Ile Asp Phe Asn Lys Glu Asn Ile His Tyr Gln Arg Asn Phe
545                 550                 555                 560
Met Leu Asp Ser Asn Gly Glu Leu Leu Ile Arg Asn Ala Gln Leu Lys
            565                 570                 575
```

His Ala Gly Arg Tyr Thr Cys Thr Ala Gln Thr Ile Val Asp Asn Ser
            580                 585                 590

Ser Ala Ser Ala Asp Leu Val Val Arg Gly Pro Pro Gly Pro Pro Gly
        595                 600                 605

Gly Leu Arg Ile Glu Asp Ile Arg Ala Thr Ser Val Ala Leu Thr Trp
    610                 615                 620

Ser Arg Gly Ser Asp Asn His Ser Pro Ile Ser Lys Tyr Thr Ile Gln
625                 630                 635                 640

Thr Lys Thr Ile Leu Ser Asp Asp Trp Lys Asp Ala Lys Thr Asp Pro
                645                 650                 655

Pro Ile Ile Glu Gly Asn Met Glu Ala Ala Arg Ala Val Asp Leu Ile
            660                 665                 670

Pro Trp Met Glu Tyr Glu Phe Arg Val Val Ala Thr Asn Thr Leu Gly
        675                 680                 685

Arg Gly Glu Pro Ser Ile Pro Ser Asn Arg Ile Lys Thr Asp Gly Ala
    690                 695                 700

Ala Pro Asn Val Ala Pro Ser Asp Val Gly Gly Gly Gly Arg Asn
705                 710                 715                 720

Arg Glu Leu Thr Ile Thr Trp Ala Pro Leu Ser Arg Glu Tyr His Tyr
                725                 730                 735

Gly Asn Asn Phe Gly Tyr Ile Val Ala Phe Lys Pro Phe Asp Gly Glu
            740                 745                 750

Glu Trp Lys Lys Val Thr Val Thr Asn Pro Asp Thr Gly Arg Tyr Val
        755                 760                 765

His Lys Asp Glu Thr Met Ser Pro Ser Thr Ala Phe Gln Val Lys Val
    770                 775                 780

Lys Ala Phe Asn Asn Lys Gly Asp Gly Pro Tyr Ser Leu Val Ala Val
785                 790                 795                 800

Ile Asn Ser Ala Gln Asp Ala Pro Ser Glu Ala Pro Thr Glu Val Gly
                805                 810                 815

Val Lys Val Leu Ser Ser Ser Glu Ile Ser Val His Trp Glu His Val
            820                 825                 830

Leu Glu Lys Ile Val Glu Ser Tyr Gln Ile Arg Tyr Trp Ala Ala His
        835                 840                 845

Asp Lys Glu Glu Ala Ala Asn Arg Val Gln Val Thr Ser Gln Glu Tyr
    850                 855                 860

Ser Ala Arg Leu Glu Asn Leu Leu Pro Asp Thr Gln Tyr Phe Ile Glu
865                 870                 875                 880

Val Gly Ala Cys Asn Ser Ala Gly Cys Gly Pro Pro Ser Asp Met Ile
                885                 890                 895

Glu Ala Phe Thr Lys Lys Ala Pro Pro Ser Gln Pro Pro Arg Ile Ile
            900                 905                 910

Ser Ser Val Arg Ser Gly Ser Arg Tyr Ile Ile Thr Trp Asp His Val
        915                 920                 925

Val Ala Leu Ser Asn Glu Ser Thr Val Thr Gly Tyr Lys Val Leu Tyr
    930                 935                 940

Arg Pro Asp Gly Gln His Asp Gly Lys Leu Tyr Ser Thr His Lys His
945                 950                 955                 960

Ser Ile Glu Val Pro Ile Pro Arg Asp Gly Glu Tyr Val Val Glu Val
                965                 970                 975

Arg Ala His Ser Asp Gly Gly Asp Gly Val Val Ser Gln Val Lys Ile
            980                 985                 990

```
Ser Gly Ala Pro Thr Leu Ser Pro  Ser Leu Leu Gly Leu  Leu Leu Pro
         995              1000              1005

Ala Phe Gly Ile Leu Val Tyr  Leu Glu Phe
   1010             1015

<210> SEQ ID NO 4
<211> LENGTH: 739
<212> TYPE: PRT
<213> ORGANISM: Homo sapiens

<400> SEQUENCE: 4

Met Pro Gly Lys Met Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350
```

```
Ser Pro Leu Ser Gly Lys Val Arg Ser Glu Gly Thr Asn Ser Thr Leu
            355                 360                 365
Thr Leu Ser Pro Val Ser Phe Glu Asn Glu His Ser Tyr Leu Cys Thr
        370                 375                 380
Val Thr Cys Gly His Lys Lys Leu Glu Lys Gly Ile Gln Val Glu Leu
385                 390                 395                 400
Tyr Ser Phe Pro Arg Asp Pro Glu Ile Glu Met Ser Gly Gly Leu Val
                405                 410                 415
Asn Gly Ser Ser Val Thr Val Ser Cys Lys Val Pro Ser Val Tyr Pro
            420                 425                 430
Leu Asp Arg Leu Glu Ile Glu Leu Leu Lys Gly Glu Thr Ile Leu Glu
        435                 440                 445
Asn Ile Glu Phe Leu Glu Asp Thr Asp Met Lys Ser Leu Glu Asn Lys
    450                 455                 460
Ser Leu Glu Met Thr Phe Ile Pro Thr Ile Glu Asp Thr Gly Lys Ala
465                 470                 475                 480
Leu Val Cys Gln Ala Lys Leu His Ile Asp Asp Met Glu Phe Glu Pro
                485                 490                 495
Lys Gln Arg Gln Ser Thr Gln Thr Leu Tyr Val Asn Val Ala Pro Arg
            500                 505                 510
Asp Thr Thr Val Leu Val Ser Pro Ser Ser Ile Leu Glu Glu Gly Ser
        515                 520                 525
Ser Val Asn Met Thr Cys Leu Ser Gln Gly Phe Pro Ala Pro Lys Ile
    530                 535                 540
Leu Trp Ser Arg Gln Leu Pro Asn Gly Glu Leu Gln Pro Leu Ser Glu
545                 550                 555                 560
Asn Ala Thr Leu Thr Leu Ile Ser Thr Lys Met Glu Asp Ser Gly Val
                565                 570                 575
Tyr Leu Cys Glu Gly Ile Asn Gln Ala Gly Arg Ser Arg Lys Glu Val
            580                 585                 590
Glu Leu Ile Ile Gln Val Thr Pro Lys Asp Ile Lys Leu Thr Ala Phe
        595                 600                 605
Pro Ser Glu Ser Val Lys Glu Gly Asp Thr Val Ile Ile Ser Cys Thr
    610                 615                 620
Cys Gly Asn Val Pro Glu Thr Trp Ile Ile Leu Lys Lys Lys Ala Glu
625                 630                 635                 640
Thr Gly Asp Thr Val Leu Lys Ser Ile Asp Gly Ala Tyr Thr Ile Arg
                645                 650                 655
Lys Ala Gln Leu Lys Asp Ala Gly Val Tyr Glu Cys Glu Ser Lys Asn
            660                 665                 670
Lys Val Gly Ser Gln Leu Arg Ser Leu Thr Leu Asp Val Gln Gly Arg
        675                 680                 685
Glu Asn Asn Lys Asp Tyr Phe Ser Pro Glu Leu Leu Val Leu Tyr Phe
    690                 695                 700
Ala Ser Ser Leu Ile Ile Pro Ala Ile Gly Met Ile Ile Tyr Phe Ala
705                 710                 715                 720
Arg Lys Ala Asn Met Lys Gly Ser Tyr Ser Leu Val Glu Ala Gln Lys
                725                 730                 735
Ser Lys Val

<210> SEQ ID NO 5
<211> LENGTH: 570
<212> TYPE: PRT
<213> ORGANISM: Homo sapiens
```

<400> SEQUENCE: 5

```
Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
            35                  40                  45

Leu Phe Glu His Phe Leu Lys Phe Asn Tyr Ser Thr Ala His Ser Ala
        50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Leu Ala Cys Gly Phe Gly Ala Thr Val
        355                 360                 365

Leu Leu Val Val Ile Leu Val Val Tyr His Val Tyr Trp Leu Glu
    370                 375                 380

Met Val Leu Phe Tyr Arg Ala His Phe Gly Thr Asp Glu Thr Ile Leu
385                 390                 395                 400

Asp Gly Lys Glu Tyr Asp Ile Tyr Val Ser Tyr Ala Arg Asn Ala Glu
                405                 410                 415
```

```
Glu Glu Glu Phe Val Leu Leu Thr Leu Arg Gly Val Leu Glu Asn Glu
            420                 425                 430
Phe Gly Tyr Lys Leu Cys Ile Phe Asp Arg Asp Ser Leu Pro Gly Gly
        435                 440                 445
Ile Val Thr Asp Glu Thr Leu Ser Phe Ile Gln Lys Ser Arg Arg Leu
    450                 455                 460
Leu Val Leu Ser Pro Asn Tyr Val Leu Gln Gly Thr Gln Ala Leu
465                 470                 475                 480
Leu Glu Leu Lys Ala Gly Leu Glu Asn Met Ala Ser Arg Gly Asn Ile
                485                 490                 495
Asn Val Ile Leu Val Gln Tyr Lys Ala Val Lys Glu Thr Lys Val Lys
                500                 505                 510
Glu Leu Lys Arg Ala Lys Thr Val Leu Thr Val Ile Lys Trp Lys Gly
            515                 520                 525
Glu Lys Ser Lys Tyr Pro Gln Gly Arg Phe Trp Lys Gln Leu Gln Val
        530                 535                 540
Ala Met Pro Val Lys Lys Ser Pro Arg Arg Ser Ser Ser Asp Glu Gln
545                 550                 555                 560
Gly Leu Ser Tyr Ser Ser Leu Lys Asn Val
                565                 570

<210> SEQ ID NO 6
<211> LENGTH: 110
<212> TYPE: PRT
<213> ORGANISM: Homo sapiens

<400> SEQUENCE: 6

Met Arg Phe Met Thr Leu Leu Phe Leu Thr Ala Leu Ala Gly Ala Leu
1               5                   10                  15
Val Cys Ala Tyr Asp Pro Glu Ala Ala Ser Ala Pro Gly Ser Gly Asn
            20                  25                  30
Pro Cys His Glu Ala Ser Ala Ala Gln Lys Glu Asn Ala Gly Glu Asp
        35                  40                  45
Pro Gly Leu Ala Arg Gln Ala Pro Lys Pro Arg Lys Gln Arg Ser Ser
    50                  55                  60
Leu Leu Glu Lys Gly Leu Asp Gly Ala Lys Lys Ala Val Gly Gly Leu
65                  70                  75                  80
Gly Lys Leu Gly Lys Asp Ala Val Glu Asp Leu Glu Ser Val Gly Lys
                85                  90                  95
Gly Ala Val His Asp Val Lys Asp Val Leu Asp Ser Val Leu
                100                 105                 110

<210> SEQ ID NO 7
<211> LENGTH: 400
<212> TYPE: PRT
<213> ORGANISM: Homo sapiens

<400> SEQUENCE: 7

Met Ala Gly Cys Val Pro Leu Leu Gln Gly Leu Val Leu Val Leu Ala
1               5                   10                  15
Leu His Arg Val Glu Pro Ser Val Phe Leu Pro Ala Ser Lys Ala Asn
            20                  25                  30
Asp Val Leu Val Arg Trp Lys Arg Ala Gly Ser Tyr Leu Leu Glu Glu
        35                  40                  45
Leu Phe Glu Gly Asn Leu Glu Lys Glu Cys Tyr Glu Glu Ile Cys Val
    50                  55                  60
```

-continued

Tyr Glu Glu Ala Arg Glu Val Phe Glu Asn Glu Val Thr Asp Glu
 65                  70                  75                  80

Phe Trp Arg Arg Tyr Lys Gly Gly Ser Pro Cys Ile Ser Gln Pro Cys
                 85                  90                  95

Leu His Asn Gly Ser Cys Gln Asp Ser Ile Trp Gly Tyr Thr Cys Thr
                100                 105                 110

Cys Ser Pro Gly Tyr Glu Gly Ser Asn Cys Glu Leu Ala Lys Asn Glu
            115                 120                 125

Cys His Pro Glu Arg Thr Asp Gly Cys Gln His Phe Cys Leu Pro Gly
        130                 135                 140

Gln Glu Ser Tyr Thr Cys Ser Cys Ala Gln Gly Tyr Arg Leu Gly Glu
145                 150                 155                 160

Asp His Lys Gln Cys Val Pro His Asp Gln Cys Ala Cys Gly Val Leu
                165                 170                 175

Thr Ser Glu Lys Arg Ala Pro Asp Leu Gln Asp Leu Pro Trp Gln Val
            180                 185                 190

Lys Leu Thr Asn Ser Glu Gly Lys Asp Phe Cys Gly Gly Val Ile Ile
        195                 200                 205

Arg Glu Asn Phe Val Leu Thr Thr Ala Lys Cys Ser Leu Leu His Arg
210                 215                 220

Asn Ile Thr Val Lys Thr Tyr Phe Asn Arg Thr Ser Gln Asp Pro Leu
225                 230                 235                 240

Met Ile Lys Ile Thr His Val His Val Met Arg Tyr Asp Ala Asp
                245                 250                 255

Ala Gly Glu Asn Asp Leu Ser Leu Leu Glu Leu Glu Trp Pro Ile Gln
            260                 265                 270

Cys Pro Gly Ala Gly Leu Pro Val Cys Thr Pro Glu Lys Asp Phe Ala
        275                 280                 285

Glu His Leu Leu Ile Pro Arg Thr Arg Gly Leu Leu Ser Gly Trp Ala
290                 295                 300

Arg Asn Gly Thr Asp Leu Gly Asn Ser Leu Thr Thr Arg Pro Val Thr
305                 310                 315                 320

Leu Val Glu Gly Glu Glu Cys Gly Gln Val Leu Asn Val Thr Val Thr
                325                 330                 335

Thr Arg Thr Tyr Cys Glu Arg Ser Ser Val Ala Ala Met His Trp Met
            340                 345                 350

Asp Gly Ser Val Val Thr Arg Glu His Arg Gly Ser Trp Phe Leu Thr
        355                 360                 365

Gly Val Leu Gly Ser Gln Pro Val Gly Gly Gln Ala His Met Val Leu
370                 375                 380

Val Thr Lys Val Ser Arg Tyr Ser Leu Trp Phe Lys Gln Ile Met Asn
385                 390                 395                 400

<210> SEQ ID NO 8
<211> LENGTH: 711
<212> TYPE: PRT
<213> ORGANISM: Homo sapiens

<400> SEQUENCE: 8

Met Gly Trp Leu Pro Leu Leu Leu Leu Leu Thr Gln Cys Leu Gly Val
 1               5                  10                  15

Pro Gly Gln Arg Ser Pro Leu Asn Asp Phe Gln Val Leu Arg Gly Thr
                20                  25                  30

Glu Leu Gln His Leu Leu His Ala Val Val Pro Gly Pro Trp Gln Glu
            35                  40                  45

```
Asp Val Ala Asp Ala Glu Glu Cys Ala Gly Arg Cys Gly Pro Leu Met
    50                  55                  60

Asp Cys Arg Ala Phe His Tyr Asn Val Ser Ser His Gly Cys Gln Leu
65                  70                  75                  80

Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
            100                 105                 110

Asn Asn Gly Val Gly Tyr Arg Gly Thr Met Ala Thr Thr Val Gly Gly
            115                 120                 125

Leu Pro Cys Gln Ala Trp Ser His Lys Phe Pro Asn Asp His Lys Tyr
    130                 135                 140

Thr Pro Thr Leu Arg Asn Gly Leu Glu Glu Asn Phe Cys Arg Asn Pro
145                 150                 155                 160

Asp Gly Asp Pro Gly Gly Pro Trp Cys Tyr Thr Asp Pro Ala Val
                165                 170                 175

Arg Phe Gln Ser Cys Gly Ile Lys Ser Cys Arg Glu Ala Ala Cys Val
            180                 185                 190

Trp Cys Asn Gly Glu Glu Tyr Arg Gly Ala Val Asp Arg Thr Glu Ser
        195                 200                 205

Gly Arg Glu Cys Gln Arg Trp Asp Leu Gln His Pro His Gln His Pro
210                 215                 220

Phe Glu Pro Gly Lys Phe Leu Asp Gln Gly Leu Asp Asp Asn Tyr Cys
225                 230                 235                 240

Arg Asn Pro Asp Gly Ser Glu Arg Pro Trp Cys Tyr Thr Thr Asp Pro
            245                 250                 255

Gln Ile Glu Arg Glu Phe Cys Asp Leu Pro Arg Cys Gly Ser Glu Ala
            260                 265                 270

Gln Pro Arg Gln Glu Ala Thr Thr Val Ser Cys Phe Arg Gly Lys Gly
        275                 280                 285

Glu Gly Tyr Arg Gly Thr Ala Asn Thr Thr Thr Ala Gly Val Pro Cys
    290                 295                 300

Gln Arg Trp Asp Ala Gln Ile Pro His Gln His Arg Phe Thr Pro Glu
305                 310                 315                 320

Lys Tyr Ala Cys Lys Asp Leu Arg Glu Asn Phe Cys Arg Asn Pro Asp
            325                 330                 335

Gly Ser Glu Ala Pro Trp Cys Phe Thr Leu Arg Pro Gly Met Arg Ala
        340                 345                 350

Ala Phe Cys Tyr Gln Ile Arg Arg Cys Thr Asp Asp Val Arg Pro Gln
    355                 360                 365

Asp Cys Tyr His Gly Ala Gly Glu Gln Tyr Arg Gly Thr Val Ser Lys
    370                 375                 380

Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
                405                 410                 415

Asn Phe Cys Arg Asn Pro Asp Gly Asp Ser His Gly Pro Trp Cys Tyr
            420                 425                 430

Thr Met Asp Pro Arg Thr Pro Phe Asp Tyr Cys Ala Leu Arg Arg Cys
        435                 440                 445

Ala Asp Asp Gln Pro Pro Ser Ile Leu Asp Pro Pro Asp Gln Val Gln
450                 455                 460
```

Phe Glu Lys Cys Gly Lys Arg Val Asp Arg Leu Asp Gln Arg Arg Ser
465                 470                 475                 480

Lys Leu Arg Val Val Gly Gly His Pro Gly Asn Ser Pro Trp Thr Val
            485                 490                 495

Ser Leu Arg Asn Arg Gln Gly Gln His Phe Cys Gly Gly Ser Leu Val
        500                 505                 510

Lys Glu Gln Trp Ile Leu Thr Ala Arg Gln Cys Phe Ser Ser Cys His
    515                 520                 525

Met Pro Leu Thr Gly Tyr Glu Val Trp Leu Gly Thr Leu Phe Gln Asn
530                 535                 540

Pro Gln His Gly Glu Pro Ser Leu Gln Arg Val Pro Val Ala Lys Met
545                 550                 555                 560

Val Cys Gly Pro Ser Gly Ser Gln Leu Val Leu Leu Lys Leu Glu Arg
                565                 570                 575

Ser Val Thr Leu Asn Gln Arg Val Ala Leu Ile Cys Leu Pro Pro Glu
            580                 585                 590

Trp Tyr Val Val Pro Pro Gly Thr Lys Cys Glu Ile Ala Gly Trp Gly
        595                 600                 605

Glu Thr Lys Gly Thr Gly Asn Asp Thr Val Leu Asn Val Ala Leu Leu
    610                 615                 620

Asn Val Ile Ser Asn Gln Glu Cys Asn Ile Lys His Arg Gly Arg Val
625                 630                 635                 640

Arg Glu Ser Glu Met Cys Thr Glu Gly Leu Leu Ala Pro Val Gly Ala
                645                 650                 655

Cys Glu Gly Asp Tyr Gly Gly Pro Leu Ala Cys Phe Thr His Asn Cys
            660                 665                 670

Trp Val Leu Glu Gly Ile Ile Ile Pro Asn Arg Val Cys Ala Arg Ser
        675                 680                 685

Arg Trp Pro Ala Val Phe Thr Arg Val Ser Val Phe Val Asp Trp Ile
    690                 695                 700

His Lys Val Met Arg Leu Gly
705                 710

<210> SEQ ID NO 9
<211> LENGTH: 646
<212> TYPE: PRT
<213> ORGANISM: Homo sapiens

<400> SEQUENCE: 9

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

```
Gln Leu Arg Val Tyr Lys Ala Pro Glu Pro Asn Ile Gln Val Asn
130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
                180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Gly Leu Asp Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
                340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Gly Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Asn Val Ala Ile Phe Gly Pro Pro Trp
            420                 425                 430

Met Ala Phe Lys Glu Arg Lys Val Trp Val Lys Glu Asn Met Val Leu
435                 440                 445

Asn Leu Ser Cys Glu Ala Ser Gly His Pro Arg Pro Thr Ile Ser Trp
        450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
530                 535                 540
```

```
Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
            565                 570                 575

Ala Val Leu Tyr Phe Leu Tyr Lys Lys Gly Lys Leu Pro Cys Arg Arg
            580                 585                 590

Ser Gly Lys Gln Glu Ile Thr Leu Pro Pro Ser Arg Lys Ser Glu Leu
            595                 600                 605

Val Val Glu Val Lys Ser Asp Lys Leu Pro Glu Met Gly Leu Leu
            610                 615                 620

Gln Gly Ser Ser Gly Asp Lys Arg Ala Pro Gly Asp Gln Gly Glu Lys
625                 630                 635                 640

Tyr Ile Asp Leu Arg His
                645

<210> SEQ ID NO 10
<211> LENGTH: 654
<212> TYPE: PRT
<213> ORGANISM: Homo sapiens

<400> SEQUENCE: 10

Met Lys Leu Ser Leu Val Ala Ala Met Leu Leu Leu Ser Ala Ala
1               5                   10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
            115                 120                 125

Gln Val Asp Ile Gly Gly Gly Gln Thr Lys Thr Phe Ala Pro Glu Glu
            130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
            195                 200                 205

Tyr Gly Leu Asp Lys Arg Glu Gly Glu Lys Asn Ile Leu Val Phe Asp
            210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270
```

```
Lys Thr Gly Lys Asp Val Arg Lys Asp Asn Arg Ala Val Gln Lys Leu
            275                 280                 285
Arg Arg Glu Val Glu Lys Ala Lys Arg Ala Leu Ser Ser Gln His Gln
290                 295                 300
Ala Arg Ile Glu Ile Glu Ser Phe Tyr Glu Gly Asp Phe Ser Glu
305                 310                 315                 320
Thr Leu Thr Arg Ala Lys Phe Glu Glu Leu Asn Met Asp Leu Phe Arg
                325                 330                 335
Ser Thr Met Lys Pro Val Gln Lys Val Leu Glu Asp Ser Asp Leu Lys
            340                 345                 350
Lys Ser Asp Ile Asp Glu Ile Val Leu Val Gly Gly Ser Thr Arg Ile
        355                 360                 365
Pro Lys Ile Gln Gln Leu Val Lys Glu Phe Phe Asn Gly Lys Glu Pro
    370                 375                 380
Ser Arg Gly Ile Asn Pro Asp Glu Ala Val Ala Tyr Gly Ala Ala Val
385                 390                 395                 400
Gln Ala Gly Val Leu Ser Gly Asp Gln Asp Thr Gly Asp Leu Val Leu
                405                 410                 415
Leu Asp Val Cys Pro Leu Thr Leu Gly Ile Glu Thr Val Gly Gly Val
            420                 425                 430
Met Thr Lys Leu Ile Pro Arg Asn Thr Val Val Pro Thr Lys Lys Ser
        435                 440                 445
Gln Ile Phe Ser Thr Ala Ser Asp Asn Gln Pro Thr Val Thr Ile Lys
    450                 455                 460
Val Tyr Glu Gly Glu Arg Pro Leu Thr Lys Asp Asn His Leu Leu Gly
465                 470                 475                 480
Thr Phe Asp Leu Thr Gly Ile Pro Pro Ala Pro Arg Gly Val Pro Gln
                485                 490                 495
Ile Glu Val Thr Phe Glu Ile Asp Val Asn Gly Ile Leu Arg Val Thr
            500                 505                 510
Ala Glu Asp Lys Gly Thr Gly Asn Lys Asn Lys Ile Thr Ile Thr Asn
        515                 520                 525
Asp Gln Asn Arg Leu Thr Pro Glu Glu Ile Glu Arg Met Val Asn Asp
    530                 535                 540
Ala Glu Lys Phe Ala Glu Glu Asp Lys Lys Leu Lys Glu Arg Ile Asp
545                 550                 555                 560
Thr Arg Asn Glu Leu Glu Ser Tyr Ala Tyr Ser Leu Lys Asn Gln Ile
                565                 570                 575
Gly Asp Lys Glu Lys Leu Gly Gly Lys Leu Ser Ser Glu Asp Lys Glu
            580                 585                 590
Thr Met Glu Lys Ala Val Glu Glu Lys Ile Glu Trp Leu Glu Ser His
        595                 600                 605
Gln Asp Ala Asp Ile Glu Asp Phe Lys Ala Lys Lys Lys Glu Leu Glu
    610                 615                 620
Glu Ile Val Gln Pro Ile Ile Ser Lys Leu Tyr Gly Ser Ala Gly Pro
625                 630                 635                 640
Pro Pro Thr Gly Glu Glu Asp Thr Ala Glu Lys Asp Glu Leu
                645                 650
```

<210> SEQ ID NO 11
<211> LENGTH: 2224
<212> TYPE: PRT
<213> ORGANISM: Homo sapiens

<400> SEQUENCE: 11

```
Met Phe Pro Gly Cys Pro Arg Leu Trp Val Leu Val Val Leu Gly Thr
1               5                   10                  15

Ser Trp Val Gly Trp Gly Ser Gln Gly Thr Glu Ala Ala Gln Leu Arg
            20                  25                  30

Gln Phe Tyr Val Ala Ala Gln Gly Ile Ser Trp Ser Tyr Arg Pro Glu
        35                  40                  45

Pro Thr Asn Ser Ser Leu Asn Leu Ser Val Thr Ser Phe Lys Lys Ile
    50                  55                  60

Val Tyr Arg Glu Tyr Glu Pro Tyr Phe Lys Lys Glu Lys Pro Gln Ser
65                  70                  75                  80

Thr Ile Ser Gly Leu Leu Gly Pro Thr Leu Tyr Ala Glu Val Gly Asp
                85                  90                  95

Ile Ile Lys Val His Phe Lys Asn Lys Ala Asp Lys Pro Leu Ser Ile
            100                 105                 110

His Pro Gln Gly Ile Arg Tyr Ser Lys Leu Ser Glu Gly Ala Ser Tyr
        115                 120                 125

Leu Asp His Thr Phe Pro Ala Glu Lys Met Asp Asp Ala Val Ala Pro
130                 135                 140

Gly Arg Glu Tyr Thr Tyr Glu Trp Ser Ile Ser Glu Asp Ser Gly Pro
145                 150                 155                 160

Thr His Asp Asp Pro Pro Cys Leu Thr His Ile Tyr Tyr Ser His Glu
                165                 170                 175

Asn Leu Ile Glu Asp Phe Asn Ser Gly Leu Ile Gly Pro Leu Leu Ile
            180                 185                 190

Cys Lys Lys Gly Thr Leu Thr Glu Gly Gly Thr Gln Lys Thr Phe Asp
        195                 200                 205

Lys Gln Ile Val Leu Leu Phe Ala Val Phe Asp Glu Ser Lys Ser Trp
    210                 215                 220

Ser Gln Ser Ser Ser Leu Met Tyr Thr Val Asn Gly Tyr Val Asn Gly
225                 230                 235                 240

Thr Met Pro Asp Ile Thr Val Cys Ala His Asp His Ile Ser Trp His
                245                 250                 255

Leu Leu Gly Met Ser Ser Gly Pro Glu Leu Phe Ser Ile His Phe Asn
            260                 265                 270

Gly Gln Val Leu Glu Gln Asn His His Lys Val Ser Ala Ile Thr Leu
        275                 280                 285

Val Ser Ala Thr Ser Thr Thr Ala Asn Met Thr Val Gly Pro Glu Gly
    290                 295                 300

Lys Trp Ile Ile Ser Ser Leu Thr Pro Lys His Leu Gln Ala Gly Met
305                 310                 315                 320

Gln Ala Tyr Ile Asp Ile Lys Asn Cys Pro Lys Lys Thr Arg Asn Leu
                325                 330                 335

Lys Lys Ile Thr Arg Glu Gln Arg Arg His Met Lys Arg Trp Glu Tyr
            340                 345                 350

Phe Ile Ala Ala Glu Glu Val Ile Trp Asp Tyr Ala Pro Val Ile Pro
        355                 360                 365

Ala Asn Met Asp Lys Lys Tyr Arg Ser Gln His Leu Asp Asn Phe Ser
    370                 375                 380

Asn Gln Ile Gly Lys His Tyr Lys Lys Val Met Tyr Thr Gln Tyr Glu
385                 390                 395                 400

Asp Glu Ser Phe Thr Lys His Thr Val Asn Pro Asn Met Lys Glu Asp
                405                 410                 415
```

```
Gly Ile Leu Gly Pro Ile Ile Arg Ala Gln Val Arg Asp Thr Leu Lys
            420             425                 430

Ile Val Phe Lys Asn Met Ala Ser Arg Pro Tyr Ser Ile Tyr Pro His
        435                 440                 445

Gly Val Thr Phe Ser Pro Tyr Glu Asp Glu Val Asn Ser Ser Phe Thr
    450                 455                 460

Ser Gly Arg Asn Asn Thr Met Ile Arg Ala Val Gln Pro Gly Glu Thr
465                 470                 475                 480

Tyr Thr Tyr Lys Trp Asn Ile Leu Glu Phe Asp Glu Pro Thr Glu Asn
                485                 490                 495

Asp Ala Gln Cys Leu Thr Arg Pro Tyr Tyr Ser Asp Val Asp Ile Met
            500                 505                 510

Arg Asp Ile Ala Ser Gly Leu Ile Gly Leu Leu Ile Cys Lys Ser
        515                 520                 525

Arg Ser Leu Asp Arg Arg Gly Ile Gln Arg Ala Ala Asp Ile Glu Gln
    530                 535                 540

Gln Ala Val Phe Ala Val Phe Asp Glu Asn Lys Ser Trp Tyr Leu Glu
545                 550                 555                 560

Asp Asn Ile Asn Lys Phe Cys Glu Asn Pro Asp Glu Val Lys Arg Asp
                565                 570                 575

Asp Pro Lys Phe Tyr Glu Ser Asn Ile Met Ser Thr Ile Asn Gly Tyr
            580                 585                 590

Val Pro Glu Ser Ile Thr Thr Leu Gly Phe Cys Phe Asp Asp Thr Val
        595                 600                 605

Gln Trp His Phe Cys Ser Val Gly Thr Gln Asn Glu Ile Leu Thr Ile
    610                 615                 620

His Phe Thr Gly His Ser Phe Ile Tyr Gly Lys Arg His Glu Asp Thr
625                 630                 635                 640

Leu Thr Leu Phe Pro Met Arg Gly Glu Ser Val Thr Val Thr Met Asp
                645                 650                 655

Asn Val Gly Thr Trp Met Leu Thr Ser Met Asn Ser Ser Pro Arg Ser
            660                 665                 670

Lys Lys Leu Arg Leu Lys Phe Arg Asp Val Lys Cys Ile Pro Asp Asp
        675                 680                 685

Asp Glu Asp Ser Tyr Glu Ile Phe Glu Pro Pro Glu Ser Thr Val Met
    690                 695                 700

Ala Thr Arg Lys Met His Asp Arg Leu Glu Pro Glu Asp Glu Glu Ser
705                 710                 715                 720

Asp Ala Asp Tyr Asp Tyr Gln Asn Arg Leu Ala Ala Ala Leu Gly Ile
                725                 730                 735

Arg Ser Phe Arg Asn Ser Ser Leu Asn Gln Glu Glu Glu Glu Phe Asn
            740                 745                 750

Leu Thr Ala Leu Ala Leu Glu Asn Gly Thr Glu Phe Val Ser Ser Asn
        755                 760                 765

Thr Asp Ile Ile Val Gly Ser Asn Tyr Ser Ser Pro Ser Asn Ile Ser
    770                 775                 780

Lys Phe Thr Val Asn Asn Leu Ala Glu Pro Gln Lys Ala Pro Ser His
785                 790                 795                 800

Gln Gln Ala Thr Thr Ala Gly Ser Pro Leu Arg His Leu Ile Gly Lys
                805                 810                 815

Asn Ser Val Leu Asn Ser Ser Thr Ala Glu His Ser Ser Pro Tyr Ser
            820                 825                 830
```

-continued

Glu Asp Pro Ile Glu Asp Pro Leu Gln Pro Asp Val Thr Gly Ile Arg
        835                 840                 845

Leu Leu Ser Leu Gly Ala Gly Glu Phe Lys Ser Gln Glu His Ala Lys
    850                 855                 860

His Lys Gly Pro Lys Val Glu Arg Asp Gln Ala Ala Lys His Arg Phe
865                 870                 875                 880

Ser Trp Met Lys Leu Leu Ala His Lys Val Gly Arg His Leu Ser Gln
                885                 890                 895

Asp Thr Gly Ser Pro Ser Gly Met Arg Pro Trp Glu Asp Leu Pro Ser
            900                 905                 910

Gln Asp Thr Gly Ser Pro Ser Arg Met Arg Pro Trp Lys Asp Pro Pro
        915                 920                 925

Ser Asp Leu Leu Leu Lys Gln Ser Asn Ser Ser Lys Ile Leu Val
    930                 935                 940

Gly Arg Trp His Leu Ala Ser Glu Lys Gly Ser Tyr Glu Ile Ile Gln
945                 950                 955                 960

Asp Thr Asp Glu Asp Thr Ala Val Asn Asn Trp Leu Ile Ser Pro Gln
                965                 970                 975

Asn Ala Ser Arg Ala Trp Gly Glu Ser Thr Pro Leu Ala Asn Lys Pro
            980                 985                 990

Gly Lys Gln Ser Gly His Pro Lys  Phe Pro Arg Val Arg  His Lys Ser
        995                 1000                1005

Leu Gln  Val Arg Gln Asp  Gly Lys Ser Arg Leu  Lys Lys Ser
    1010                1015                 1020

Gln Phe  Leu Ile Lys Thr  Arg Lys Lys Lys Glu  Lys His Thr
    1025                1030                 1035

His His  Ala Pro Leu Ser  Pro Arg Thr Phe His  Pro Leu Arg Ser
    1040                1045                 1050

Glu Ala  Tyr Asn Thr Phe  Ser Glu Arg Arg Leu  Lys His Ser Leu
    1055                1060                 1065

Val Leu  His Lys Ser Asn  Glu Thr Ser Leu Pro  Thr Asp Leu Asn
    1070                1075                 1080

Gln Thr  Leu Pro Ser Met  Asp Phe Gly Trp Ile  Ala Ser Leu Pro
    1085                1090                 1095

Asp His  Asn Gln Asn Ser  Ser Asn Asp Thr Gly  Gln Ala Ser Cys
    1100                1105                 1110

Pro Pro  Gly Leu Tyr Gln  Thr Val Pro Pro Glu  Glu His Tyr Gln
    1115                1120                 1125

Thr Phe  Pro Ile Gln Asp  Pro Asp Gln Met His  Ser Thr Ser Asp
    1130                1135                 1140

Pro Ser  His Arg Ser Ser  Ser Pro Glu Leu Ser  Glu Met Leu Glu
    1145                1150                 1155

Tyr Asp  Arg Ser His Lys  Ser Phe Pro Thr Asp  Ile Ser Gln Met
    1160                1165                 1170

Ser Pro  Ser Ser Glu His  Glu Val Trp Gln Thr  Val Ile Ser Pro
    1175                1180                 1185

Asp Leu  Ser Gln Val Thr  Leu Ser Pro Glu Leu  Ser Gln Thr Asn
    1190                1195                 1200

Leu Ser  Pro Asp Leu Ser  His Thr Thr Leu Ser  Pro Glu Leu Ile
    1205                1210                 1215

Gln Arg  Asn Leu Ser Pro  Ala Leu Gly Gln Met  Pro Ile Ser Pro
    1220                1225                 1230

```
Asp Leu Ser His Thr Thr Leu Ser Pro Asp Leu Ser His Thr Thr
1235                1240                1245

Leu Ser Leu Asp Leu Ser Gln Thr Asn Leu Ser Pro Glu Leu Ser
1250                1255                1260

Gln Thr Asn Leu Ser Pro Ala Leu Gly Gln Met Pro Leu Ser Pro
1265                1270                1275

Asp Leu Ser His Thr Thr Leu Ser Leu Asp Phe Ser Gln Thr Asn
1280                1285                1290

Leu Ser Pro Glu Leu Ser His Met Thr Leu Ser Pro Glu Leu Ser
1295                1300                1305

Gln Thr Asn Leu Ser Pro Ala Leu Gly Gln Met Pro Ile Ser Pro
1310                1315                1320

Asp Leu Ser His Thr Thr Leu Ser Leu Asp Phe Ser Gln Thr Asn
1325                1330                1335

Leu Ser Pro Glu Leu Ser Gln Thr Asn Leu Ser Pro Ala Leu Gly
1340                1345                1350

Gln Met Pro Leu Ser Pro Asp Pro Ser His Thr Thr Leu Ser Leu
1355                1360                1365

Asp Leu Ser Gln Thr Asn Leu Ser Pro Glu Leu Ser Gln Thr Asn
1370                1375                1380

Leu Ser Pro Asp Leu Ser Glu Met Pro Leu Phe Ala Asp Leu Ser
1385                1390                1395

Gln Ile Pro Leu Thr Pro Asp Leu Asp Gln Met Thr Leu Ser Pro
1400                1405                1410

Asp Leu Gly Glu Thr Asp Leu Ser Pro Asn Phe Gly Gln Met Ser
1415                1420                1425

Leu Ser Pro Asp Leu Ser Gln Val Thr Leu Ser Pro Asp Ile Ser
1430                1435                1440

Asp Thr Thr Leu Leu Pro Asp Leu Ser Gln Ile Ser Pro Pro Pro
1445                1450                1455

Asp Leu Asp Gln Ile Phe Tyr Pro Ser Glu Ser Ser Gln Ser Leu
1460                1465                1470

Leu Leu Gln Glu Phe Asn Glu Ser Phe Pro Tyr Pro Asp Leu Gly
1475                1480                1485

Gln Met Pro Ser Pro Ser Ser Pro Thr Leu Asn Asp Thr Phe Leu
1490                1495                1500

Ser Lys Glu Phe Asn Pro Leu Val Ile Val Gly Leu Ser Lys Asp
1505                1510                1515

Gly Thr Asp Tyr Ile Glu Ile Ile Pro Lys Glu Glu Val Gln Ser
1520                1525                1530

Ser Glu Asp Asp Tyr Ala Glu Ile Asp Tyr Val Pro Tyr Asp Asp
1535                1540                1545

Pro Tyr Lys Thr Asp Val Arg Thr Asn Ile Asn Ser Ser Arg Asp
1550                1555                1560

Pro Asp Asn Ile Ala Ala Trp Tyr Leu Arg Ser Asn Asn Gly Asn
1565                1570                1575

Arg Arg Asn Tyr Tyr Ile Ala Ala Glu Glu Ile Ser Trp Asp Tyr
1580                1585                1590

Ser Glu Phe Val Gln Arg Glu Thr Asp Ile Glu Asp Ser Asp Asp
1595                1600                1605

Ile Pro Glu Asp Thr Thr Tyr Lys Lys Val Val Phe Arg Lys Tyr
1610                1615                1620
```

```
Leu Asp Ser Thr Phe Thr Lys Arg Asp Pro Arg Gly Glu Tyr Glu
1625                1630                1635

Glu His Leu Gly Ile Leu Gly Pro Ile Ile Arg Ala Glu Val Asp
1640                1645                1650

Asp Val Ile Gln Val Arg Phe Lys Asn Leu Ala Ser Arg Pro Tyr
1655                1660                1665

Ser Leu His Ala His Gly Leu Ser Tyr Glu Lys Ser Ser Glu Gly
1670                1675                1680

Lys Thr Tyr Glu Asp Asp Ser Pro Glu Trp Phe Lys Glu Asp Asn
1685                1690                1695

Ala Val Gln Pro Asn Ser Ser Tyr Thr Tyr Val Trp His Ala Thr
1700                1705                1710

Glu Arg Ser Gly Pro Glu Ser Pro Gly Ser Ala Cys Arg Ala Trp
1715                1720                1725

Ala Tyr Tyr Ser Ala Val Asn Pro Glu Lys Asp Ile His Ser Gly
1730                1735                1740

Leu Ile Gly Pro Leu Leu Ile Cys Gln Lys Gly Ile Leu His Lys
1745                1750                1755

Asp Ser Asn Met Pro Met Asp Met Arg Glu Phe Val Leu Leu Phe
1760                1765                1770

Met Thr Phe Asp Glu Lys Lys Ser Trp Tyr Tyr Glu Lys Lys Ser
1775                1780                1785

Arg Ser Ser Trp Arg Leu Thr Ser Ser Glu Met Lys Lys Ser His
1790                1795                1800

Glu Phe His Ala Ile Asn Gly Met Ile Tyr Ser Leu Pro Gly Leu
1805                1810                1815

Lys Met Tyr Glu Gln Glu Trp Val Arg Leu His Leu Leu Asn Ile
1820                1825                1830

Gly Gly Ser Gln Asp Ile His Val Val His Phe His Gly Gln Thr
1835                1840                1845

Leu Leu Glu Asn Gly Asn Lys Gln His Gln Leu Gly Val Trp Pro
1850                1855                1860

Leu Leu Pro Gly Ser Phe Lys Thr Leu Glu Met Lys Ala Ser Lys
1865                1870                1875

Pro Gly Trp Trp Leu Leu Asn Thr Glu Val Gly Glu Asn Gln Arg
1880                1885                1890

Ala Gly Met Gln Thr Pro Phe Leu Ile Met Asp Arg Asp Cys Arg
1895                1900                1905

Met Pro Met Gly Leu Ser Thr Gly Ile Ile Ser Asp Ser Gln Ile
1910                1915                1920

Lys Ala Ser Glu Phe Leu Gly Tyr Trp Glu Pro Arg Leu Ala Arg
1925                1930                1935

Leu Asn Asn Gly Gly Ser Tyr Asn Ala Trp Ser Val Glu Lys Leu
1940                1945                1950

Ala Ala Glu Phe Ala Ser Lys Pro Trp Ile Gln Val Asp Met Gln
1955                1960                1965

Lys Glu Val Ile Ile Thr Gly Ile Gln Thr Gln Gly Ala Lys His
1970                1975                1980

Tyr Leu Lys Ser Cys Tyr Thr Thr Glu Phe Tyr Val Ala Tyr Ser
1985                1990                1995

Ser Asn Gln Ile Asn Trp Gln Ile Phe Lys Gly Asn Ser Thr Arg
2000                2005                2010
```

-continued

```
Asn Val Met Tyr Phe Asn Gly Asn Ser Asp Ala Ser Thr Ile Lys
    2015                2020                2025

Glu Asn Gln Phe Asp Pro Pro Ile Val Ala Arg Tyr Ile Arg Ile
    2030                2035                2040

Ser Pro Thr Arg Ala Tyr Asn Arg Pro Thr Leu Arg Leu Glu Leu
    2045                2050                2055

Gln Gly Cys Glu Val Asn Gly Cys Ser Thr Pro Leu Gly Met Glu
    2060                2065                2070

Asn Gly Lys Ile Glu Asn Lys Gln Ile Thr Ala Ser Ser Phe Lys
    2075                2080                2085

Lys Ser Trp Trp Gly Asp Tyr Trp Glu Pro Phe Arg Ala Arg Leu
    2090                2095                2100

Asn Ala Gln Gly Arg Val Asn Ala Trp Gln Ala Lys Ala Asn Asn
    2105                2110                2115

Asn Lys Gln Trp Leu Glu Ile Asp Leu Leu Lys Ile Lys Lys Ile
    2120                2125                2130

Thr Ala Ile Ile Thr Gln Gly Cys Lys Ser Leu Ser Ser Glu Met
    2135                2140                2145

Tyr Val Lys Ser Tyr Thr Ile His Tyr Ser Glu Gln Gly Val Glu
    2150                2155                2160

Trp Lys Pro Tyr Arg Leu Lys Ser Ser Met Val Asp Lys Ile Phe
    2165                2170                2175

Glu Gly Asn Thr Asn Thr Lys Gly His Val Lys Asn Phe Phe Asn
    2180                2185                2190

Pro Pro Ile Ile Ser Arg Phe Ile Arg Val Ile Pro Lys Thr Trp
    2195                2200                2205

Asn Gln Ser Ile Ala Leu Arg Leu Glu Leu Phe Gly Cys Asp Ile
    2210                2215                2220

Tyr

<210> SEQ ID NO 12
<211> LENGTH: 142
<212> TYPE: PRT
<213> ORGANISM: Homo sapiens

<400> SEQUENCE: 12

Val Asp Ser Gly Asn Asp Val Thr Asp Ile Ala Asp Asp Gly Cys Pro
1               5                   10                  15

Lys Pro Pro Glu Ile Ala His Gly Tyr Val Glu His Ser Val Arg Tyr
            20                  25                  30

Gln Cys Lys Asn Tyr Tyr Lys Leu Arg Thr Glu Gly Asp Gly Val Tyr
        35                  40                  45

Thr Leu Asn Asp Lys Lys Gln Trp Ile Asn Lys Ala Val Gly Asp Lys
    50                  55                  60

Leu Pro Glu Cys Glu Ala Asp Asp Gly Cys Pro Lys Pro Pro Glu Ile
65                  70                  75                  80

Ala His Gly Tyr Val Glu His Ser Val Arg Tyr Gln Cys Lys Asn Tyr
                85                  90                  95

Tyr Lys Leu Arg Thr Glu Gly Asp Gly Val Tyr Thr Leu Asn Asn Glu
            100                 105                 110

Lys Gln Trp Ile Asn Lys Ala Val Gly Asp Lys Leu Pro Glu Cys Glu
        115                 120                 125

Ala Val Cys Gly Lys Pro Lys Asn Pro Ala Asn Pro Val Gln
    130                 135                 140
```

<210> SEQ ID NO 13
<211> LENGTH: 1156
<212> TYPE: PRT
<213> ORGANISM: Homo sapiens

<400> SEQUENCE: 13

```
Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
                20                  25                  30

Leu Leu Leu Ser Ala Cys Phe Val Thr Ser Ser Leu Gly Gly Thr Asp
            35                  40                  45

Lys Glu Leu Arg Leu Val Asp Gly Glu Asn Lys Cys Ser Gly Arg Val
50                  55                  60

Glu Val Lys Val Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ser Ala Gly Ser Gly Arg
                100                 105                 110

Ile Trp Met Asp His Val Ser Cys Arg Gly Asn Glu Ser Ala Leu Trp
            115                 120                 125

Asp Cys Lys His Asp Gly Trp Gly Lys His Ser Asn Cys Thr His Gln
130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
                180                 185                 190

Ala Ser Val Ile Cys Arg Gln Leu Glu Cys Gly Ser Ala Val Ser Phe
            195                 200                 205

Ser Gly Ser Ser Asn Phe Gly Glu Gly Ser Gly Pro Ile Trp Phe Asp
210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
                260                 265                 270

Thr Glu Cys Ser Gly Arg Leu Glu Val Arg Phe Gln Gly Glu Trp Gly
            275                 280                 285

Thr Ile Cys Asp Asp Gly Trp Asp Ser Tyr Asp Ala Ala Val Ala Cys
290                 295                 300

Lys Gln Leu Gly Cys Pro Thr Ala Val Thr Ala Ile Gly Arg Val Asn
305                 310                 315                 320

Ala Ser Lys Gly Phe Gly His Ile Trp Leu Asp Ser Val Ser Cys Gln
                325                 330                 335

Gly His Glu Pro Ala Ile Trp Gln Cys Lys His His Glu Trp Gly Lys
                340                 345                 350

His Tyr Cys Asn His Asn Glu Asp Ala Gly Val Thr Cys Ser Asp Gly
            355                 360                 365

Ser Asp Leu Glu Leu Arg Leu Arg Gly Gly Gly Ser Arg Cys Ala Gly
370                 375                 380
```

-continued

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
            405                 410                 415

Gly Ser Ala Leu Lys Thr Ser Tyr Gln Val Tyr Ser Lys Ile Gln Ala
            420                 425                 430

Thr Asn Thr Trp Leu Phe Leu Ser Ser Cys Asn Gly Asn Glu Thr Ser
            435                 440                 445

Leu Trp Asp Cys Lys Asn Trp Gln Trp Gly Gly Leu Thr Cys Asp His
    450                 455                 460

Tyr Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Ile Cys Asp Ser Asp Phe Ser Leu Glu Ala Ala
            500                 505                 510

Ser Val Leu Cys Arg Glu Leu Gln Cys Gly Thr Val Val Ser Ile Leu
            515                 520                 525

Gly Gly Ala His Phe Gly Glu Gly Asn Gly Gln Ile Trp Ala Glu Glu
530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Gly Ala Trp Gly Ser Leu Cys
            595                 600                 605

Asn Ser His Trp Asp Ile Glu Asp Ala His Val Leu Cys Gln Gln Leu
            610                 615                 620

Lys Cys Gly Val Ala Leu Ser Thr Pro Gly Gly Ala Arg Phe Gly Lys
625                 630                 635                 640

Gly Asn Gly Gln Ile Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Glu Gln Val Ala Ser Val Ile Cys Ser Gly Asn Gln Ser Gln
            675                 680                 685

Thr Leu Ser Ser Cys Asn Ser Ser Ser Leu Gly Pro Thr Arg Pro Thr
            690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
            755                 760                 765

Thr Gly Ser Ala His Phe Gly Glu Gly Thr Gly Pro Ile Trp Leu Asp
            770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
              805                 810                 815

Ile Cys Ser Glu Phe Met Ser Leu Arg Leu Thr Ser Glu Ala Ser Arg
              820                 825                 830

Glu Ala Cys Ala Gly Arg Leu Glu Val Phe Tyr Asn Gly Ala Trp Gly
              835                 840                 845

Thr Val Gly Lys Ser Ser Met Ser Glu Thr Thr Val Gly Val Val Cys
850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
              885                 890                 895

Lys Gly Pro Asp Thr Leu Trp Gln Cys Pro Ser Ser Pro Trp Glu Lys
              900                 905                 910

Arg Leu Ala Ser Pro Ser Glu Glu Thr Trp Ile Thr Cys Asp Asn Lys
              915                 920                 925

Ile Arg Leu Gln Glu Gly Pro Thr Ser Cys Ser Gly Arg Val Glu Ile
              930                 935                 940

Trp His Gly Gly Ser Trp Gly Thr Val Cys Asp Asp Ser Trp Asp Leu
945                 950                 955                 960

Asp Asp Ala Gln Val Val Cys Gln Gln Leu Gly Cys Gly Pro Ala Leu
              965                 970                 975

Lys Ala Phe Lys Glu Ala Glu Phe Gly Gln Gly Thr Gly Pro Ile Trp
              980                 985                 990

Leu Asn Glu Val Lys Cys Lys Gly Asn Glu Ser Ser Leu Trp Asp Cys
              995                 1000                1005

Pro Ala Arg Arg Trp Gly His Ser Glu Cys Gly His Lys Glu Asp
              1010                1015                1020

Ala Ala Val Asn Cys Thr Asp Ile Ser Val Gln Lys Thr Pro Gln
              1025                1030                1035

Lys Ala Thr Thr Gly Arg Ser Ser Arg Gln Ser Ser Phe Ile Ala
              1040                1045                1050

Val Gly Ile Leu Gly Val Val Leu Leu Ala Ile Phe Val Ala Leu
              1055                1060                1065

Phe Phe Leu Thr Lys Lys Arg Arg Gln Arg Gln Arg Leu Ala Val
              1070                1075                1080

Ser Ser Arg Gly Glu Asn Leu Val His Gln Ile Gln Tyr Arg Glu
              1085                1090                1095

Met Asn Ser Cys Leu Asn Ala Asp Asp Leu Asp Leu Met Asn Ser
              1100                1105                1110

Ser Glu Asn Ser His Glu Ser Ala Asp Phe Ser Ala Ala Glu Leu
              1115                1120                1125

Ile Ser Val Ser Lys Phe Leu Pro Ile Ser Gly Met Glu Lys Glu
              1130                1135                1140

Ala Ile Leu Ser His Thr Glu Lys Glu Asn Gly Asn Leu
              1145                1150                1155

<210> SEQ ID NO 14
<211> LENGTH: 858
<212> TYPE: PRT
<213> ORGANISM: Homo sapiens

<400> SEQUENCE: 14

```
Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Ala Ser Trp Thr Arg Pro Glu Lys Gln Glu Thr Leu Asp Gly His
        355                 360                 365

Met Val Val Arg Ser His Ala Arg Val Ser Ser Leu Thr Leu Lys Ser
370                 375                 380

Ile Gln Tyr Thr Asp Ala Gly Glu Tyr Ile Cys Thr Ala Ser Asn Thr
385                 390                 395                 400

Ile Gly Gln Asp Ser Gln Ser Met Tyr Leu Glu Val Gln Tyr Ala Pro
                405                 410                 415
```

Lys Leu Gln Gly Pro Val Ala Val Tyr Thr Trp Glu Gly Asn Gln Val
            420                 425                 430

Asn Ile Thr Cys Glu Val Phe Ala Tyr Pro Ser Ala Thr Ile Ser Trp
        435                 440                 445

Phe Arg Asp Gly Gln Leu Leu Pro Ser Ser Asn Tyr Ser Asn Ile Lys
    450                 455                 460

Ile Tyr Asn Thr Pro Ser Ala Ser Tyr Leu Glu Val Thr Pro Asp Ser
465                 470                 475                 480

Glu Asn Asp Phe Gly Asn Tyr Asn Cys Thr Ala Val Asn Arg Ile Gly
                485                 490                 495

Gln Glu Ser Leu Glu Phe Ile Leu Val Gln Ala Asp Thr Pro Ser Ser
            500                 505                 510

Pro Ser Ile Asp Gln Val Glu Pro Tyr Ser Ser Thr Ala Gln Val Gln
        515                 520                 525

Phe Asp Glu Pro Glu Ala Thr Gly Gly Val Pro Ile Leu Lys Tyr Lys
    530                 535                 540

Ala Glu Trp Arg Ala Val Gly Glu Glu Val Trp His Ser Lys Trp Tyr
545                 550                 555                 560

Asp Ala Lys Glu Ala Ser Met Glu Gly Ile Val Thr Ile Val Gly Leu
                565                 570                 575

Lys Pro Glu Thr Thr Tyr Ala Val Arg Leu Ala Ala Leu Asn Gly Lys
            580                 585                 590

Gly Leu Gly Glu Ile Ser Ala Ala Ser Glu Phe Lys Thr Gln Pro Val
        595                 600                 605

Gln Gly Glu Pro Ser Ala Pro Lys Leu Glu Gly Gln Met Gly Glu Asp
    610                 615                 620

Gly Asn Ser Ile Lys Val Asn Leu Ile Lys Gln Asp Asp Gly Gly Ser
625                 630                 635                 640

Pro Ile Arg His Tyr Leu Val Arg Tyr Arg Ala Leu Ser Ser Glu Trp
                645                 650                 655

Lys Pro Glu Ile Arg Leu Pro Ser Gly Ser Asp His Val Met Leu Lys
            660                 665                 670

Ser Leu Asp Trp Asn Ala Glu Tyr Glu Val Tyr Val Val Ala Glu Asn
        675                 680                 685

Gln Gln Gly Lys Ser Lys Ala Ala His Phe Val Phe Arg Thr Ser Ala
    690                 695                 700

Gln Pro Thr Ala Ile Pro Ala Asn Gly Ser Pro Thr Ser Gly Leu Ser
705                 710                 715                 720

Thr Gly Ala Ile Val Gly Ile Leu Ile Val Ile Phe Val Leu Leu Leu
                725                 730                 735

Val Val Val Asp Ile Thr Cys Tyr Phe Leu Asn Lys Cys Gly Leu Phe
            740                 745                 750

Met Cys Ile Ala Val Asn Leu Cys Gly Lys Ala Gly Pro Gly Ala Lys
        755                 760                 765

Gly Lys Asp Met Glu Glu Gly Lys Ala Ala Phe Ser Lys Asp Glu Ser
    770                 775                 780

Lys Glu Pro Ile Val Glu Val Arg Thr Glu Glu Arg Thr Pro Asn
785                 790                 795                 800

His Asp Gly Gly Lys His Thr Glu Pro Asn Glu Thr Thr Pro Leu Thr
                805                 810                 815

Glu Pro Glu Lys Gly Pro Val Glu Ala Lys Pro Glu Cys Gln Glu Thr
            820                 825                 830

Glu Thr Lys Pro Ala Pro Ala Glu Val Lys Thr Val Pro Asn Asp Ala
            835                 840                 845

Thr Gln Thr Lys Glu Asn Glu Ser Lys Ala
            850                 855

<210> SEQ ID NO 15
<211> LENGTH: 1404
<212> TYPE: PRT
<213> ORGANISM: Homo sapiens

<400> SEQUENCE: 15

Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
                20                  25                  30

Arg Cys Gly Glu Gly Tyr Ser Arg Asp Ala Thr Cys Asn Cys Asp Tyr
            35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Pro Asn Lys Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Val Glu Thr Lys Glu
        275                 280                 285

Thr Thr Thr Thr Asn Lys Gln Thr Ser Thr Asp Gly Lys Glu Lys Thr
    290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

-continued

```
Thr Thr Pro Lys Glu Pro Ala Ser Thr Thr Pro Lys Glu Pro Thr Pro
            355                 360                 365
Thr Thr Ile Lys Ser Ala Pro Thr Thr Pro Lys Glu Pro Ala Pro Thr
            370                 375                 380
Thr Thr Lys Ser Ala Pro Thr Thr Pro Lys Glu Pro Ala Pro Thr Thr
385                 390                 395                 400
Thr Lys Glu Pro Ala Pro Thr Thr Pro Lys Glu Pro Ala Pro Thr Thr
                405                 410                 415
Thr Lys Glu Pro Ala Pro Thr Thr Lys Ser Ala Pro Thr Thr Pro
                420                 425                 430
Lys Glu Pro Ala Pro Thr Thr Pro Lys Lys Pro Ala Pro Thr Thr Pro
            435                 440                 445
Lys Glu Pro Ala Pro Thr Thr Pro Lys Glu Pro Thr Pro Thr Thr Pro
            450                 455                 460
Lys Glu Pro Ala Pro Thr Thr Lys Glu Pro Ala Pro Thr Thr Pro Lys
465                 470                 475                 480
Glu Pro Ala Pro Thr Ala Pro Lys Lys Pro Ala Pro Thr Thr Pro Lys
                485                 490                 495
Glu Pro Ala Pro Thr Thr Pro Lys Glu Pro Ala Pro Thr Thr Thr Lys
            500                 505                 510
Glu Pro Ser Pro Thr Thr Pro Lys Glu Pro Ala Pro Thr Thr Thr Lys
            515                 520                 525
Ser Ala Pro Thr Thr Thr Lys Glu Pro Ala Pro Thr Thr Lys Ser
            530                 535                 540
Ala Pro Thr Thr Pro Lys Glu Pro Ser Pro Thr Thr Lys Glu Pro
545                 550                 555                 560
Ala Pro Thr Thr Pro Lys Glu Pro Ala Pro Thr Thr Pro Lys Lys Pro
                565                 570                 575
Ala Pro Thr Thr Pro Lys Glu Pro Ala Pro Thr Thr Pro Lys Glu Pro
                580                 585                 590
Ala Pro Thr Thr Lys Lys Pro Ala Pro Thr Thr Pro Lys Glu Pro
            595                 600                 605
Ala Pro Thr Thr Pro Lys Glu Thr Ala Pro Thr Thr Pro Lys Lys Leu
            610                 615                 620
Thr Pro Thr Thr Pro Glu Lys Leu Ala Pro Thr Thr Pro Glu Lys Pro
625                 630                 635                 640
Ala Pro Thr Thr Pro Glu Glu Leu Ala Pro Thr Thr Pro Glu Glu Pro
                645                 650                 655
Thr Pro Thr Thr Pro Glu Glu Pro Ala Pro Thr Thr Pro Lys Ala Ala
            660                 665                 670
Ala Pro Asn Thr Pro Lys Glu Pro Ala Pro Thr Thr Pro Lys Glu Pro
            675                 680                 685
Ala Pro Thr Thr Pro Lys Glu Pro Ala Pro Thr Thr Pro Lys Glu Thr
            690                 695                 700
Ala Pro Thr Thr Pro Lys Gly Thr Ala Pro Thr Thr Leu Lys Glu Pro
705                 710                 715                 720
Ala Pro Thr Thr Pro Lys Lys Pro Ala Pro Lys Glu Leu Ala Pro Thr
                725                 730                 735
Thr Thr Lys Glu Pro Thr Ser Thr Thr Cys Asp Lys Pro Ala Pro Thr
            740                 745                 750
Thr Pro Lys Gly Thr Ala Pro Thr Thr Pro Lys Glu Pro Ala Pro Thr
            755                 760                 765
```

Thr Pro Lys Glu Pro Ala Pro Thr Thr Pro Lys Gly Thr Ala Pro Thr
770                 775                 780

Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys
                820                 825                 830

Glu Pro Ala Pro Thr Thr Pro Lys Pro Ala Pro Thr Thr Pro Glu
                835                 840                 845

Thr Pro Pro Pro Thr Thr Ser Glu Val Ser Thr Pro Thr Thr Lys
850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
                900                 905                 910

Thr Thr Ala Lys Asp Lys Thr Thr Glu Arg Asp Leu Arg Thr Thr Pro
                915                 920                 925

Glu Thr Thr Thr Ala Ala Pro Lys Met Thr Lys Glu Thr Ala Thr Thr
930                 935                 940

Thr Glu Lys Thr Thr Glu Ser Lys Ile Thr Ala Thr Thr Gln Val
945                 950                 955                 960

Thr Ser Thr Thr Thr Gln Asp Thr Thr Pro Phe Lys Ile Thr Thr Leu
                965                 970                 975

Lys Thr Thr Thr Leu Ala Pro Lys Val Thr Thr Thr Lys Lys Thr Ile
                980                 985                 990

Thr Thr Thr Glu Ile Met Asn Lys Pro Glu Glu Thr Ala Lys Pro Lys
                995                 1000                1005

Asp Arg Ala Thr Asn Ser Lys Ala Thr Thr Pro Lys Pro Gln Lys
        1010                1015                1020

Pro Thr Lys Ala Pro Lys Lys Pro Thr Ser Thr Lys Lys Pro Lys
        1025                1030                1035

Thr Met Pro Arg Val Arg Lys Pro Lys Thr Thr Pro Thr Pro Arg
        1040                1045                1050

Lys Met Thr Ser Thr Met Pro Glu Leu Asn Pro Thr Ser Arg Ile
        1055                1060                1065

Ala Glu Ala Met Leu Gln Thr Thr Thr Arg Pro Asn Gln Thr Pro
        1070                1075                1080

Asn Ser Lys Leu Val Glu Val Asn Pro Lys Ser Glu Asp Ala Gly
        1085                1090                1095

Gly Ala Glu Gly Glu Thr Pro His Met Leu Leu Arg Pro His Val
        1100                1105                1110

Phe Met Pro Glu Val Thr Pro Asp Met Asp Tyr Leu Pro Arg Val
        1115                1120                1125

Pro Asn Gln Gly Ile Ile Ile Asn Pro Met Leu Ser Asp Glu Thr
        1130                1135                1140

Asn Ile Cys Asn Gly Lys Pro Val Asp Gly Leu Thr Thr Leu Arg
        1145                1150                1155

Asn Gly Thr Leu Val Ala Phe Arg Gly His Tyr Phe Trp Met Leu
        1160                1165                1170

```
Ser Pro Phe Ser Pro Pro Ser Pro Ala Arg Arg Ile Thr Glu Val
    1175            1180                1185

Trp Gly Ile Pro Ser Pro Ile Asp Thr Val Phe Thr Arg Cys Asn
    1190            1195                1200

Cys Glu Gly Lys Thr Phe Phe Lys Asp Ser Gln Tyr Trp Arg
    1205            1210                1215

Phe Thr Asn Asp Ile Lys Asp Ala Gly Tyr Pro Lys Pro Ile Phe
    1220            1225                1230

Lys Gly Phe Gly Gly Leu Thr Gly Gln Ile Val Ala Ala Leu Ser
    1235            1240                1245

Thr Ala Lys Tyr Lys Asn Trp Pro Glu Ser Val Tyr Phe Phe Lys
    1250            1255                1260

Arg Gly Gly Ser Ile Gln Gln Tyr Ile Tyr Lys Gln Glu Pro Val
    1265            1270                1275

Gln Lys Cys Pro Gly Arg Arg Pro Ala Leu Asn Tyr Pro Val Tyr
    1280            1285                1290

Gly Glu Thr Thr Gln Val Arg Arg Arg Phe Glu Arg Ala Ile
    1295            1300                1305

Gly Pro Ser Gln Thr His Thr Ile Arg Ile Gln Tyr Ser Pro Ala
    1310            1315                1320

Arg Leu Ala Tyr Gln Asp Lys Gly Val Leu His Asn Glu Val Lys
    1325            1330                1335

Val Ser Ile Leu Trp Arg Gly Leu Pro Asn Val Thr Ser Ala
    1340            1345                1350

Ile Ser Leu Pro Asn Ile Arg Lys Pro Asp Gly Tyr Asp Tyr Tyr
    1355            1360                1365

Ala Phe Ser Lys Asp Gln Tyr Tyr Asn Ile Asp Val Pro Ser Arg
    1370            1375                1380

Thr Ala Arg Ala Ile Thr Thr Arg Ser Gly Gln Thr Leu Ser Lys
    1385            1390                1395

Val Trp Tyr Asn Cys Pro
    1400

<210> SEQ ID NO 16
<211> LENGTH: 449
<212> TYPE: PRT
<213> ORGANISM: Homo sapiens

<400> SEQUENCE: 16

Met Leu Pro Ala Ala Thr Ala Ser Leu Leu Gly Pro Leu Leu Thr Ala
1               5                   10                  15

Cys Ala Leu Leu Pro Phe Ala Gln Gly Gln Thr Pro Asn Tyr Thr Arg
                20                  25                  30

Pro Val Phe Leu Cys Gly Gly Asp Val Lys Gly Glu Ser Gly Tyr Val
            35                  40                  45

Ala Ser Glu Gly Phe Pro Asn Leu Tyr Pro Pro Asn Lys Glu Cys Ile
    50                  55                  60

Trp Thr Ile Thr Val Pro Glu Gly Gln Thr Val Ser Leu Ser Phe Arg
65                  70                  75                  80

Val Phe Asp Leu Glu Leu His Pro Ala Cys Arg Tyr Asp Ala Leu Glu
                85                  90                  95

Val Phe Ala Gly Ser Gly Thr Ser Gly Gln Arg Leu Gly Arg Phe Cys
            100                 105                 110

Gly Thr Phe Arg Pro Ala Pro Leu Val Ala Pro Gly Asn Gln Val Thr
        115                 120                 125
```

Leu Arg Met Thr Thr Asp Glu Gly Thr Gly Arg Gly Phe Leu Leu
130                 135                 140

Trp Tyr Ser Gly Arg Ala Thr Ser Gly Thr Glu His Gln Phe Cys Gly
145                 150                 155                 160

Gly Arg Leu Glu Lys Ala Gln Gly Thr Leu Thr Thr Pro Asn Trp Pro
                165                 170                 175

Glu Ser Asp Tyr Pro Pro Gly Ile Ser Cys Ser Trp His Ile Ile Ala
            180                 185                 190

Pro Pro Asp Gln Val Ile Ala Leu Thr Phe Glu Lys Phe Asp Leu Glu
        195                 200                 205

Pro Asp Thr Tyr Cys Arg Tyr Asp Ser Val Ser Val Phe Asn Gly Ala
    210                 215                 220

Val Ser Asp Asp Ser Arg Arg Leu Gly Lys Phe Cys Gly Asp Ala Val
225                 230                 235                 240

Pro Gly Ser Ile Ser Ser Glu Gly Asn Glu Leu Leu Val Gln Phe Val
                245                 250                 255

Ser Asp Leu Ser Val Thr Ala Asp Gly Phe Ser Ala Ser Tyr Lys Thr
            260                 265                 270

Leu Pro Arg Gly Thr Ala Lys Glu Gly Gln Gly Pro Gly Pro Lys Arg
        275                 280                 285

Gly Thr Glu Pro Lys Val Lys Leu Pro Pro Lys Ser Gln Pro Pro Glu
    290                 295                 300

Lys Thr Glu Glu Ser Pro Ser Ala Pro Asp Ala Pro Thr Cys Pro Lys
305                 310                 315                 320

Gln Cys Arg Arg Thr Gly Thr Leu Gln Ser Asn Phe Cys Ala Ser Ser
                325                 330                 335

Leu Val Val Thr Ala Thr Val Lys Ser Met Val Arg Glu Pro Gly Glu
            340                 345                 350

Gly Leu Ala Val Thr Val Ser Leu Ile Gly Ala Tyr Lys Thr Gly Gly
        355                 360                 365

Leu Asp Leu Pro Ser Pro Pro Thr Gly Ala Ser Leu Lys Phe Tyr Val
    370                 375                 380

Pro Cys Lys Gln Cys Pro Pro Met Lys Lys Gly Val Ser Tyr Leu Leu
385                 390                 395                 400

Met Gly Gln Val Glu Glu Asn Arg Gly Pro Val Leu Pro Pro Glu Ser
                405                 410                 415

Phe Val Val Leu His Arg Pro Asn Gln Asp Gln Ile Leu Thr Asn Leu
            420                 425                 430

Ser Lys Arg Lys Cys Pro Ser Gln Pro Val Arg Ala Ala Ala Ser Gln
        435                 440                 445

Asp

<210> SEQ ID NO 17
<211> LENGTH: 627
<212> TYPE: PRT
<213> ORGANISM: Homo sapiens

<400> SEQUENCE: 17

Met Ala Arg Gly Ser Val Ser Asp Glu Glu Met Met Glu Leu Arg Glu
1               5                   10                  15

Ala Phe Ala Lys Val Asp Thr Asp Gly Asn Gly Tyr Ile Ser Phe Asn
                20                  25                  30

Glu Leu Asn Asp Leu Phe Lys Ala Ala Cys Leu Pro Leu Pro Gly Tyr
            35                  40                  45

```
Arg Val Arg Glu Ile Thr Glu Asn Leu Met Ala Thr Gly Asp Leu Asp
 50                  55                  60

Gln Asp Gly Arg Ile Ser Phe Asp Glu Phe Ile Lys Ile Phe His Gly
 65                  70                  75                  80

Leu Lys Ser Thr Asp Val Ala Lys Thr Phe Arg Lys Ala Ile Asn Lys
                 85                  90                  95

Lys Glu Gly Ile Cys Ala Ile Gly Gly Thr Ser Glu Gln Ser Ser Val
            100                 105                 110

Gly Thr Gln His Ser Tyr Ser Glu Glu Lys Tyr Ala Phe Val Asn
            115                 120                 125

Trp Ile Asn Lys Ala Leu Glu Asn Asp Pro Asp Cys Arg His Val Ile
130                 135                 140

Pro Met Asn Pro Asn Thr Asn Asp Leu Phe Asn Ala Val Gly Asp Gly
145                 150                 155                 160

Ile Val Leu Cys Lys Met Ile Asn Leu Ser Val Pro Asp Thr Ile Asp
                165                 170                 175

Glu Arg Thr Ile Asn Lys Lys Leu Thr Pro Phe Thr Ile Gln Glu
            180                 185                 190

Asn Leu Asn Leu Ala Leu Asn Ser Ala Ser Ala Ile Gly Cys His Val
195                 200                 205

Val Asn Ile Gly Ala Glu Asp Leu Lys Glu Gly Lys Pro Tyr Leu Val
210                 215                 220

Leu Gly Leu Leu Trp Gln Val Ile Lys Ile Gly Leu Phe Ala Asp Ile
225                 230                 235                 240

Glu Leu Ser Arg Asn Glu Ala Leu Ile Ala Leu Leu Arg Glu Gly Glu
                245                 250                 255

Ser Leu Glu Asp Leu Met Lys Leu Ser Pro Glu Glu Leu Leu Leu Arg
            260                 265                 270

Trp Ala Asn Tyr His Leu Glu Asn Ala Gly Cys Asn Lys Ile Gly Asn
            275                 280                 285

Phe Ser Thr Asp Ile Lys Asp Ser Lys Ala Tyr Tyr His Leu Leu Glu
            290                 295                 300

Gln Val Ala Pro Lys Gly Asp Glu Glu Gly Val Pro Ala Val Val Ile
305                 310                 315                 320

Asp Met Ser Gly Leu Arg Glu Lys Asp Ile Gln Arg Ala Glu Cys
                325                 330                 335

Met Leu Gln Gln Ala Glu Arg Leu Gly Cys Arg Gln Phe Val Thr Ala
            340                 345                 350

Thr Asp Val Val Arg Gly Asn Pro Lys Leu Asn Leu Ala Phe Ile Ala
            355                 360                 365

Asn Leu Phe Asn Arg Tyr Pro Ala Leu His Lys Pro Glu Asn Gln Asp
            370                 375                 380

Ile Asp Trp Gly Ala Leu Glu Gly Glu Thr Arg Glu Glu Arg Thr Phe
385                 390                 395                 400

Arg Asn Trp Met Asn Ser Leu Gly Val Asn Pro Arg Val Asn His Leu
                405                 410                 415

Tyr Ser Asp Leu Ser Asp Ala Leu Val Ile Phe Gln Leu Tyr Glu Lys
            420                 425                 430

Ile Lys Val Pro Val Asp Trp Asn Arg Val Asn Lys Pro Pro Tyr Pro
            435                 440                 445

Lys Leu Gly Gly Asn Met Lys Lys Leu Glu Asn Cys Asn Tyr Ala Val
450                 455                 460
```

```
Glu Leu Gly Lys Asn Gln Ala Lys Phe Ser Leu Val Gly Ile Gly
465                 470                 475                 480

Gln Asp Leu Asn Glu Gly Asn Arg Thr Leu Thr Leu Ala Leu Ile Trp
            485                 490                 495

Gln Leu Met Arg Arg Tyr Thr Leu Asn Ile Leu Glu Glu Ile Gly Gly
        500                 505                 510

Gly Gln Lys Val Asn Asp Asp Ile Ile Val Asn Trp Val Asn Glu Thr
                515                 520                 525

Leu Arg Glu Ala Lys Lys Ser Ser Ile Ser Ser Phe Lys Asp Pro
530                 535                 540

Lys Ile Ser Thr Ser Leu Pro Val Leu Asp Leu Ile Asp Ala Ile Gln
545                 550                 555                 560

Pro Gly Ser Ile Asn Tyr Asp Leu Leu Lys Thr Glu Asn Leu Asn Asp
                565                 570                 575

Asp Glu Lys Leu Asn Asn Ala Lys Tyr Ala Ile Ser Met Ala Arg Lys
            580                 585                 590

Ile Gly Ala Arg Val Tyr Ala Leu Pro Glu Asp Leu Val Glu Val Asn
        595                 600                 605

Pro Lys Met Val Met Thr Val Phe Ala Cys Leu Met Gly Lys Gly Met
610                 615                 620

Lys Arg Val
625

<210> SEQ ID NO 18
<211> LENGTH: 732
<212> TYPE: PRT
<213> ORGANISM: Homo sapiens

<400> SEQUENCE: 18

Met Ser Glu Thr Ser Arg Thr Ala Phe Gly Gly Arg Arg Ala Val Pro
1               5                   10                  15

Pro Asn Asn Ser Asn Ala Ala Glu Asp Asp Leu Pro Thr Val Glu Leu
            20                  25                  30

Gln Gly Val Val Pro Arg Gly Val Asn Leu Gln Glu Phe Leu Asn Val
        35                  40                  45

Thr Ser Val His Leu Phe Lys Glu Arg Trp Asp Thr Asn Lys Val Asp
50                  55                  60

His His Thr Asp Lys Tyr Glu Asn Asn Lys Leu Ile Val Arg Arg Gly
65                  70                  75                  80

Gln Ser Phe Tyr Val Gln Ile Asp Phe Ser Arg Pro Tyr Asp Pro Arg
                85                  90                  95

Arg Asp Leu Phe Arg Val Glu Tyr Val Ile Gly Arg Tyr Pro Gln Glu
            100                 105                 110

Asn Lys Gly Thr Tyr Ile Pro Val Pro Ile Val Ser Glu Leu Gln Ser
        115                 120                 125

Gly Lys Trp Gly Ala Lys Ile Val Met Arg Glu Asp Arg Ser Val Arg
    130                 135                 140

Leu Ser Ile Gln Ser Ser Pro Lys Cys Ile Val Gly Lys Phe Arg Met
145                 150                 155                 160

Tyr Val Ala Val Trp Thr Pro Tyr Gly Val Leu Arg Thr Ser Arg Asn
                165                 170                 175

Pro Glu Thr Asp Thr Tyr Ile Leu Phe Asn Pro Trp Cys Glu Asp Asp
            180                 185                 190

Ala Val Tyr Leu Asp Asn Glu Lys Glu Arg Glu Glu Tyr Val Leu Asn
        195                 200                 205
```

-continued

Asp Ile Gly Val Ile Phe Tyr Gly Glu Val Asn Asp Ile Lys Thr Arg
210                 215                 220

Ser Trp Ser Tyr Gly Gln Phe Glu Asp Gly Ile Leu Asp Thr Cys Leu
225                 230                 235                 240

Tyr Val Met Asp Arg Ala Gln Met Asp Leu Ser Gly Arg Gly Asn Pro
            245                 250                 255

Ile Lys Val Ser Arg Val Gly Ser Ala Met Val Asn Ala Lys Asp Asp
        260                 265                 270

Glu Gly Val Leu Val Gly Ser Trp Asp Asn Ile Tyr Ala Tyr Gly Val
            275                 280                 285

Pro Pro Ser Ala Trp Thr Gly Ser Val Asp Ile Leu Leu Glu Tyr Arg
290                 295                 300

Ser Ser Glu Asn Pro Val Arg Tyr Gly Gln Cys Trp Val Phe Ala Gly
305                 310                 315                 320

Val Phe Asn Thr Phe Leu Arg Cys Leu Gly Ile Pro Ala Arg Ile Val
            325                 330                 335

Thr Asn Tyr Phe Ser Ala His Asp Asn Asp Ala Asn Leu Gln Met Asp
            340                 345                 350

Ile Phe Leu Glu Glu Asp Gly Asn Val Asn Ser Lys Leu Thr Lys Asp
            355                 360                 365

Ser Val Trp Asn Tyr His Cys Trp Asn Glu Ala Trp Met Thr Arg Pro
370                 375                 380

Asp Leu Pro Val Gly Phe Gly Gly Trp Gln Ala Val Asp Ser Thr Pro
385                 390                 395                 400

Gln Glu Asn Ser Asp Gly Met Tyr Arg Cys Gly Pro Ala Ser Val Gln
            405                 410                 415

Ala Ile Lys His Gly His Val Cys Phe Gln Phe Asp Ala Pro Phe Val
            420                 425                 430

Phe Ala Glu Val Asn Ser Asp Leu Ile Tyr Ile Thr Ala Lys Lys Asp
            435                 440                 445

Gly Thr His Val Val Glu Asn Val Asp Ala Thr His Ile Gly Lys Leu
450                 455                 460

Ile Val Thr Lys Gln Ile Gly Gly Asp Gly Met Met Asp Ile Thr Asp
465                 470                 475                 480

Thr Tyr Lys Phe Gln Glu Gly Gln Glu Glu Arg Leu Ala Leu Glu
            485                 490                 495

Thr Ala Leu Met Tyr Gly Ala Lys Lys Pro Leu Asn Thr Glu Gly Val
            500                 505                 510

Met Lys Ser Arg Ser Asn Val Asp Met Asp Phe Glu Val Glu Asn Ala
            515                 520                 525

Val Leu Gly Lys Asp Phe Lys Leu Ser Ile Thr Phe Arg Asn Asn Ser
530                 535                 540

His Asn Arg Tyr Thr Ile Thr Ala Tyr Leu Ser Ala Asn Ile Thr Phe
545                 550                 555                 560

Tyr Thr Gly Val Pro Lys Ala Glu Phe Lys Lys Glu Thr Phe Asp Val
            565                 570                 575

Thr Leu Glu Pro Leu Ser Phe Lys Lys Glu Ala Val Leu Ile Gln Ala
            580                 585                 590

Gly Glu Tyr Met Gly Gln Leu Leu Glu Gln Ala Ser Leu His Phe Phe
            595                 600                 605

Val Thr Ala Arg Ile Asn Glu Thr Arg Asp Val Leu Ala Lys Gln Lys
610                 615                 620

```
Ser Thr Val Leu Thr Ile Pro Glu Ile Ile Lys Val Arg Gly Thr
625                 630                 635                 640

Gln Val Val Gly Ser Asp Met Thr Val Thr Val Gln Phe Thr Asn Pro
                645                 650                 655

Leu Lys Glu Thr Leu Arg Asn Val Trp Val His Leu Asp Gly Pro Gly
            660                 665                 670

Val Thr Arg Pro Met Lys Lys Met Phe Arg Glu Ile Arg Pro Asn Ser
            675                 680                 685

Thr Val Gln Trp Glu Glu Val Cys Arg Pro Trp Val Ser Gly His Arg
            690                 695                 700

Lys Leu Ile Ala Ser Met Ser Ser Asp Ser Leu Arg His Val Tyr Gly
705                 710                 715                 720

Glu Leu Asp Val Gln Ile Gln Arg Arg Pro Ser Met
                725                 730

<210> SEQ ID NO 19
<211> LENGTH: 382
<212> TYPE: PRT
<213> ORGANISM: Homo sapiens

<400> SEQUENCE: 19

Met Gly Leu Leu Leu Pro Leu Ala Leu Cys Ile Leu Val Leu Cys Cys
1               5                   10                  15

Gly Ala Met Ser Pro Pro Gln Leu Ala Leu Asn Pro Ser Ala Leu Leu
            20                  25                  30

Ser Arg Gly Cys Asn Asp Ser Asp Val Leu Ala Val Ala Gly Phe Ala
        35                  40                  45

Leu Arg Asp Ile Asn Lys Asp Arg Lys Asp Gly Tyr Val Leu Arg Leu
50                  55                  60

Asn Arg Val Asn Asp Ala Gln Glu Tyr Arg Arg Gly Gly Leu Gly Ser
65                  70                  75                  80

Leu Phe Tyr Leu Thr Leu Asp Val Leu Glu Thr Asp Cys His Val Leu
                85                  90                  95

Arg Lys Lys Ala Trp Gln Asp Cys Gly Met Arg Ile Phe Phe Glu Ser
            100                 105                 110

Val Tyr Gly Gln Cys Lys Ala Ile Phe Tyr Met Asn Asn Pro Ser Arg
        115                 120                 125

Val Leu Tyr Leu Ala Ala Tyr Asn Cys Thr Leu Arg Pro Val Ser Lys
130                 135                 140

Lys Lys Ile Tyr Met Thr Cys Pro Asp Cys Pro Ser Ser Ile Pro Thr
145                 150                 155                 160

Asp Ser Ser Asn His Gln Val Leu Glu Ala Ala Thr Glu Ser Leu Ala
                165                 170                 175

Lys Tyr Asn Asn Glu Asn Thr Ser Lys Gln Tyr Ser Leu Phe Lys Val
            180                 185                 190

Thr Arg Ala Ser Ser Gln Trp Val Val Gly Pro Ser Tyr Phe Val Glu
        195                 200                 205

Tyr Leu Ile Lys Glu Ser Pro Cys Thr Lys Ser Gln Ala Ser Ser Cys
210                 215                 220

Ser Leu Gln Ser Ser Asp Ser Val Pro Val Gly Leu Cys Lys Gly Ser
225                 230                 235                 240

Leu Thr Arg Thr His Trp Glu Lys Phe Val Ser Val Thr Cys Asp Phe
                245                 250                 255

Phe Glu Ser Gln Ala Pro Ala Thr Gly Ser Glu Asn Ser Ala Val Asn
            260                 265                 270
```

```
Gln Lys Pro Thr Asn Leu Pro Lys Val Glu Glu Ser Gln Gln Lys Asn
            275                 280                 285
Thr Pro Pro Thr Asp Ser Pro Ser Lys Ala Gly Pro Arg Gly Ser Val
        290                 295                 300
Gln Tyr Leu Pro Asp Leu Asp Asp Lys Asn Ser Gln Glu Lys Gly Pro
305                 310                 315                 320
Gln Glu Ala Phe Pro Val His Leu Asp Leu Thr Thr Asn Pro Gln Gly
                325                 330                 335
Glu Thr Leu Asp Ile Ser Phe Leu Phe Leu Gly Pro Met Glu Glu Lys
            340                 345                 350
Leu Val Val Leu Pro Phe Pro Lys Glu Lys Ala Arg Thr Ala Glu Cys
        355                 360                 365
Pro Gly Pro Ala Gln Asn Ala Ser Pro Leu Val Leu Pro Pro
    370                 375                 380

<210> SEQ ID NO 20
<211> LENGTH: 90
<212> TYPE: PRT
<213> ORGANISM: Homo sapiens

<400> SEQUENCE: 20

Met Ala Cys Pro Leu Asp Gln Ala Ile Gly Leu Leu Val Ala Ile Phe
1               5                   10                  15
His Lys Tyr Ser Gly Arg Glu Gly Asp Lys His Thr Leu Ser Lys Lys
            20                  25                  30
Glu Leu Lys Glu Leu Ile Gln Lys Glu Leu Thr Ile Gly Ser Lys Leu
        35                  40                  45
Gln Asp Ala Glu Ile Ala Arg Leu Met Glu Asp Leu Asp Arg Asn Lys
    50                  55                  60
Asp Gln Glu Val Asn Phe Gln Glu Tyr Val Thr Phe Leu Gly Ala Leu
65                  70                  75                  80
Ala Leu Ile Tyr Asn Glu Ala Leu Lys Gly
            85                  90

<210> SEQ ID NO 21
<211> LENGTH: 220
<212> TYPE: PRT
<213> ORGANISM: Homo sapiens

<400> SEQUENCE: 21

Met Gly Ala Ala Ala Arg Thr Leu Arg Leu Ala Leu Gly Leu Leu Leu
1               5                   10                  15
Leu Ala Thr Leu Leu Arg Pro Ala Asp Ala Cys Ser Cys Ser Pro Val
            20                  25                  30
His Pro Gln Gln Ala Phe Cys Asn Ala Asp Val Val Ile Arg Ala Lys
        35                  40                  45
Ala Val Ser Glu Lys Glu Val Asp Ser Gly Asn Asp Ile Tyr Gly Asn
    50                  55                  60
Pro Ile Lys Arg Ile Gln Tyr Glu Ile Lys Gln Ile Lys Met Phe Lys
65                  70                  75                  80
Gly Pro Glu Lys Asp Ile Glu Phe Ile Tyr Thr Ala Pro Ser Ser Ala
            85                  90                  95
Val Cys Gly Val Ser Leu Asp Val Gly Gly Lys Lys Glu Tyr Leu Ile
            100                 105                 110
Ala Gly Lys Ala Glu Gly Asp Gly Lys Met His Ile Thr Leu Cys Asp
        115                 120                 125
```

```
Phe Ile Val Pro Trp Asp Thr Leu Ser Thr Thr Gln Lys Lys Ser Leu
130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
                180                 185                 190

Cys Ile Lys Arg Ser Asp Gly Ser Cys Ala Trp Tyr Arg Gly Ala Ala
            195                 200                 205

Pro Pro Lys Gln Glu Phe Leu Asp Ile Glu Asp Pro
210                 215                 220

<210> SEQ ID NO 22
<211> LENGTH: 199
<212> TYPE: PRT
<213> ORGANISM: Homo sapiens

<400> SEQUENCE: 22

Met Ser Ser Gly Asn Ala Lys Ile Gly His Pro Ala Pro Asn Phe Lys
1               5                   10                  15

Ala Thr Ala Val Met Pro Asp Gly Gln Phe Lys Asp Ile Ser Leu Ser
                20                  25                  30

Asp Tyr Lys Gly Lys Tyr Val Val Phe Phe Phe Tyr Pro Leu Asp Phe
            35                  40                  45

Thr Phe Val Cys Pro Thr Glu Ile Ile Ala Phe Ser Asp Arg Ala Glu
        50                  55                  60

Glu Phe Lys Lys Leu Asn Cys Gln Val Ile Gly Ala Ser Val Asp Ser
65                  70                  75                  80

His Phe Cys His Leu Ala Trp Val Asn Thr Pro Lys Lys Gln Gly Gly
                85                  90                  95

Leu Gly Pro Met Asn Ile Pro Leu Val Ser Asp Pro Lys Arg Thr Ile
                100                 105                 110

Ala Gln Asp Tyr Gly Val Leu Lys Ala Asp Glu Gly Ile Ser Phe Arg
            115                 120                 125

Gly Leu Phe Ile Ile Asp Asp Lys Gly Ile Leu Arg Gln Ile Thr Val
        130                 135                 140

Asn Asp Leu Pro Val Gly Arg Ser Val Asp Glu Thr Leu Arg Leu Val
145                 150                 155                 160

Gln Ala Phe Gln Phe Thr Asp Lys His Gly Glu Val Cys Pro Ala Gly
                165                 170                 175

Trp Lys Pro Gly Ser Asp Thr Ile Lys Pro Asp Val Gln Lys Ser Lys
                180                 185                 190

Glu Tyr Phe Ser Lys Gln Lys
            195

<210> SEQ ID NO 23
<211> LENGTH: 972
<212> TYPE: PRT
<213> ORGANISM: Homo sapiens

<400> SEQUENCE: 23

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30
```

-continued

```
Lys Pro Gly Ala Thr Val Thr Leu Arg Cys Val Gly Asn Gly Ser Val
             35                  40                  45
Glu Trp Asp Gly Pro Pro Ser Pro His Trp Thr Leu Tyr Ser Asp Gly
 50                  55                  60
Ser Ser Ser Ile Leu Ser Thr Asn Asn Ala Thr Phe Gln Asn Thr Gly
 65                  70                  75                  80
Thr Tyr Arg Cys Thr Glu Pro Gly Asp Pro Leu Gly Gly Ser Ala Ala
                 85                  90                  95
Ile His Leu Tyr Val Lys Asp Pro Ala Arg Pro Trp Asn Val Leu Ala
                100                 105                 110
Gln Glu Val Val Phe Glu Asp Gln Asp Ala Leu Leu Pro Cys Leu
                115                 120                 125
Leu Thr Asp Pro Val Leu Glu Ala Gly Val Ser Leu Val Arg Val Arg
    130                 135                 140
Gly Arg Pro Leu Met Arg His Thr Asn Tyr Ser Phe Ser Pro Trp His
145                 150                 155                 160
Gly Phe Thr Ile His Arg Ala Lys Phe Ile Gln Ser Gln Asp Tyr Gln
                165                 170                 175
Cys Ser Ala Leu Met Gly Gly Arg Lys Val Met Ser Ile Ser Ile Arg
                180                 185                 190
Leu Lys Val Gln Lys Val Ile Pro Gly Pro Pro Ala Leu Thr Leu Val
    195                 200                 205
Pro Ala Glu Leu Val Arg Ile Arg Gly Glu Ala Ala Gln Ile Val Cys
    210                 215                 220
Ser Ala Ser Ser Val Asp Val Asn Phe Asp Val Phe Leu Gln His Asn
225                 230                 235                 240
Asn Thr Lys Leu Ala Ile Pro Gln Gln Ser Asp Phe His Asn Asn Arg
                245                 250                 255
Tyr Gln Lys Val Leu Thr Leu Asn Leu Asp Gln Val Asp Phe Gln His
                260                 265                 270
Ala Gly Asn Tyr Ser Cys Val Ala Ser Asn Val Gln Gly Lys His Ser
                275                 280                 285
Thr Ser Met Phe Phe Arg Val Val Glu Ser Ala Tyr Leu Asn Leu Ser
    290                 295                 300
Ser Glu Gln Asn Leu Ile Gln Glu Val Thr Val Gly Glu Gly Leu Asn
305                 310                 315                 320
Leu Lys Val Met Val Glu Ala Tyr Pro Gly Leu Gln Gly Phe Asn Trp
                325                 330                 335
Thr Tyr Leu Gly Pro Phe Ser Asp His Gln Pro Glu Pro Lys Leu Ala
                340                 345                 350
Asn Ala Thr Thr Lys Asp Thr Tyr Arg His Thr Phe Thr Leu Ser Leu
                355                 360                 365
Pro Arg Leu Lys Pro Ser Glu Ala Gly Arg Tyr Ser Phe Leu Ala Arg
    370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                405                 410                 415
Leu Leu Cys Ala Ala Ser Gly Tyr Pro Gln Pro Asn Val Thr Trp Leu
                420                 425                 430
Gln Cys Ser Gly His Thr Asp Arg Cys Asp Glu Ala Gln Val Leu Gln
    435                 440                 445
```

-continued

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
            610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
    850                 855                 860

```
Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
            885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Glu Leu Glu Glu
            930                 935                 940

Glu Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
            965                 970

<210> SEQ ID NO 24
<211> LENGTH: 361
<212> TYPE: PRT
<213> ORGANISM: Homo sapiens

<400> SEQUENCE: 24

Met Ala Pro Thr Glu Pro Trp Ser Pro Ser Pro Gly Ser Ala Pro Trp
1               5                   10                  15

Asp Tyr Ser Gly Leu Asp Gly Leu Glu Glu Leu Glu Leu Cys Pro Ala
                20                  25                  30

Gly Asp Leu Pro Tyr Gly Tyr Val Tyr Ile Pro Ala Leu Tyr Leu Ala
            35                  40                  45

Ala Phe Ala Val Gly Leu Leu Gly Asn Ala Phe Val Val Trp Leu Leu
50                  55                  60

Ala Gly Arg Arg Gly Pro Arg Arg Leu Val Asp Thr Phe Val Leu His
65                  70                  75                  80

Leu Ala Ala Ala Asp Leu Gly Phe Val Leu Thr Leu Pro Leu Trp Ala
                85                  90                  95

Ala Ala Ala Ala Leu Gly Gly Arg Trp Pro Phe Gly Asp Gly Leu Cys
            100                 105                 110

Lys Leu Ser Ser Phe Ala Leu Ala Gly Thr Arg Cys Ala Gly Ala Leu
            115                 120                 125

Leu Leu Ala Gly Met Ser Val Asp Arg Tyr Leu Ala Val Val Lys Leu
130                 135                 140

Leu Glu Ala Arg Pro Leu Arg Thr Pro Arg Cys Ala Leu Ala Ser Cys
145                 150                 155                 160

Cys Gly Val Trp Ala Val Ala Leu Leu Ala Gly Leu Pro Ser Leu Val
                165                 170                 175

Tyr Arg Gly Leu Gln Pro Leu Pro Gly Gly Gln Asp Ser Gln Cys Gly
            180                 185                 190

Glu Glu Pro Ser His Ala Phe Gln Gly Leu Ser Leu Leu Leu Leu Leu
            195                 200                 205

Leu Thr Phe Val Leu Pro Leu Val Thr Leu Phe Cys Tyr Cys Arg
210                 215                 220

Ile Ser Arg Arg Leu Arg Arg Pro His Val Gly Arg Ala Arg Arg
225                 230                 235                 240

Asn Ser Leu Arg Ile Ile Phe Ala Ile Glu Ser Thr Phe Val Gly Ser
                245                 250                 255

Trp Leu Pro Phe Ser Ala Leu Arg Ala Val Phe His Leu Ala Arg Leu
            260                 265                 270
```

```
Gly Ala Leu Pro Leu Pro Cys Pro Leu Leu Ala Leu Arg Trp Gly
            275                 280                 285

Leu Thr Ile Ala Thr Cys Leu Ala Phe Val Asn Ser Cys Ala Asn Pro
290                 295                 300

Leu Ile Tyr Leu Leu Asp Arg Ser Phe Arg Ala Arg Ala Leu Asp
305                 310                 315                 320

Gly Ala Cys Gly Arg Thr Gly Arg Leu Ala Arg Ile Ser Ser Ala
            325                 330                 335

Ser Ser Leu Ser Arg Asp Asp Ser Ser Val Phe Arg Cys Arg Ala Gln
            340                 345                 350

Ala Ala Asn Thr Ala Ser Ala Ser Trp
            355                 360

<210> SEQ ID NO 25
<211> LENGTH: 204
<212> TYPE: PRT
<213> ORGANISM: Homo sapiens

<400> SEQUENCE: 25

Met Val Ser Val Leu Ser Leu Leu Leu Leu Gly Pro Ala Val
1               5                   10                  15

Leu Gln Glu Thr Arg Asp Gly His Tyr Ser Leu Thr Tyr Leu Tyr Thr
                20                  25                  30

Gly Leu Ser Arg Ser Gly Lys Gly Thr His Arg Leu Gln Gly Thr Val
            35                  40                  45

Phe Leu Asn Gly His Ala Phe Phe His Tyr Asn Ser Glu Asp Arg Lys
    50                  55                  60

Ala Glu Pro Leu Gly Pro Trp Arg His Ala Glu Gly Val Glu Asp Trp
65                  70                  75                  80

Glu Lys Gln Ser Gln Val Gln Lys Ala Arg Glu Asp Ile Phe Met Glu
                85                  90                  95

Thr Leu Asn Asn Ile Met Glu Tyr Tyr Asn Asp Gly Asn Asp Asn Pro
            100                 105                 110

Pro Ser Val Val Val Thr Ser His Gln Ala Pro Gly Glu Lys Lys Lys
        115                 120                 125

Leu Lys Cys Leu Ala Tyr Asp Phe Tyr Pro Gly Lys Ile Asp Val His
    130                 135                 140

Trp Thr Arg Ala Gly Glu Val Gln Glu Pro Glu Leu Arg Gly Asp Val
145                 150                 155                 160

Leu His Gly Gly Asn Gly Thr Tyr Leu Thr Trp Leu Leu Val His Val
                165                 170                 175

Pro Pro Gln Asp Thr Ala Pro Tyr Ser Cys His Val Gln His Ser Ser
            180                 185                 190

Leu Ala Gln Pro Leu Val Val Pro Trp Glu Ala Ser
        195                 200

<210> SEQ ID NO 26
<211> LENGTH: 362
<212> TYPE: PRT
<213> ORGANISM: Homo sapiens

<400> SEQUENCE: 26

Met Arg Val Thr Ala Pro Arg Thr Val Leu Leu Leu Ser Gly Ala
1               5                   10                  15

Leu Ala Leu Thr Glu Thr Trp Ala Gly Ser His Ser Met Arg Tyr Phe
                20                  25                  30
```

Tyr Thr Ala Met Ser Arg Pro Gly Arg Gly Glu Pro Arg Phe Ile Ala
                35                  40                  45

Val Gly Tyr Val Asp Asp Thr Gln Phe Val Arg Phe Asp Ser Asp Ala
 50                  55                  60

Ala Ser Pro Arg Met Ala Pro Arg Ala Pro Trp Ile Glu Gln Glu Gly
65                  70                  75                  80

Pro Glu Tyr Trp Asp Arg Glu Thr Gln Ile Ser Lys Thr Asn Thr Gln
                85                  90                  95

Thr Tyr Arg Glu Ser Leu Arg Asn Leu Arg Gly Tyr Tyr Asn Gln Ser
            100                 105                 110

Glu Ala Gly Ser His Thr Leu Gln Arg Met Tyr Gly Cys Asp Val Gly
        115                 120                 125

Pro Asp Gly Arg Leu Leu Arg Gly His Asp Gln Ser Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Ile Pro Ile Val Gly Ile Val Ala Gly Leu Ala Val Leu Ala Val
305                 310                 315                 320

Val Val Ile Gly Ala Val Val Ala Thr Val Met Cys Arg Arg Lys Ser
                325                 330                 335

Ser Gly Gly Lys Gly Gly Ser Tyr Ser Gln Ala Ala Ser Ser Asp Ser
            340                 345                 350

Ala Gln Gly Ser Asp Val Ser Leu Thr Ala
        355                 360

<210> SEQ ID NO 27
<211> LENGTH: 653
<212> TYPE: PRT
<213> ORGANISM: Homo sapiens

<400> SEQUENCE: 27

Met Pro Val Gly Gly Leu Leu Pro Leu Phe Ser Ser Pro Ala Gly Gly
1               5                   10                  15

Val Leu Gly Gly Gly Leu Gly Gly Gly Gly Arg Lys Gly Ser Gly
            20                  25                  30

Pro Ala Ala Leu Arg Leu Thr Glu Lys Phe Val Leu Leu Leu Val Phe
        35                  40                  45

-continued

Ser Ala Phe Ile Thr Leu Cys Phe Gly Ala Ile Phe Phe Leu Pro Asp
    50                  55                  60

Ser Ser Lys Leu Leu Ser Gly Val Leu Phe His Ser Ser Pro Ala Leu
65              70                  75                  80

Gln Pro Ala Ala Asp His Lys Pro Gly Pro Gly Ala Arg Ala Glu Asp
                85                  90                  95

Ala Ala Glu Gly Arg Ala Arg Arg Glu Glu Gly Ala Pro Gly Asp
            100                 105                 110

Pro Glu Ala Ala Leu Glu Asp Asn Leu Ala Arg Ile Arg Glu Asn His
                115                 120                 125

Glu Arg Ala Leu Arg Glu Ala Lys Glu Thr Leu Gln Lys Leu Pro Glu
130                 135                 140

Glu Ile Gln Arg Asp Ile Leu Leu Glu Lys Lys Val Ala Gln Asp
145                 150                 155                 160

Gln Leu Arg Asp Lys Ala Pro Phe Arg Gly Leu Pro Pro Val Asp Phe
                165                 170                 175

Val Pro Pro Ile Gly Val Glu Ser Arg Glu Pro Ala Asp Ala Ala Ile
                180                 185                 190

Arg Glu Lys Arg Ala Lys Ile Lys Glu Met Met Lys His Ala Trp Asn
            195                 200                 205

Asn Tyr Lys Gly Tyr Ala Trp Gly Leu Asn Glu Leu Lys Pro Ile Ser
    210                 215                 220

Lys Gly Gly His Ser Ser Leu Phe Gly Asn Ile Lys Gly Ala Thr
225                 230                 235                 240

Ile Val Asp Ala Leu Asp Thr Leu Phe Ile Met Glu Met Lys His Glu
                245                 250                 255

Phe Glu Glu Ala Lys Ser Trp Val Glu Glu Asn Leu Asp Phe Asn Val
            260                 265                 270

Asn Ala Glu Ile Ser Val Phe Glu Val Asn Ile Arg Phe Val Gly Gly
        275                 280                 285

Leu Leu Ser Ala Tyr Tyr Leu Ser Gly Glu Glu Ile Phe Arg Lys Lys
    290                 295                 300

Ala Val Glu Leu Gly Val Lys Leu Leu Pro Ala Phe His Thr Pro Ser
305                 310                 315                 320

Gly Ile Pro Trp Ala Leu Leu Asn Met Lys Ser Gly Ile Gly Arg Asn
                325                 330                 335

Trp Pro Trp Ala Ser Gly Gly Ser Ser Ile Leu Ala Glu Phe Gly Thr
            340                 345                 350

Leu His Leu Glu Phe Met His Leu Ser His Leu Ser Gly Asn Pro Ile
    355                 360                 365

Phe Ala Glu Lys Val Met Asn Ile Arg Thr Val Leu Asn Lys Leu Glu
        370                 375                 380

Lys Pro Gln Gly Leu Tyr Pro Asn Tyr Leu Asn Pro Ser Ser Gly Gln
385                 390                 395                 400

Trp Gly Gln His His Val Ser Val Gly Gly Leu Gly Asp Ser Phe Tyr
                405                 410                 415

Glu Tyr Leu Leu Lys Ala Trp Leu Met Ser Asp Lys Thr Asp Leu Glu
            420                 425                 430

Ala Lys Lys Met Tyr Phe Asp Ala Val Gln Ala Ile Glu Thr His Leu
    435                 440                 445

Ile Arg Lys Ser Ser Ser Gly Leu Thr Tyr Ile Ala Glu Trp Lys Gly
        450                 455                 460

```
Gly Leu Leu Glu His Lys Met Gly His Leu Thr Cys Phe Ala Gly
465                 470                 475                 480

Met Phe Ala Leu Gly Ala Asp Ala Ala Pro Glu Gly Met Ala Gln His
            485                 490                 495

Tyr Leu Glu Leu Gly Ala Glu Ile Ala Arg Thr Cys His Glu Ser Tyr
                500                 505                 510

Asn Arg Thr Phe Met Lys Leu Gly Pro Glu Ala Phe Arg Phe Asp Gly
            515                 520                 525

Gly Val Glu Ala Ile Ala Thr Arg Gln Asn Glu Lys Tyr Tyr Ile Leu
        530                 535                 540

Arg Pro Glu Val Met Glu Thr Tyr Met Tyr Met Trp Arg Leu Thr His
545                 550                 555                 560

Asp Pro Lys Tyr Arg Lys Trp Ala Trp Glu Ala Val Glu Ala Leu Glu
                565                 570                 575

Asn His Cys Arg Val Asn Gly Gly Tyr Ser Gly Leu Arg Asp Val Tyr
            580                 585                 590

Leu Leu His Glu Ser Tyr Asp Asp Val Gln Gln Ser Phe Phe Leu Ala
        595                 600                 605

Glu Thr Leu Lys Tyr Leu Tyr Leu Ile Phe Ser Asp Asp Leu Leu
                610                 615                 620

Pro Leu Glu His Trp Ile Phe Asn Ser Glu Ala His Leu Leu Pro Ile
625                 630                 635                 640

Leu Pro Lys Asp Lys Lys Glu Val Glu Ile Arg Glu Glu
                645                 650

<210> SEQ ID NO 28
<211> LENGTH: 132
<212> TYPE: PRT
<213> ORGANISM: Homo sapiens

<400> SEQUENCE: 28

Met Ser Asn Lys Phe Leu Gly Thr Trp Lys Leu Val Ser Ser Glu Asn
1               5                   10                  15

Phe Asp Asp Tyr Met Lys Ala Leu Gly Val Gly Leu Ala Thr Arg Lys
                20                  25                  30

Leu Gly Asn Leu Ala Lys Pro Thr Val Ile Ile Ser Lys Lys Gly Asp
            35                  40                  45

Ile Ile Thr Ile Arg Thr Glu Ser Thr Phe Lys Asn Thr Glu Ile Ser
        50                  55                  60

Phe Lys Leu Gly Gln Glu Phe Glu Glu Thr Thr Ala Asp Asn Arg Lys
65                  70                  75                  80

Thr Lys Ser Ile Val Thr Leu Gln Arg Gly Ser Leu Asn Gln Val Gln
                85                  90                  95

Arg Trp Asp Gly Lys Glu Thr Thr Ile Lys Arg Lys Leu Val Asn Gly
                100                 105                 110

Lys Met Val Ala Glu Cys Lys Met Lys Gly Val Val Cys Thr Arg Ile
            115                 120                 125

Tyr Glu Lys Val
    130

<210> SEQ ID NO 29
<211> LENGTH: 207
<212> TYPE: PRT
<213> ORGANISM: Homo sapiens
```

-continued

<400> SEQUENCE: 29

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205

<210> SEQ ID NO 30
<211> LENGTH: 365
<212> TYPE: PRT
<213> ORGANISM: Homo sapiens

<400> SEQUENCE: 30

Met Ala Val Met Ala Pro Arg Thr Leu Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Lys Met Glu Pro Arg Ala Pro Trp Ile Glu Gln Glu Gly
65                  70                  75                  80

Pro Glu Tyr Trp Asp Gln Glu Thr Arg Asn Met Lys Ala His Ser Gln
                85                  90                  95

Thr Asp Arg Ala Asn Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
        115                 120                 125

Pro Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

```
Asp Met Ala Ala Gln Ile Thr Lys Arg Lys Trp Glu Ala Val His Ala
            165                 170                 175

Ala Glu Gln Arg Arg Val Tyr Leu Glu Gly Arg Cys Val Asp Gly Leu
        180                 185                 190

Arg Arg Tyr Leu Glu Asn Gly Lys Glu Thr Leu Gln Arg Thr Asp Pro
    195                 200                 205

Pro Lys Thr His Met Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Gly Thr Phe Gln Lys Trp Ala Ala Val Val
        260                 265                 270

Val Pro Ser Gly Glu Glu Gln Arg Tyr Thr Cys His Val Gln His Glu
    275                 280                 285

Gly Leu Pro Lys Pro Leu Thr Leu Arg Trp Glu Leu Ser Ser Gln Pro
290                 295                 300

Thr Ile Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Lys Ser
            325                 330                 335

Ser Asp Arg Lys Gly Gly Ser Tyr Thr Gln Ala Ala Ser Ser Asp Ser
        340                 345                 350

Ala Gln Gly Ser Asp Val Ser Leu Thr Ala Cys Lys Val
    355                 360                 365

<210> SEQ ID NO 31
<211> LENGTH: 406
<212> TYPE: PRT
<213> ORGANISM: Homo sapiens

<400> SEQUENCE: 31

Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
            20                  25                  30

Cys Pro Lys Pro Pro Glu Ile Ala His Gly Tyr Val Glu His Ser Val
        35                  40                  45

Arg Tyr Gln Cys Lys Asn Tyr Tyr Lys Leu Arg Thr Glu Gly Asp Gly
    50                  55                  60

Val Tyr Thr Leu Asn Asp Lys Lys Gln Trp Ile Asn Lys Ala Val Gly
65                  70                  75                  80

Asp Lys Leu Pro Glu Cys Glu Ala Asp Asp Gly Cys Pro Lys Pro Pro
            85                  90                  95

Glu Ile Ala His Gly Tyr Val Glu His Ser Val Arg Tyr Gln Cys Lys
        100                 105                 110

Asn Tyr Tyr Lys Leu Arg Thr Glu Gly Asp Gly Val Tyr Thr Leu Asn
    115                 120                 125

Asn Glu Lys Gln Trp Ile Asn Lys Ala Val Gly Asp Lys Leu Pro Glu
130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
            165                 170                 175
```

```
Ala Lys Met Val Ser His His Asn Leu Thr Thr Gly Ala Thr Leu Ile
            180                 185                 190

Asn Glu Gln Trp Leu Leu Thr Thr Ala Lys Asn Leu Phe Leu Asn His
        195                 200                 205

Ser Glu Asn Ala Thr Ala Lys Asp Ile Ala Pro Thr Leu Thr Leu Tyr
        210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Lys Gln Lys Val
            245                 250                 255

Ser Val Asn Glu Arg Val Met Pro Ile Cys Leu Pro Ser Lys Asp Tyr
            260                 265                 270

Ala Glu Val Gly Arg Val Gly Tyr Val Ser Gly Trp Gly Arg Asn Ala
        275                 280                 285

Asn Phe Lys Phe Thr Asp His Leu Lys Tyr Val Met Leu Pro Val Ala
        290                 295                 300

Asp Gln Asp Gln Cys Ile Arg His Tyr Glu Gly Ser Thr Val Pro Glu
305                 310                 315                 320

Lys Lys Thr Pro Lys Ser Pro Val Gly Val Gln Pro Ile Leu Asn Glu
            325                 330                 335

His Thr Phe Cys Ala Gly Met Ser Lys Tyr Gln Glu Asp Thr Cys Tyr
            340                 345                 350

Gly Asp Ala Gly Ser Ala Phe Ala Val His Asp Leu Glu Glu Asp Thr
        355                 360                 365

Trp Tyr Ala Thr Gly Ile Leu Ser Phe Asp Lys Ser Cys Ala Val Ala
        370                 375                 380

Glu Tyr Gly Val Tyr Val Lys Val Thr Ser Ile Gln Asp Trp Val Gln
385                 390                 395                 400

Lys Thr Ile Ala Glu Asn
                405

<210> SEQ ID NO 32
<211> LENGTH: 9
<212> TYPE: PRT
<213> ORGANISM: Homo sapiens

<400> SEQUENCE: 32

Cys Glu Ala Asp Asp Gly Cys Pro Lys
1               5
```

TREATMENT OF CHRONIC OBSTRUCTIVE PULMONARY DISEASE (COPD)

CROSS-REFERENCE TO RELATED APPLICATION

This is a continuation of U.S. application Ser. No. 14/003,120, filed Oct. 7, 2013, which is the U.S. national phase of International Application PCT/US2012/027998, filed Mar. 7, 2012, which claims the benefit of the filing date of U.S. Provisional Patent Application No. 61/449,879, filed Mar. 7, 2011. The entire disclosures of the aforesaid applications are incorporated herein by reference.

REFERENCE TO GOVERNMENT GRANT

The invention described herein was supported in part by the National Institutes of Health, under grant no. 5RC2HL101713-02. The government has certain rights in this invention.

SEQUENCE LISTING

The instant application contains a Sequence Listing which has been submitted in ASCII format via EFS-Web and is hereby incorporated by reference in its entirety. Said ASCII copy, created on Mar. 24, 2016 is named 35926_0417_01_US_540632_SL and is 155,918 bytes in size.

BACKGROUND

Chronic obstructive pulmonary disease (COPD) is a chronic lung disease that is incurable and typically progressive. Chronic bronchitis and emphysema are the predominant examples of COPD. Most people diagnosed with COPD have both chronic bronchitis and emphysema. COPD is a leading cause of death worldwide, and its prevalence is increasing in the industrial countries (see, e.g., Lau et al., 2009, J Cell Physiol. 221:535-543; Devanarayan et al., 2010, COPD 7(1):51-58).

Symptoms of COPD include shortness of breath, chronic persistent coughing, chronic coughing that produces excessive amounts of mucus, chest tightness, and wheezing, among other symptoms. On a tissue level, COPD is characterized by inflammation, cell death and extensive lung tissue remodeling. Genetic markers have been studied as potential markers of early disease and prognosis in COPD. See, e.g., Dahl et al., 2009, Internatl J Chron Obstruct Pulmon Dis. 4:157-167. Changes in serum proteins, such as C-reactive protein (CRP) and surfactant proteins A and D, have been identified in COPD patients. See, for instance, Pinto-Plata et al., 2006, Thorax 61(1):23-28; Epub 2005 Sep. 2 and Lau et al., 2009, supra. To date, these changes in serum proteins have not been useful for predicting COPD susceptibility or severity.

Cigarette smoking is the leading risk factor for developing COPD. Other risk factors include cigar smoke, secondhand smoke and air pollution, as well as long term exposure to an excessive amount of dust, chemical fumes, smoke, gases, vapors or mists. Cigarette smoking has been shown to cause up-regulation in the lungs of proteins associated with the unfolded protein response, including GRP78, catreticulin, PDI and CHOP (Kelsen et al., 2008, Am J Respir Cell Mol Biol. 38:541-550; Tagawa et al., 2008 Free Rad Biol Med. 45:50-59). Other biomarkers have been indicated for COPD. See, e.g., U.S. Publication No. 2008/0044843 and WO 2009/114292. While risk factors are known, there is an on-going need to predict reliably which at-risk individuals will develop COPD. In addition, there is a need to predict reliably which COPD patients will experience rapid loss of lung function.

There is an unmet need for methods for assessing susceptibility to COPD development and to assess severity of disease in a COPD patient. The present disclosure addresses this need.

SUMMARY

The following summary is not an extensive overview. It is intended to neither identify key or critical elements of the various embodiments, not delineate the scope of them.

A method for assessing susceptibility of developing chronic obstructive pulmonary disease (COPD) in a subject at risk for developing COPD is disclosed. The method comprises detecting the presence of or assessing the level of at least one biomarker from the group comprising Lethal (3) malignant brain tumor-like 3 protein (LMBL3); Cathelicidin antimicrobial peptide (CAMP); Contactin-1 (CNTN1); Vascular cell adhesion protein 1 (VCAM1); Interleukin-1 receptor accessory protein (IL1RAP); Dermcidin (DCD); Vitamin K-dependent protein Z (PROZ); Hepatocyte growth factor-like (HGFL); Cell surface glycoprotein (MUC18); 79 kDa glucose-regulated protein (GRP78); Coagulation factor V (FA5); Scavenger receptor cysteine-rich type 1 protein M130 (C163A); Neural cell adhesion molecule (NCAM1); Proteoglycan 4 (PRG4); Procollagen C-endopeptidase enhancer 1 (PCOC1); Plastin-2 OS *Homo sapiens* (PLSL); Coagulation factor XIII A chain (F13A); Fetuin-B (FETUB); Protein 5100-A6 (S10A); Metalloproteinase inhibitor 2 (TIMP2); Peroxiredoxin-1 (PRDX1); Macrophage colony-stimulating factor 1 receptor (CSF1R); Probable G protein coupled receptor 25 (GPR25); Putative zinc-alpha-2-glycoprotein-like 1 (ZAGL1); HLA class I histocompatibility antigen, B-15 alpha chain (1B15); Mannosyl-oligosaccharide 1,2-alpha-mannosidase IA (MA1A1); Myelin P2 (MYP2); Metalloproteinase inhibitor 1 (TIMP1); HLA class I histocompatibility antigen, A-1 alpha chain (1A01); Haptoglobin-alpha isoform 2 (HPT2a); and Haptoglobin-alpha isoform 2 having a post-translational modification (HPT2a-PTM) in the sequence CEADDGCPK (SEQ ID No. 32) comprising at least one of carbamidomethylation of C1, methylation of D4, methylation of D5, and acetylation of K9, in a biological fluid sample obtained from the subject, wherein the biological fluid is selected from peripheral whole blood, serum and plasma. An increased susceptibility of developing COPD is indicated in the at-risk subject if any of the following is determined: a) the presence of one or more of LMBL3, CAMP, CNTN1, VCAM1, IL1RAP, DCD, and PROZ is detected; b) an increased level of one or more of HGFL, MUC18, GRP78, FA5, HPT2a and HPT2a-PTM is assessed, relative to the level of the biomarker in a biological fluid sample from a normal reference; c) a decreased level of one or more of C163A, NCAM1, PRG4, PCOC1, PLSL, F13A, and FETUB is assessed, relative to the level of the biomarker in a biological fluid sample from a normal reference; and/or d) a decreased level of one or more of S10A, TIMP2, PRDX1, CSF1R, GPR25, ZAGL1, 1B15, MA1A1, MYP2, TIMP1, and 1A01 is assessed, relative to the level of the biomarker in a biological fluid sample from a normal reference.

In an embodiment of the method for assessing susceptibility, the biological fluid is plasma or serum.

In an embodiment of the method for assessing susceptibility, the at least one biomarker is selected from HPT2a, GRP78, HGFL, and IL1RAP.

In an embodiment method for assessing susceptibility, at least two or more biomarkers are detected or assessed. In an embodiment, at least one of the at least two biomarker is selected from HPT2a, GRP78, HGFL, and IL1RAP.

In an embodiment of the method for assessing susceptibility, at least three or more biomarkers are detected or assessed. In an embodiment, the at least three or more biomarkers comprise HPT2a, GRP78, HGFL, and IL1RAP.

Also disclosed is a method for assessing severity of COPD in a subject diagnosed with COPD. The method comprises detecting the presence of or assessing the level of a biomarker from the group comprising Lethal (3) malignant brain tumor-like 3 protein (LMBL3); Cathelicidin antimicrobial peptide (CAMP); Contactin-1 (CNTN1); Vascular cell adhesion protein 1 (VCAM1); Interleukin-1 receptor accessory protein (IL1RAP); Dermcidin (DCD); Vitamin K-dependent protein Z (PROZ); Hepatocyte growth factor-like (HGFL); Cell surface glycoprotein (MUC18); 79 kDa glucose-regulated protein (GRP78); Coagulation factor V (FA5); Scavenger receptor cysteine-rich type 1 protein M130 (C163A); Neural cell adhesion molecule (NCAM1); Proteoglycan 4 (PRG4); Procollagen C-endopeptidase enhancer 1 (PCOC1); Plastin-2 OS *Homo sapiens* (PLSL); Coagulation factor XIII A chain (F13A); Fetuin-B (FETUB); Protein 5100-A6 (S10A); Metalloproteinase inhibitor 2 (TIMP2); Peroxiredoxin-1 (PRDX1); Macrophage colony-stimulating factor 1 receptor (CSF1R); Probable G protein coupled receptor 25 (GPR25); Putative zinc-alpha-2-glycoprotein-like 1 (ZAGL1); HLA class I histocompatibility antigen, B-15 alpha chain (1B15); Mannosyl-oligosaccharide 1,2-alpha-mannosidase IA (MA1A1); Myelin P2 (MYP2); Metalloproteinase inhibitor 1 (TIMP1); HLA class I histocompatibility antigen, A-1 alpha chain (1A01); Haptoglobin-alpha isoform 2 (HPT2a); and Haptoglobin-alpha isoform 2 having a post-translational modification in the sequence CEADDGCPK (SEQ ID No. 32) comprising at least one of carbamidomethylation of C1, methylation of D4, methylation of D5, and acetylation of K9, in a biological fluid sample obtained from the subject, wherein the biological fluid is selected from peripheral whole blood, serum and plasma. An increased severity of COPD is indicated in the subject diagnosed with COPD if any of the following is determined: a) the presence of one or more of LMBL3, CAMP, CNTN1, VCAM1, IL1RAP, DCD and PROZ is detected; b) an increased level of one or more of HGFL, MUC18, GRP78, FA5, HPT2a and HPT2a-PTM is assessed, relative to the level of the biomarker in a biological fluid sample from a normal reference; c) a decreased level of one or more of C163A, NCAM1, PRG4, PCOC1, PLSL, F13A, and FETUB is assessed, relative to the level of the biomarker in a biological fluid sample from a normal reference; and/or d) a decreased level of one or more of S10A, TIMP2, PRDX1, CSF1R, GPR25, ZAGL1, 1B15, MA1A1, MYP2, TIMP1, and 1A01 is assessed, relative to the level of the biomarker in a biological fluid sample from a normal reference.

In an embodiment of the method for assessing severity of COPD, the biological fluid is plasma or serum.

In an embodiment of the method for assessing severity of COPD, the at least one biomarker is selected from HPT2a, GRP78, HGFL, and IL1RAP.

In an embodiment method for assessing severity of COPD, at least two or more biomarkers are detected or assessed. In an embodiment, at least one of the at least two biomarker is selected from HPT2a, GRP78, HGFL, and IL1RAP.

In an embodiment of the method for assessing severity of COPD, at least three or more biomarkers are detected or assessed. In an embodiment, the at least three or more biomarkers comprise HPT2a, GRP78, HGFL, and IL1RAP.

A method of monitoring susceptibility of developing COPD in a subject at risk of developing COPD is also provided. The method comprises i) detecting the presence of or assessing the level of a biomarker from the group comprising Lethal (3) malignant brain tumor-like 3 protein (LMBL3); Cathelicidin antimicrobial peptide (CAMP); Contactin-1 (CNTN1); Vascular cell adhesion protein 1 (VCAM1); Interleukin-1 receptor accessory protein (IL1RAP); Dermcidin (DCD); Vitamin K-dependent protein Z (PROZ); Hepatocyte growth factor-like (HGFL); Cell surface glycoprotein (MUC18); 79 kDa glucose-regulated protein (GRP78); Coagulation factor V (FA5); Scavenger receptor cysteine-rich type 1 protein M130 (C163A); Neural cell adhesion molecule (NCAM1); Proteoglycan 4 (PRG4); Procollagen C-endopeptidase enhancer 1 (PCOC1); Plastin-2 OS *Homo sapiens* (PLSL); Coagulation factor XIII A chain (F13A); Fetuin-B (FETUB); Protein S100-A6 (S10A); Metalloproteinase inhibitor 2 (TIMP2); Peroxiredoxin-1 (PRDX1); Macrophage colony-stimulating factor 1 receptor (CSF1R); Probable G protein coupled receptor 25 (GPR25); Putative zinc-alpha-2-glycoprotein-like 1 (ZAGL1); HLA class I histocompatibility antigen, B-15 alpha chain (1B15); Mannosyl-oligosaccharide 1,2-alpha-mannosidase IA (MA1A1); Myelin P2 (MYP2); Metalloproteinase inhibitor 1 (TIMP1); HLA class I histocompatibility antigen, A-1 alpha chain (1A01); Haptoglobin-alpha isoform 2 (HPT2a); and Haptoglobin-alpha isoform 2 having a post-translational modification in the sequence CEADDGCPK (SEQ ID No. 32) comprising at least one of carbamidomethylation of C1, methylation of D4, methylation of D5, and acetylation of K9, in a first biological fluid sample from an at-risk subject diagnosed with COPD obtained at a first time point; ii) detecting the presence of or assessing the level of the biomarker in a second biological fluid sample from the at-risk subject obtained at a second time point; and iii) comparing the level of the biomarker detected or assessed in the first sample to the level of the biomarker detected or assessed in the second sample. An increase in susceptibility of developing COPD is indicated for the at-risk subject is any of the following is determined: a) the presence of one or more of LMBL3, CAMP, CNTN1, VCAM1, IL1RAP, DCD, and PROZ is detected in the second biological fluid sample; b) an increased level of one or more of HGFL, MUC18, GRP78, FA5, HPT2a and HPT2a-PTM is assessed in the second biological sample relative to the level in first biological fluid sample; c) a decreased level of one or more of C163A, NCAM1, PRG4, PCOC1, PLSL, F13A, and FETUB is assessed in the second biological sample relative to the level in first biological fluid sample; and/or d) a decreased level of one or more of S10A, TIMP2, PRDX1, CSF1R, GPR25, ZAGL1, 1B15, MA1A1, MYP2, TIMP1, and 1A01 is assessed in the second biological sample relative to the level in first biological fluid sample.

In an embodiment of the method of monitoring susceptibility of developing COPD, the biological fluid is plasma or serum.

In an embodiment of the method of monitoring susceptibility of developing COPD, the at least one biomarker is selected from HPT2a, GRP78, HGFL, and IL1RAP.

In an embodiment of the method of monitoring susceptibility of developing COPD, at least two or more biomarkers are detected or assessed. In an embodiment, at least one of the at least two biomarker is selected from HPT2a, GRP78, HGFL, and IL1RAP.

In an embodiment of the method of monitoring susceptibility of developing COPD, at least three or more biomarkers are detected or assessed. In an embodiment, the at least three or more biomarkers comprise HPT2a, GRP78, HGFL, and IL1RAP.

Further provided is a method of monitoring the progression of COPD in a subject diagnosed with COPD. The method comprises i) detecting the presence of or assessing the level of a biomarker from the group comprising Lethal (3) malignant brain tumor-like 3 protein (LMBL3); Cathelicidin antimicrobial peptide (CAMP); Contactin-1 (CNTN1); Vascular cell adhesion protein 1 (VCAM1); Interleukin-1 receptor accessory protein (IL1RAP); Dermcidin (DCD); Vitamin K-dependent protein Z (PROZ); Hepatocyte growth factor-like (HGFL); Cell surface glycoprotein (MUC18); 79 kDa glucose-regulated protein (GRP78); Coagulation factor V (FA5); Scavenger receptor cysteine-rich type 1 protein M130 (C163A); Neural cell adhesion molecule (NCAM1); Proteoglycan 4 (PRG4); Procollagen C-endopeptidase enhancer 1 (PCOC1); Plastin-2 OS *Homo sapiens* (PLSL); Coagulation factor XIII A chain (F13A); Fetuin-B (FETUB); Protein S100-A6 (S10A); Metalloproteinase inhibitor 2 (TIMP2); Peroxiredoxin-1 (PRDX1); Macrophage colony-stimulating factor 1 receptor (CSF1R); Probable G protein coupled receptor 25 (GPR25); Putative zinc-alpha-2-glycoprotein-like 1 (ZAGL1); HLA class I histocompatibility antigen, B-15 alpha chain (1B15); Mannosyl-oligosaccharide 1,2-alpha-mannosidase IA (MA1A1); Myelin P2 (MYP2); Metalloproteinase inhibitor 1 (TIMP1); HLA class I histocompatibility antigen, A-1 alpha chain (1A01); Haptoglobin-alpha isoform 2 (HPT2a); and Haptoglobin-alpha isoform 2 having a post-translational modification in the sequence CEADDGCPK (SEQ ID No. 32) comprising at least one of carbamidomethylation of C1, methylation of D4, methylation of D5, and acetylation of K9, in a first biological fluid sample from a subject diagnosed with COPD obtained at a first time point; ii) detecting the presence of or assessing the level of the biomarker in a second biological fluid sample from the subject obtained at a second time point; and iii) comparing the level of the biomarker detected or assessed in the first sample to the level of the biomarker detected or assessed in the second sample. Progression of COPD in the subject is indicated if any of the following is determined: a) the presence of one or more of LMBL3, CAMP, CNTN1, VCAM1, IL1RAP, DCD, and PROZ is detected in the second biological fluid sample; b) an increased level of one or more of HGFL, MUC18, GRP78, FA5, HPT2a and HPT2a-PTM is assessed in the second biological sample relative to the level in first biological fluid sample; c) a decreased level of one or more of C163A, NCAM1, PRG4, PCOC1, PLSL, F13A, and FETUB is assessed in the second biological sample relative to the level in first biological fluid sample; and/or d) a decreased level of one or more of S10A, TIMP2, PRDX1, CSF1R, GPR25, ZAGL1, 1B15, MA1A1, MYP2, TIMP1, and 1A01 is assessed in the second biological sample relative to the level in first biological fluid sample.

In an embodiment of the method of monitoring the progression of COPD in a subject diagnosed with COPD, the biological fluid is plasma or serum.

In an embodiment of the method of monitoring the progression of COPD, the at least one biomarker is selected from HPT2a, GRP78, HGFL, and IL1RAP.

In an embodiment of the method of monitoring the progression of COPD, at least two or more biomarkers are detected or assessed. In an embodiment, at least one of the at least two biomarker is selected from HPT2a, GRP78, HGFL, and IL1RAP.

In an embodiment of the method of monitoring the progression of COPD, at least three or more biomarkers are detected or assessed. In an embodiment, the at least three or more biomarkers comprise HPT2a, GRP78, HGFL, and IL1RAP.

A method for assessing risk of COPD characterized by moderate or severe airway obstruction in a subject diagnosed with COPD is provided. The method comprises assessing the level of a biomarker from the group comprising Hepatocyte growth factor-like (HGFL); 79 kDa glucose-regulated protein (GRP78); and Scavenger receptor cysteine-rich type 1 protein M130 (C163A), in a biological fluid sample obtained from the subject, wherein the biological fluid is selected from peripheral whole blood, serum and plasma. If a) an increased level of one or more of HGFL and GRP78 is assessed, relative to the level of the biomarker in a biological fluid sample from a normal reference; and/or b) a decreased level of C163A is assessed, relative to the level of the biomarker in a biological fluid sample from a normal reference, then increased risk of COPD characterized by moderate or severe airway obstruction is indicated in the subject diagnosed with COPD. In an embodiment, the biological fluid is plasma or serum.

In an embodiment, the greater the increased level of HGFL, the increased level of GRP78, and/or the decreased level of C163A, the greater the risk of COPD characterized by moderate or severe obstruction in the subject diagnosed with COPD.

In an embodiment, the level of GRP78 and the level of HGFL are assessed.

Further provided is a method of monitoring the progression of airway obstruction in a subject diagnosed with COPD. The method comprises i) assessing the level of a biomarker from the group comprising Hepatocyte growth factor-like (HGFL); 79 kDa glucose-regulated protein (GRP78); and Scavenger receptor cysteine-rich type 1 protein M130 (C163A) in a first biological fluid sample from a subject diagnosed with COPD obtained at a first time point, wherein the biological fluid is selected from peripheral whole blood, serum and plasma; ii) assessing the level of the biomarker in a second biological fluid sample from the subject obtained at a second time point; and iii) comparing the level of the biomarker assessed in the first sample to the level of the biomarker detected or assessed in the second sample. If a) an increased level of one or more of HGFL and GRP78 is assessed in the second biological sample relative to the level in first biological fluid sample; and/or b) a decreased level of C163A is assessed in the second biological sample relative to the level in first biological fluid sample, then progression of airway obstruction in the subject is indicated. In an embodiment, the biological fluid is plasma or serum.

In an embodiment, the greater the increased level of HGFL, the increased level of GRP78, and/or the decreased level of C163A, the greater the progression of airway obstruction in the subject diagnosed with COPD.

In an embodiment, the level of GRP78 and the level of HGFL are assessed.

BRIEF DESCRIPTION OF THE DRAWINGS

For the purpose of illustrating the methods disclosed herein, there are depicted in the drawings certain embodiments. However, the methods and related products are not limited to the precise arrangements and instrumentalities of the embodiments depicted in the drawings.

FIGS. 1A and 1B are tables summarizing the phenotypic characteristics of the subjects whose plasma was studied. BMI=body mass index. M=male. C=Caucasian. $FEV_1$=the volume of air forcefully expired during the first second after taking a full breath. FVC=forced vital capacity; the total volume of air expired with maximal force.

FIG. 2 depicts representative images of Western blots of plasma from ex-smokers without COPD ("GOLD 0"; left) and subjects diagnosed with very severe COPD ("GOLD IV"; right), probed with an anti-GRP78 antibody. Blots were quantitated using densitometry and normalized to IgG light chain. The quantitative data are plotted below the Western blot images as box plots, wherein the box represents the interquartile range.

FIGS. 6A and 6B are a series of images of 2-DE gels and a boxplot of the data. FIG. 6A is a series of zoom view images of 2-DE gels for 10 individual samples from GOLD 0 (left panels) and GOLD IV (right panels). The arrow points to haptoglobin-alpha. FIG. 6B is a boxplot of the GOLD 0 and GOLD IV data for haptoglobin-alpha isoform 2, wherein the box represents the interquartile range.

FIGS. 8A-8D depict a series of graphs illustrating % predicted $FEV_1$ as a function of plasma concentration for four individual biomarkers. The biomarkers are: GRP78 (FIG. 8A), C163A (labeled sCD163; FIG. 8B), IL1RAP (labeled IL1AP; FIG. 8C), and HGFL (FIG. 8D). Plasma concentration for GRP78, IL1RAP and HGFL was determined by Western blot; band density of scans was normalized to IgG band density. Plasma concentration for C163A was determined by ELISA.

DEFINITIONS

Figure 3:
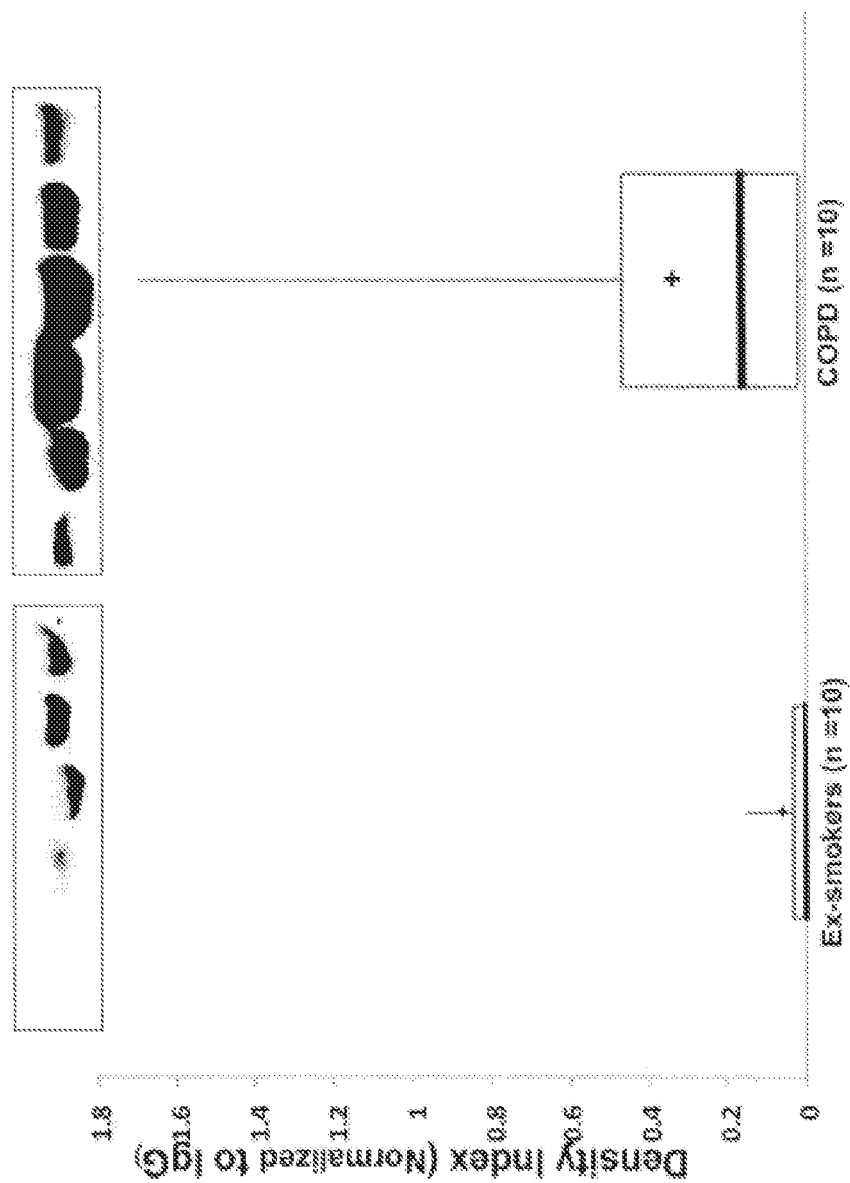
FIG. 3 depicts representative images of Western blots of plasma from GOLD 0 (left) and GOLD IV (right) subjects probed with an anti-IL1RAP antibody. Blots were quantitated using densitometry and normalized to IgG light chain. The quantitative data are plotted below the Western blot images as box plots, wherein the box represents the interquartile range.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20%, more preferably ±10%, more preferably ±5%, even more preferably ±1%, and still more preferably ±0.1%.

As used herein, chronic obstructive pulmonary disease (COPD) refers to a chronic progressive lung disease. Chronic bronchitis and emphysema are non-limiting examples of COPD. COPD can be diagnosed by pulmonary function tests and/or chest X-rays in accordance with accepted clinical practice. Clinically relevant diagnostic tests include: $FEV_1$ (the volume of air forcefully expired during the first second after taking a full breath); forced vital capacity (FVC; the total volume of air expired with maximal force); and flow-volume loops, which are simultaneous spirometric recordings of airflow and volume during forced maximal expiration and inspiration. Reductions of $FEV_1$, FVC, and the ratio of $FEV_1/FVC$ are hallmarks of airflow limitation. See Merck Manual Online for Healthcare Professionals, Pulmonary Disorders, Chronic Obstructive Pulmonary Disorder, Introduction (downloaded from www(dot)merckmanuals(dot)com/professional/sec05/ch049/ch049a (dot)html on 19 Dec. 2010). Severity of disease can be assessed on the same criteria.

GOLD is the abbreviation for the Global Initiative for Chronic Obstructive Lung Disease. GOLD classifications designate the severity of disease for COPD patients as shown in Table 1.

TABLE 1

| GOLD classification | Description | Criteria |
|---|---|---|
| 0 | At-risk of COPD | |
| I | Mild COPD | $FEV_1/FVC < 0.7$ |
| | | $FEV_1 \geq 80\%$ predicted |
| II | Moderate COPD | $FEV_1/FVC < 0.7$ |
| | | $50\% \leq FEV_1 < 80\%$ predicted |
| III | Severe COPD | $FEV_1/FVC < 0.7$ |
| | | $30\% \leq FEV1 < 50\%$ predicted |
| IV | Very severe COPD | $FEV_1/FVC < 0.7$ |
| | | FEV1 < 30% predicted or |
| | | FEV1 < 50% predicted with chronic respiratory failure |

As used herein, "severity of COPD" refers generally to the extent of airflow limitation and optionally to associated symptoms such as chronic coughing and sputum production, as clinically defined parameters. The GOLD classifications are exemplary for classifying COPD severity.

"Increased severity of COPD" is used herein to refer to an increase in airflow limitation (e.g., increased limitation in airflow) and optionally to worsening of associated symptoms such as chronic coughing and sputum production in a COPD patient relative to a normal reference, or relative to the subject at an earlier point in time. An exemplary normal reference can be a non-smoker or an ex-smoker who does not have clinical evidence of COPD, or a population of non-smokers and/or ex-smokers who do not have clinical evidence of COPD. The normal reference can be representative of the patient with regard to approximate age, age group, body-mass index ("BMI"), gender and/or other parameters.

"At risk for developing COPD" refers to a subject having one or more risk factors for COPD. Risk factors known in the art include, but are not limited to, a history of tobacco smoking; long term exposure to one or more of organic dust, inorganic dust, chemical fumes, smoke such as from burning biomass or coal, gases, vapors and mists; and $\alpha_1$-antitrypsin deficiency.

As used herein, the term "subject" or "patient" refers to any animal (e.g., a mammal) including, but not limited to, humans and non-human primates, at risk for developing COPD or diagnosed with COPD. Typically, the terms "subject" and "patient" are used interchangeably herein in reference to a human subject.

As used herein, a "normal subject" or "control subject" refers to a subject that does not manifest clinical symptoms of COPD.

As used herein, a "normal reference" refers to a normal subject or to a population of normal subjects.

"Increased susceptibility of developing COPD" is used herein to refer to an increase in the likelihood or possibility of a subject developing COPD relative to a normal reference, or relative to the subject at an earlier point in time. An exemplary normal reference can be a non-smoker or an ex-smoker who does not have clinical evidence of COPD, or a population of non-smokers and/or ex-smokers who do not have clinical evidence of COPD. The normal reference can be representative of the patient with regard to approximate age, age group, BMI, gender and/or other parameters.

"Delaying development of COPD" as used herein refers to a prolonging of the time to the development of COPD and/or delay in the progression of COPD, i.e., delaying an increase in COPD severity.

"Alleviating COPD," as used herein, refers to a decrease in the severity of COPD, i.e., an increase in lung function, as assessed by conventional clinical methods including, but not limited to spirometry.

As used herein, a "detector molecule" is a molecule that may be used to detect a compound of interest. Non-limiting examples of a detector molecule are molecules that bind specifically to a compound of interest, such as, but not limited to, an antibody, a cognate receptor or binding partner, an aptamer, and a small molecule.

By the term "specifically binds," as used herein with respect to a detector molecule such as an antibody, is meant a detector molecule that recognizes a specific binding partner, such as an antigen, but does not substantially recognize or bind other molecules in a sample. For instance, in a sample containing 79 kDa glucose-regulated protein (GRP78), an antibody that specifically binds to GRP78 does not substantially recognize or bind to other molecules in the sample.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody," as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

As used herein, an "immunoassay" refers to any binding assay that uses an antibody capable of binding specifically to a target molecule to detect and quantify the target molecule.

It is understood that any and all whole or partial integers between any ranges set forth herein are included herein.

DETAILED DESCRIPTION

The methods described herein are based on the discovery that the plasma level of a panel of specific proteins differs between two subject populations: 1) subjects at risk for chronic obstructive pulmonary disease ("COPD") but not manifesting clinical symptoms of COPD; and 2) subjects having very severe COPD. The difference in plasma level is statistically significant for each protein. Each protein can therefore be used as a biomarker in: assessing risk of developing COPD in an at-risk subject; monitoring risk of developing COPD over time in an at-risk subject; assessing severity of disease in a subject diagnosed with COPD ("COPD patient"); monitoring disease progression over time in a COPD patient; and/or monitoring therapeutic efficacy over time in a COPD patient. Each protein may also be a candidate for developing therapeutics designed to modulate plasma level of the protein to approach the level observed for subjects not manifesting clinical symptoms of COPD.

The biomarkers useful in the practice of the methods described herein are proteins selected from the group comprising: Lethal (3) malignant brain tumor-like 3 protein (LMBL3); Cathelicidin antimicrobial peptide (CAMP); Contactin-1 (CNTN1); Vascular cell adhesion protein 1 (VCAM1); Interleukin-1 receptor accessory protein (IL1RAP); Dermcidin (DCD); Vitamin K-dependent protein Z (PROZ); Hepatocyte growth factor-like (HGFL); Cell surface glycoprotein (MUC18); 79 kDa glucose-regulated protein (GRP78); Coagulation factor V (FA5); Scavenger receptor cysteine-rich type 1 protein M130 (C163A); Neural cell adhesion molecule (NCAM1); Proteoglycan 4 (PRG4); Procollagen C-endopeptidase enhancer 1 (PCOC1); Plastin-2 OS *Homo sapiens* (PLSL); Coagulation factor XIII A chain (F13A); Fetuin-B (FETUB); Protein S100-A6 (S10A); Metalloproteinase inhibitor 2 (TIMP2); Peroxiredoxin-1 (PRDX1); Macrophage colony-stimulating factor 1 receptor (CSF1R); Probable G protein coupled receptor 25 (GPR25);

Putative zinc-alpha-2-glycoprotein-like 1 (ZAGL1); HLA class I histocompatibility antigen, B-15 alpha chain (1B15); Mannosyl-oligosaccharide 1,2-alpha-mannosidase IA (MA1A1); Myelin P2 (MYP2); Metalloproteinase inhibitor 1 (TIMP1); HLA class I histocompatibility antigen, A-1 alpha chain (1A01); Haptoglobin-alpha isoform 2 (HPT2a); and HPT2a comprising one or more of four specific post-translational modifications described elsewhere herein (HPT2a-PTM). These proteins can be divided into four categories of expression level: 1) proteins that are present only in subjects having very severe COPD; 2) proteins that are present at a higher level ("up-regulated") in subjects having very severe COPD; 3) proteins that are present at a lower level ("down-regulated") in subjects having very severe COPD; and 4) proteins present only in at-risk subjects not manifesting clinical symptoms of COPD.

The biomarkers were identified in blood plasma prepared from a peripheral blood sample. It is contemplated that the biomarkers will similarly be present in any peripheral blood-derived sample, such as whole blood and blood serum. Therefore, the methods of the invention may be practiced with a biological fluid sample selected from whole blood, plasma and blood serum. The preferred biological fluid sample is plasma.

The proteins discovered to be present in plasma of subjects having very severe COPD but not present in plasma in subjects not manifesting clinical symptoms of COPD are shown in Table 2.

TABLE 2

| Protein Name | Protein ID | SwissProt Accession No. | Seq ID No. |
| --- | --- | --- | --- |
| Lethal (3) malignant brain tumor-like 3 protein | LMBL3 | Q96JM7 | 1 |
| Cathelicidin antimicrobial peptide | CAMP | P49913 | 2 |
| Contactin-1 | CNTN1 | Q12860 | 3 |
| Vascular cell adhesion protein 1 | VCAM1 | P19320 | 4 |
| Interleukin-1 receptor accessory protein | IL1RAP | Q9NPH3 | 5 |
| Dermcidin | DCD | P81605 | 6 |
| Vitamin K-dependent protein Z | PROZ | P22891 | 7 |

If any one or more of LMBL3, CAMP, CNTN1, VCAM1, IL1RAP, DCD, and PROZ is detected in a biological fluid sample from a subject at risk for COPD, the subject is at an elevated susceptibility for developing COPD. If any one or more of LMBL3, CAMP, CNTN1, VCAM1, IL1RAP, DCD, and PROZ is detected in a biological fluid sample from a subject diagnosed with COPD, the subject is likely to have an increased severity of COPD. An increase in expression level in a biological fluid sample of any one or more of LMBL3, CAMP, CNTN1, VCAM1, IL1RAP, DCD, and PROZ over time in a subject with COPD correlates with disease progression. Similarly, decreased expression of any one or more of LMBL3, CAMP, CNTN1, VCAM1, IL1RAP, DCD, and PROZ in a biological fluid sample of a subject with COPD undergoing therapy correlates with an increase in efficacy of the treatment, thereby enabling monitoring of therapeutic efficacy. Expression of these seven biomarkers is not detectable in normal subjects, therefore, decreased expression encompasses a non-detectable level of expression.

The proteins discovered to be present at a higher level ("up-regulated") in plasma of subjects having very severe COPD proteins compared to the level in plasma of subjects not manifesting clinical symptoms of COPD are shown in Table 3.

TABLE 3

| Protein Name | Protein ID | SwissProt Accession No. | Seq ID No. |
| --- | --- | --- | --- |
| Hepatocyte growth factor-like | HGFL | P26927 | 8 |
| Cell surface glycoprotein | MUC18 | P43121 | 9 |
| 79 kDa glucose-regulated protein | GRP78 | P11021 | 10 |
| Coagulation factor V | FA5 | P12259 | 11 |
| Haptoglobin-alpha isoform 2 | HPT2a† | P00738 | 12 |

†This is the protein ID used herein to refer to residues 19-160 of the amino acid sequence of SwissProt Accession No. P00738 (Protein ID HPT2; SEQ ID No. 31).

If any one or more of HGFL, MUC18, GRP78, FA5, and HPT2a is detected at an elevated level in a biological fluid sample from a subject at risk for COPD relative to the level in a normal reference, the subject is at an elevated susceptibility for developing COPD. If any one or more of HGFL, MUC18, GRP78, FA5, and HPT2a is detected at an elevated level in a biological fluid sample from a COPD patient relative to a normal reference, the patient is likely to have an increased severity of COPD. In addition, an increase in expression level in a biological fluid sample of any one or more of HGFL, MUC18, GRP78, FA5, and HPT2a over time in a COPD patient correlates with disease progression. Similarly, decreased expression of any one or more of HGFL, MUC18, GRP78, FA5, and HPT2a in a biological fluid sample of a COPD patient undergoing therapy correlates with an increase in efficacy of the treatment, thereby enabling monitoring of therapeutic efficacy.

It has further been discovered that HPT2a comprises four post-translational modifications (PTMs) in very severe COPD patients that are not present in subjects at risk for COPD. The modifications comprise: carbamidomethylation of the first cysteine, methylation of the two aspartic acids, and acetylation of the lysine in the sequence CEADDGCPK (SEQ ID No. 32). These modified residues correspond to carbamidomethylation of cysteine 68, methylation of aspartic acid 71, methylation of aspartic acid 72, and acetylation of lysine 76 of SEQ ID No. 12. As used herein, "HPT2a-PTM" refers to HPT2a comprising one or more of these post-translational modifications. The detection of HPT2a-PTM in a subject at risk for COPD is indicative of the subject having an elevated susceptibility of developing COPD. If HPT2a-PTM is detected in a biological fluid sample from a COPD patient relative to a normal reference, the patient is likely to have an increased severity of COPD. Detecting an increase in HPT2a-PTM over time in a COPD patient is expected to correlate with disease progression. Likewise, detecting a decrease in HPT2a-PTM in a biological fluid sample of a COPD patient undergoing therapy is expected to correlate with an increase in efficacy of the treatment, thereby enabling monitoring of therapeutic efficacy.

The proteins discovered to be present at a decreased level ("down-regulated") in plasma of subjects having very severe COPD compared to the level in plasma of subjects not manifesting clinical symptoms of COPD are shown in Table 4.

TABLE 4

| Protein Name | Protein ID | SwissProt Accession No. | Seq ID No. |
|---|---|---|---|
| Scavenger receptor cysteine-rich type 1 protein M130 | C163A | Q86VB7 | 13 |
| Neural cell adhesion molecule | NCAM1 | P13591 | 14 |
| Proteoglycan 4 | PRG4 | Q92954 | 15 |
| Procollagen C-endopeptidase enhancer 1 | PCOC1 | Q15133 | 16 |
| Plastin-2 OS Homo sapiens | PLSL | P13796 | 17 |
| Coagulation factor XIII A chain | F13A | P00488 | 18 |
| Fetuin-B | FETUB | Q9UGM5 | 19 |

If any one or more of C163A, NCAM1, PRG4, PCOC1, PLSL, F13A, and FETUB is detected at a decreased level in a biological fluid sample from a subject at risk for COPD relative to the level in a normal reference, the subject is at an elevated susceptibility for developing COPD. If any one or more of C163A, NCAM1, PRG4, PCOC1, PLSL, F13A, and FETUB is detected at a decreased level in a biological fluid sample from a COPD patient relative to a normal reference, the patient is likely to have COPD of increased severity. A decrease in expression level in a biological fluid sample of any one or more of C163A, NCAM1, PRG4, PCOC1, PLSL, F13A, and FETUB over time in a COPD patient correlates with disease progression. Similarly, increased level of any one or more of C163A, NCAM1, PRG4, PCOC1, PLSL, F13A, and FETUB in a biological fluid sample of a COPD patient undergoing therapy correlates with an increase in efficacy of the treatment, thereby enabling monitoring of therapeutic efficacy.

The proteins discovered to be present only in plasma of at-risk subjects not manifesting clinical symptoms of COPD but not present in plasma in subjects having very severe COPD are shown in Table 5.

TABLE 5

| Protein Name | Protein ID | SwissProt Accession No. | Seq ID No. |
|---|---|---|---|
| Protein S100-A6 | S10A | P06703 | 20 |
| Metalloproteinase inhibitor 2 | TIMP2 | P16035 | 21 |
| Peroxiredoxin-1 | PRDX1 | Q06830 | 22 |
| Macrophage colony-stimulating factor 1 receptor | CSF1R | P07333 | 23 |
| Probable G protein coupled receptor 25 | GPR25 | O00155 | 24 |
| Putative zinc-alpha-2-glycoprotein-like 1 | ZAGL1 | A8MT79 | 25 |
| HLA class I histocompatibility antigen, B-15 alpha chain | 1B15 | P30464 | 26 |
| Mannosyl-oligosaccharide 1,2-alpha-mannosidase IA | MA1A1 | P33908 | 27 |
| Myelin P2 | MYP2 | P02689 | 28 |
| Metalloproteinase inhibitor 1 | TIMP1 | P01033 | 29 |
| HLA class I histocompatibility antigen, A-1 alpha chain | 1A01 | P30443 | 30 |

If any one or more of S10A, TIMP2, PRDX1, CSF1R, GPR25, ZAGL1, 1B15, MA1A1, MYP2, TIMP1, and 1A01 is detected at a decreased level in a biological fluid sample from a subject at risk for COPD relative to the level in a normal reference, the subject is at an elevated susceptibility for developing COPD. If any one or more of S10A, TIMP2, PRDX1, CSF1R, GPR25, ZAGL1, 1B15, MA1A1, MYP2, TIMP1, and 1A01 is detected at a decreased level in a biological fluid sample from a COPD patient relative to a normal reference, the patient is likely to have COPD of increased severity. A decrease in expression level in a biological fluid sample of any one or more of S10A, TIMP2, PRDX1, CSF1R, GPR25, ZAGL1, 1B15, MA1A1, MYP2, TIMP1, and 1A01 over time in a COPD patient correlates with disease progression. Similarly, increased level of any one or more of S10A, TIMP2, PRDX1, CSF1R, GPR25, ZAGL1, 1B15, MA1A1, MYP2, TIMP1, and 1A01 in a biological fluid sample of a COPD patient undergoing therapy correlates with an increase in efficacy of the treatment, thereby enabling monitoring of therapeutic efficacy. For this group of biomarkers, decreased levels includes no detectable presence at all of a biomarker in the biological sample, since no detectable presence of these biomarkers was found in COPD patients having very severe COPD.

Exemplary amino acid sequences for the biomarkers are provided in SEQ ID Nos. 1-30. See also Table 11. It is well-known in the art that proteins can exist in a biological sample in a plurality of different forms. These forms can result from either or both of pre- and post-translational modifications. Pre-translationally modified forms include allelic variants, splice variants and RNA editing forms. Post-translationally modified forms include forms resulting from proteolytic cleavage (e.g., cleavage of a signal sequence or fragments of a parent protein), glycosylation, phosphorylation, lipidation, oxidation, methylation, cysteinylation, sulphonation and acetylation.

Thus, in addition to the specific biomarker sequences identified herein by name or accession number, the invention also contemplates the detection in a test sample of naturally-occurring variants that are at least 90%, at least 95%, at least 96%, at least 97%, at least 98%, or at least 99% identical to the exemplified biomarker sequences in SEQ ID Nos. 1-30. Detection of such naturally-occurring variants in a biological fluid sample of a subject may be used in the methods described and claimed.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator "http://blast(dot)ncbi(dot)nlm(dot)nih(dot)gov/Blast(dot)cgi". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAT) can be used.

With regard to HPT2a-PTm, the invention encompasses detection of a post-translational modification at at least one of residues C68, D71, D72 and K76 of SEQ ID No. 12. The post-translation modification for C68 is carbamidomethylation. The post-translation modification for D71 and D72 is methylation; and the post-translational modification for K76 is acetylation. Detection of such modifications can be done by any method known in the art including, but not limited to, mass spectroscopy and immunoassay.

Assessment of Susceptibility of Developing COPD

The invention provides a method of assessing susceptibility of developing COPD in a subject at risk of COPD. The method comprises detecting the presence of or assessing the level of a biomarker in a biological fluid sample obtained from the subject, wherein if: a) the presence of one or more of LMBL3, CAMP, CNTN1, VCAM1, IL1RAP, DCD, and PROZ is detected; b) an increased level of one or more of HGFL, MUC18, GRP78, FA5, HPT2a and HPT2a-PTM is assessed, relative to the level of the same biomarker in the same type of biological fluid sample in a normal reference; c) a decreased level of one or more of C163A, NCAM1, PRG4, PCOC1, PLSL, F13A, and FETUB is assessed, relative to the level of the same biomarker in the same type of biological fluid sample in a normal reference; and/or d) a decreased level of one or more of S10A, TIMP2, PRDX1, CSF1R, GPR25, ZAGL1, 1B15, MA1A1, MYP2, TIMP1, and 1A01 is assessed, relative to the level of the same biomarker in the same type of biological fluid sample in a normal reference; then an increased susceptibility of developing COPD is indicated in the at-risk subject.

In some embodiments of the invention, COPD susceptibility assessment can be determined by comparison of the level of a marker for an at-risk subject to a normal reference, wherein the normal reference is a reference database of levels for that biomarker in normal patients. The reference database can be generated by measuring the same marker under the same conditions in a representative population. Typically the representative population is a population of patients who do not have clinical evidence of COPD. The reference database can be divided into quartiles, wherein the interquartile range is defined by the $25^{th}$ and $75^{th}$ percentile, and has a median. For LMBL3, CAMP, CNTN1, VCAM1, IL1RAP, DCD, PROZ, HGFL, MUC18, GRP78, FA5, HPT2a and HPT2a-PTM, if the test level for the at-risk subject exceeds the interquartile range for the reference database and/or exceeds the median value for the reference database, the conclusion is that the patient has an increased susceptibility for developing COPD. Similarly, for C163A, NCAM1, PRG4, PCOC1, PLSL, F13A, FETUB, S10A, TIMP2, PRDX1, CSF1R, GPR25, ZAGL1, 1B15, MA1A1, MYP2, TIMP1, and 1A01, if the test level for the at-risk subject is less than the interquartile range for the reference database and/or less than the median value for the reference database, the conclusion is that the at-risk subject has an increased susceptibility for developing COPD.

The invention also provides a method of assessing susceptibility of developing COPD in an at-risk subject as a function of time. The method comprises assessing the level of a biomarker in a biological fluid sample at a first point in time to establish a baseline level of the biomarker. The method further comprises assessing the level of the same biomarker at a second point in time in order to identify whether the level of the marker is changing. For a biomarker selected from the group comprising C163A, NCAM1, PRG4, PCOC1, PLSL, F13A, FETUB, S10A, TIMP2, PRDX1, CSF1R, GPR25, ZAGL1, 1B15, MA1A1, MYP2, TIMP1, and 1A01, if the second level is less than the baseline level, it is indicative of an increased susceptibility of developing COPD. For a biomarker selected from the group comprising LMBL3, CAMP, CNTN1, VCAM1, IL1RAP, DCD, PROZ, HGFL, MUC18, GRP78, FA5, HPT2a and HPT2a-PTM, if the second level is greater than the baseline level, it is indicative of an increased susceptibility of developing COPD. The second assessing step is generally performed at least one day after the baseline assessment. It can also be performed multiple days, weeks, months or years after the baseline assessment. Moreover, the second assessing step can be performed iteratively over time to acquire additional data and thereby monitor the risk over an extended period of time. Rate of change in expression levels can be calculated to identify if there is an increasing trend to reduced expression for a biomarker selected from the group comprising C163A, NCAM1, PRG4, PCOC1, PLSL, F13A, FETUB, S10A, TIMP2, PRDX1, CSF1R, GPR25, ZAGL1, 1B15, MA1A1, MYP2, TIMP1, and 1A01, or a increasing trend to increased expression for a biomarker selected from the group comprising LMBL3, CAMP, CNTN1, VCAM1, IL1RAP, DCD, PROZ, HGFL, MUC18, GRP78, FA5, HPT2a and HPT2a-PTM, which would be indicative of an increasing susceptibility to develop COPD.

Assessment of Severity of COPD

The invention also provides a method for assessing severity of COPD in a subject diagnosed with COPD. The method comprises detecting the presence of or assessing the level of a biomarker in a biological fluid sample obtained from the COPD patient, wherein if: a) the presence of one or more of LMBL3, CAMP, CNTN1, VCAM1, IL1RAP, DCD, and PROZ is detected; b) an increased level of one or more of HGFL, MUC18, GRP78, FA5, HPT2a and HPT2a-PTM is assessed, relative to the level of the biomarker in a normal reference; c) a decreased level of one or more of C163A, NCAM1, PRG4, PCOC1, PLSL, F13A, and FETUB is assessed, relative to the level of the biomarker in a normal reference; and/or d) a decreased level of one or more of S10A, TIMP2, PRDX1, CSF1R, GPR25, ZAGL1, 1B15, MA1A1, MYP2, TIMP1, and 1A01 is assessed, relative to the level of the biomarker in a normal reference, then increased severity of COPD is indicated in the COPD patient.

In some embodiments of the invention, severity assessment can be determined by comparison of the level of a biomarker for COPD patient to a normal reference, wherein the normal reference is a reference database of levels for that biomarker in normal subjects. The reference database can be generated as discussed above. Specifically, the reference database can be generated by measuring the same biomarker under the same conditions in a representative population. In an embodiment, the representative population is a population of patients who do not have clinical evidence of COPD. The reference database can be divided into quartiles, wherein the interquartile range is defined by the $25^{th}$ and $75^{th}$ percentile, and has a median. For LMBL3, CAMP, CNTN1, VCAM1, IL1RAP, DCD, PROZ, HGFL, MUC18, GRP78, FA5, HPT2a and HPT2a-PTM, if the test level for the COPD patient exceeds the interquartile range for the reference database and/or exceeds the median value for the reference database, the conclusion is that the patient has an increased severity of COPD. Similarly, for C163A, NCAM1, PRG4, PCOC1, PLSL, F13A, FETUB, S10A, TIMP2, PRDX1, CSF1R, GPR25, ZAGL1, 1B15, MA1A1, MYP2, TIMP1, and 1A01, if the test level for the COPD patient is less than the interquartile range for the reference database for the reference database and/or less than the median value for the reference database, the conclusion is that the patient has an increased severity of COPD.

In another embodiment, assessing severity of COPD in a subject diagnosed with COPD can be determined by comparison of the level of a biomarker for the COPD patient to a reference database of levels for that biomarker in COPD patients, stratified for different clinical degrees of severity of disease.

The invention also provides a method of assessing COPD disease progression in a COPD patient as a function of time. The method comprises assessing the level of a biomarker in a biological fluid sample from the COPD patient at a first point in time to establish a baseline level of the biomarker. The method further comprises assessing the level of the same biomarker in a second biological fluid sample obtained at a second point in time in order to identify whether the level of the biomarker is changing. For a biomarker selected from the group comprising C163A, NCAM1, PRG4, PCOC1, PLSL, F13A, FETUB, S10A, TIMP2, PRDX1, CSF1R, GPR25, ZAGL1, 1B15, MA1A1, MYP2, TIMP1, and 1A01, if the second level is less than the baseline level, it is indicative of disease progression. For a biomarker selected from S10A, TIMP2, PRDX1, CSF1R, GPR25, ZAGL1, 1B15, MA1A1, MYP2, TIMP1, and 1A01, loss of detectable expression can be indicative of very severe COPD. For a biomarker selected from the group comprising LMBL3, CAMP, CNTN1, VCAM1, IL1RAP, DCD, PROZ, HGFL, MUC18, GRP78, FA5, HPT2a and HPT2a-PTM, if the second level is greater than the baseline level, it is indicative of disease progression. The second assessing step is generally performed at least one day after the baseline assessment. It can also be performed multiple days, weeks, months or years after the baseline assessment. Moreover, the second assessing step can be performed iteratively over time to acquire additional data and thereby monitor the disease progression over an extended period of time. Rate of change in expression levels can be calculated to identify if there is an increasing trend to reduced expression for a biomarker selected from the group comprising C163A, NCAM1, PRG4, PCOC1, PLSL, F13A, FETUB, S10A, TIMP2, PRDX1, CSF1R, GPR25, ZAGL1, 1B15, MA1A1, MYP2, TIMP1, and 1A01, or a increasing trend to increased expression for a biomarker selected from the group comprising LMBL3, CAMP, CNTN1, VCAM1, IL1RAP, DCD, PROZ, HGFL, MUC18, GRP78, FA5, HPT2a and HPT2a-PTM, which would be indicative of disease progression.

Assessment of disease progression over time can also be performed while the patient is undergoing treatment with one or more pharmaceutical agents to monitor the likelihood that the treatment is delaying development of COPD or alleviating COPD. As used herein, "pharmaceutical agent" encompasses a single agent or a plurality of agents. In the method of assessing disease progression over time, a baseline level of the biomarker in a biological fluid is assessed while treatment with the one or more pharmaceutical agents is not occurring, such as prior to treatment initiation. After the initiation of treatment, the level of the biomarker ("treatment level") is assessed at at least one later time point. If the treatment level is the same or greater than the baseline level for a biomarker selected from the group comprising C163A, NCAM1, PRG4, PCOC1, PLSL, F13A, FETUB, S10A, TIMP2, PRDX1, CSF1R, GPR25, ZAGL1, 1B15, MA1A1, MYP2, TIMP1, and 1A01, the likelihood increases that development of COPD is delayed by the pharmaceutical agent and/or the pharmaceutical agent is alleviating COPD. For LMBL3, CAMP, CNTN1, VCAM1, IL1RAP, DCD, PROZ, HGFL, MUC18, GRP78, FA5, HPT2a or HPT2a-PTM as the biomarker, if the treatment level is the same or less than the baseline level, the likelihood increases that development of COPD is delayed by the treatment with the pharmaceutical agent and/or the treatment with the pharmaceutical agent is alleviating COPD. The biomarker treatment level can alternatively or additionally be compared to a database of biomarker level measurements in a population not being treated with the pharmaceutical agent to assess whether COPD development is delayed and/or COPD is alleviated. If the biomarker treatment level is greater than an average measurement or range of measurements of the treatment level in the untreated population for a biomarker selected from the group comprising C163A, NCAM1, PRG4, PCOC1, PLSL, F13A, FETUB, S10A, TIMP2, PRDX1, CSF1R, GPR25, ZAGL1, 1B15, MA1A1, MYP2, TIMP1, and 1A01, that is also indicative that of an increased likelihood that COPD development is delayed by the pharmaceutical agent and/or the pharmaceutical agent is alleviating COPD. For LMBL3, CAMP, CNTN1, VCAM1, IL1RAP, DCD, PROZ, HGFL, MUC18, GRP78, FA5 HPT2a or HPT2a-PTM, as the biomarker, if the biomarker treatment level is less than an average measurement or range of measurements of the treatment level in the untreated population, that is also indicative that of an increased likelihood that COPD development is delayed by the pharmaceutical agent and/or the pharmaceutical agent is alleviating COPD. Assessing the level of the biomarker after the initiation of administration of the pharmaceutical agent can be performed iteratively over time to acquire additional data and thereby monitor the treatment efficacy over an extended period of time.

Airway Obstruction in COPD Patients $FEV_1$ is a measure of the degree of airway obstruction. COPD of increasing severity is associated with a lower $FEV_1$. See Table 1. $FEV_1$ is measured and may be converted to a percentage of a normal $FEV_1$, which is based on height, weight and race. The resulting parameter is percent predicted $FEV_1$ ("$FEV_1$ (% predicted)"). For instance, an $FEV_1$ (% predicted) greater than 80% is considered normal (e.g., no or minimal obstruction). An $FEV_1$ (% predicted) of 60% to 79% is indicative of mild obstruction; 40% to 59% is indicative of moderate obstruction; and less than 40% is indicative of severe obstruction.

It has further been discovered that the plasma concentration of three biomarkers, GRP78, C163A and HGFL, is significantly correlated with the percent predicted $FEV_1$ in COPD patients, and that the combination of GRP78 and C163A is a robust predictor of percent predicted FEV1. Accordingly, the invention provides a method of assessing risk of COPD characterized by moderate or severe airway obstruction in a subject diagnosed with COPD. As used herein, "increased risk of COPD characterized by moderate or severe airway obstruction" refers to an increased likelihood that a COPD patient has a percent predicted FEV1 of less than 59%, such as 40% to 59% (moderate obstruction) or less than 40% (severe obstruction). The method comprises assessing the level of a biomarker from the group comprising Hepatocyte growth factor-like (HGFL); 79 kDa glucose-regulated protein (GRP78); and Scavenger receptor cysteine-rich type 1 protein M130 (C163A), in a biological fluid sample obtained from the subject. When a) an increased level of one or more of HGFL and GRP78 is assessed, relative to the level of the biomarker in a biological fluid sample from a normal reference; and/or b) a decreased level of C163A is assessed, relative to the level of the biomarker in a biological fluid sample from a normal reference, then increased risk of COPD characterized by moderate or severe airway obstruction is indicated in the subject diagnosed with COPD. The risk is proportional to the degree of increase (for HGFL and GRP78) and the degree of decrease for C163A. Therefore, the greater the increased level of HGFL, the increased level of GRP78, and/or the decreased level of C163A, the greater the risk of COPD characterized by moderate or severe airway obstruction in the subject diagnosed with COPD.

Airway obstruction in a COPD patient can be monitored as a function of time using the biomarkers. Thus, the invention further provides a method of monitoring the progression of airway obstruction in a subject diagnosed with COPD. As used herein, "progression of airway obstruction" refers to an increase in airway obstruction. The method comprises assessing the level of a biomarker from the group comprising Hepatocyte growth factor-like (HGFL); 79 kDa glucose-regulated protein (GRP78); and Scavenger receptor cysteine-rich type 1 protein M130 (C163A) in a first biological fluid sample from a subject diagnosed with COPD obtained at a first time point. The level of the biomarker is assessed in a second biological fluid sample from the subject obtained at a second time point. The level of the biomarker assessed in the first sample to the level of the biomarker detected or assessed in the second sample. If an increased level of one or more of HGFL and GRP78 is assessed in the second biological sample relative to the level in first biological fluid sample; and/or a decreased level of C163A is assessed in the second biological sample relative to the level in first biological fluid sample, then progression of airway obstruction in the subject is indicated.

In the methods relating to airway obstruction, the biological fluid may be selected from peripheral whole blood, serum and plasma. In a preferred embodiment, the biological sample is plasma. In a preferred embodiment, the levels of both GRP78 and C163A are assessed.

The methods described herein can be practiced using a single biomarker, 2 biomarkers, 3, 4, 5, 6, 7, 8, 9, 10, 11, 12, 13 14, 15, 16, 17, 18, 19, 20, 21, 22, 23, 24, 25, 26, 27, 28, 29 or all 30 biomarkers disclosed herein. In some embodiments, the methods are practiced with at least one of HPT2a, HPT2a-PTM, GRP78, IL1RAP, and HGFL. In some embodiments, the methods are practiced with two of HPT2a, HPT2a-PTM, GRP78, IL1RAP, and HGFL. In some embodiments, the methods are practiced with all of HPT2a, HPT2a-PTM, GRP78, IL1RAP, and HGFL. In an embodiment, the methods are practiced by assessing only HPT2a, HPT2a-PTM, GRP78, IL1RAP, and HGFL. In some embodiments, at least three biomarkers, wherein each biomarker is selected from a different category, as described above. In other embodiments, the methods are practiced with at least two biomarkers selected from the same category, such as GRP78 and HGFL.

The methods of the invention can be practiced with biomarkers comprising or consisting of: HPT2a and IL1RAP; HPT2a and GRP78; HGFL and GRP78; HGFL, IL1RAP and GRP78; HPT2a, HGFL and GRP78; IL1RAP and GRP78; HPT2a, IL1RAP, and GRP78; and HPT2a, HGFL and IL1RAP, and GRP78. In an embodiment, the methods are practiced with biomarkers comprising or consisting of IL1RAP and GRP78. In another embodiment, the methods are practiced with biomarker comprising or consisting of HPT2a, IL1RAP and GRP78. In yet another embodiment, the methods are practiced with biomarkers comprising or consisting of HGFL, HPT2a, IL1RAP and GRP78.

The methods described herein rely on assessing the level of a biomarker, whose level correlates in a statistically significant manner with susceptibility to and severity of COPD, in a sample of a biological fluid obtained from the patient. The biological fluid can be selected from peripheral whole blood, and components thereof such as blood serum ("serum") and blood plasma ("plasma"). In preferred embodiments, the biological fluid is plasma. The biological fluid is obtained from the subject using conventional methods in the art. For instance, one skilled in the art knows how to draw blood and how to process it in order to obtain serum and/or plasma for use in practicing the described methods. Generally speaking, the method of obtaining and storing, if necessary, the biological fluid sample preferably maintains the integrity of the one or more biomarkers of the disclosed herein such that it can be accurately quantified in the biological fluid sample.

The methods of the invention include quantitatively measuring the level of a protein biomarker. Methods of quantitatively assessing the level of a protein in a biological fluid such as plasma are well known in the art. In some embodiments, assessing the level of a protein involves the use of a detector molecule for the biomarker. Detector molecules can be obtained from commercial vendors or can be prepared using conventional methods in the art. Exemplary detector molecules include, but are not limited to, an antibody that binds specifically to the biomarker, a naturally-occurring cognate receptor, or functional domain thereof, for the biomarker, an aptamer that binds specifically to the biomarker, and a small molecule that binds specifically to the biomarker. Small molecules that bind specifically to a biomarker can be identified using conventional methods in the art, for instance, screening of compounds using combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. Methods for preparing aptamers are also well-known in the art.

In a preferred embodiment, the level of a biomarker is assessed using an antibody. Thus, exemplary methods for assessing the level of a biomarker in a biological fluid sample include various immunoassays, for example, immunohistochemistry assays, immunocytochemistry assays, ELISA, capture ELISA, sandwich assays, enzyme immunoassay, radioimmunoassay, fluorescence immunoassay, and the like, all of which are known to those of skill in the art. See e.g. Harlow et al., 1988, Antibodies: A Laboratory Manual, Cold Spring Harbor, N.Y.; Harlow et al., 1999, Using Antibodies: A Laboratory Manual, Cold Spring Harbor Laboratory Press, NY. Solid phase immunoassays can be particularly useful. Where two or more biomarkers are assessed, a panel of antibodies in an array format can be utilized. Custom antibody microarrays or chips can be obtained commercially.

The generation of polyclonal antibodies is accomplished by inoculating the desired animal with an antigen and isolating antibodies which specifically bind the antigen therefrom.

Monoclonal antibodies directed against one biomarkers identified herein may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Human monoclonal antibodies may be prepared by the method described in U.S. patent publication 2003/0224490. Monoclonal antibodies directed against a biomarker such as GRP78 can be generated, for instance, from mice immunized with the biomarker using standard procedures as referenced herein.

For use in preparing an antibody, a biomarker may be purified from a biological source that endogenously comprises the biomarker, or from a biological source recombinantly-engineered to produce or over-produce the biomarker, using conventional methods known in the art. Exemplary protein sequences for the biomarkers are provided as SEQ ID Nos. 1-30. Exemplary nucleic acid for the biomarkers described herein are readily available in public sequence databases, such as National Library of Medicine's genetic sequence database GenBank® (Benson et al., 2008, *Nucleic Acids Research*, 36 (Database issue):D25-30).

Nucleic acid encoding the monoclonal antibody obtained using the procedures described herein may be cloned and sequenced using technology which is available in the art, and is described, for example, in Wright et al. (1992, Critical Rev. Immunol. 12 (3,4):125-168) and the references cited therein.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory Press, Cold Spring Harbor, N.Y.).

Bacteriophage which encode the desired antibody may be engineered such that the protein is displayed on the surface thereof in such a manner that it is available for binding to the antigen against which the antibody is directed. Thus, when bacteriophage which express a specific antibody are incubated in the presence of the antigen, for instance, antigen immobilized on a resin or surface, the bacteriophage will bind to the antigen. Bacteriophage which do not express the antibody will not bind to the antigen. Such panning techniques are well known in the art and are described for example, in Wright et al., (supra). Processes, such as those described above, have also been developed for the production of human antibodies using M13 bacteriophage display (Burton et al., 1994, Adv. Immunol. 57:191-280).

The procedures just presented describe the generation of phage which encode the Fab portion of an antibody molecule. However, phage which encode single chain antibodies (scFv/phage antibody libraries) are also useful in preparing Fab molecules useful in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA. Synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105) may also be used to prepare an antibody useful in the practice of the invention.

Other methods for assessing the level of a protein include chromatography (e.g., HPLC, gas chromatography, liquid chromatography) and mass spectrometry (e.g., MS, MS-MS). For instance, a chromatography medium comprising a cognate receptor for the biomarker, an aptamer that binds specifically to the biomarker, or a small molecule that binds specifically to the biomarker can be used to substantially isolate the biomarker from the sample of biological fluid.

The level of substantially isolated protein can be quantitated directly or indirectly using a conventional technique in the art such as spectrometry, Bradford protein assay, Lowry protein assay, biuret protein assay, or bicinchoninic acid protein assay, as well as immunodetection methods.

The level of a biomarker in a biological fluid sample can be normalized. For instance, the level can be normalized to another component of the fluid sample, whose level is independent of COPD susceptibility or disease severity. It is well within the skill of the skilled artisan to select a suitable component for normalization. An exemplary, but non-limiting, component for normalization is the IgG light chain.

Method of Treatment

The invention further provides a method for treatment of COPD. It is believed that GRP78 provides a protective effect in lung tissue (see, e.g., Kelsen et al, 2008, supra). As demonstrated herein, GRP78 is elevated in plasma of COPD patients having very severe COPD, but not in subjects that do not manifest clinical symptoms of COPD. These data suggest that in lung tissue of COPD patients, GRP78 is secreted or otherwise released from lung tissue, thereby reducing the protective effect of GRP78. Accordingly, the method for treatment of COPD comprises administering to the COPD patient one or more pharmaceutical agents that promote expression of GRP78 in lung tissue of the COPD patient. Drugs that promote expression of GRP78 are known in the art and include, but are not limited to, tunicamycin and thapsigargin. See Hara et al., 2010, Neurochem Int. 2011 January; 58(1):35-43. Epub 2010 Oct. 23.

Kits

A kit is envisaged for practicing every method disclosed herein. The following is a description of a kit useful for assessing susceptibility of developing COPD in an at-risk subject or assessing COPD severity in a COPD patient by measuring the level of a biomarker in a biological fluid. The description is not intended to be limiting and should not be construed that way.

Kits can comprise a detector molecule that binds to a biomarker of the invention. For example, the kit can comprise an antibody, an antibody derivative, or an antibody fragment that binds specifically with a biomarker protein of the invention. The kit may alternatively comprise an aptamer or small molecule that binds specifically to a biomarker of the invention. Preferably, the biomarker is selected from GRP78, HGFL, and IL1RAP. Such kits may also comprise a plurality of antibodies, antibody derivatives, or antibody fragments wherein the plurality of such antibody agents binds specifically with a biomarker protein, or a fragment of the biomarker protein.

For antibody-based kits, the kit can comprise, for example: (1) a first antibody (e.g., attached to a solid support) that binds to a biomarker; and, optionally, (2) a second, different antibody that binds to either the protein or the first antibody and is conjugated to a detectable label.

The kit can further comprise components necessary for detecting the detectable label (e.g., an enzyme or a substrate). Optionally, the kit comprises at least one negative control containing a biomarker at a concentration of about the concentration of the biomarker which is present in a biological fluid sample of a normal subject. Optionally, the kit also includes at least one positive control containing the biomarker at a concentration of about the concentration of the biomarker which is present in a biological fluid sample of a COPD patient having very severe COPD.

Furthermore, the kit can optionally include instructional material for use of the kit in the assessment of COPD susceptibility or COPD severity. Such instructions may comprise instructions to: detect the presence of or assess the level of at least one biomarker from the group comprising Lethal (3) malignant brain tumor-like 3 protein (LMBL3); Cathelicidin antimicrobial peptide (CAMP); Contactin-1 (CNTN1); Vascular cell adhesion protein 1 (VCAM1); Interleukin-1 receptor accessory protein (IL1RAP); Dermcidin (DCD); Vitamin K-dependent protein Z (PROZ); Hepatocyte growth factor-like (HGFL); Cell surface glycoprotein (MUC18); 79 kDa glucose-regulated protein (GRP78); Coagulation factor V (FA5); Scavenger receptor cysteine-rich type 1 protein M130 (C163A); Neural cell adhesion molecule (NCAM1); Proteoglycan 4 (PRG4); Procollagen C-endopeptidase enhancer 1 (PCOC1); Plastin-2 OS *Homo sapiens* (PLSL); Coagulation factor XIII A chain (F13A); Fetuin-B (FETUB); Protein S100-A6 (S10A); Metalloproteinase inhibitor 2 (TIMP2); Peroxiredoxin-1 (PRDX1); Macrophage colony-stimulating factor 1 receptor (CSF1R); Probable G protein coupled receptor 25 (GPR25); Putative zinc-alpha-2-glycoprotein-like 1 (ZAGL1); HLA class I histocompatibility antigen, B-15 alpha chain (1B15); Mannosyl-oligosaccharide 1,2-alpha-mannosidase IA (MA1A1); Myelin P2 (MYP2); Metalloproteinase inhibitor 1 (TIMP1); HLA class I histocompatibility antigen, A-1 alpha chain (1A01); Haptoglobin-alpha isoform 2 (HPT2a); and HPT2a comprising one or more of four specific post-translational modifications as described herein (HPT2a-PTM), in a biological fluid sample obtained from a subject at risk of COPD or a subject diagnosed with COPD, wherein if: a) the presence of one or more of LMBL3, CAMP, CNTN1, VCAM1, IL1RAP, DCD, and PROZ is detected; b) an increased level of one or more of HGFL, MUC18, GRP78, FA5, HPT2a, and HPT2a-PTM is assessed, relative to the level of the biomarker in a biological fluid sample from a normal reference; c) a decreased level of one or more of C163A, NCAM1, PRG4, PCOC1, PLSL, F13A, and FETUB is assessed, relative to the level of the biomarker in a biological fluid sample from a normal reference; and/or d) a decreased level of one or more of S10A, TIMP2, PRDX1, CSF1R, GPR25, ZAGL1, 1B15, MA1A1, MYP2, TIMP1, and 1A01 is assessed, relative to the level of the biomarker in a biological fluid sample from a normal reference; then an increased susceptibility of developing COPD is indicated in the at-risk subject or an increased severity of COPD is indicated in the subject diagnosed with COPD.

The instructional material may comprise a publication, a recording, a diagram, or any other medium of expression which can be used to communicate the usefulness of the method of the invention in the kit for assessment of susceptibility or COPD severity in a subject. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

The kit may optionally further include at least one sample container for containing a biological fluid sample obtained from the mammal Kits for practice of the invention may also comprise, e.g., buffering agents, preservatives, or protein stabilizing agents. Each component of the kit can be enclosed within an individual container and all of the various containers can be within a single package, along with instructions for interpreting the results of the assays performed using the kit.

EXAMPLE

The methods and kits are further described in detail by reference to the following experimental example. The example is provided for purposes of illustration only, and is not intended to be limiting unless otherwise specified. Thus, the methods and kits should in no way be construed as being limited to the following example, but rather, should be construed to encompass any and all variations which become evident as a result of the teaching provided herein.

Study Subjects:

The plasma samples were obtained from subjects enrolled in the COPDGene® project. By design, plasma samples used in the present disclosure came from subjects similar in age, smoking history and duration of smoking cessation. Accordingly, plasma samples used in the present disclosure were obtained from phenotypically well-characterized ex-cigarette smokers 45 years of age or older with a >10 pack year exposure history. Also by design, subjects differed significantly by FEV1 and FEV1/FVC and extent of emphysema ($p<0.01$ for each). The following phenotypic characteristics were used to characterize subjects: spirometry, diffusion capacity, extent of emphysema (determined by chest CT scan), age, gender, ethnicity, height/weight, body mass index, 6 minute walk distance, and co-morbidities. Plasma samples from two groups of 10 subjects each were used in the present disclosure. A first group ("GOLD IV") consisted of subjects with very severe COPD. See FIG. 1B. The second group ("GOLD 0") consisted of subjects of ex-smokers without COPD (i.e., normal lung function). See FIG. 1A. Subjects in GOLD 0 had normal spirometry and no emphysema, in contrast to subjects in GOLD IV.

GOLD is the abbreviation for the Global Initiative for Chronic Obstructive Lung Disease. GOLD classifications designate the severity of disease for COPD patients.

A. Materials and Methods

Blood Collection:

plasma samples were obtained at the time of enrollment in the COPDGene® project. In order to optimize sample quality (i.e., minimal hemolysis and proteolysis), VACUTAINER P100 blood collection system (Beckton Dickenson, P100, Franklin Lakes, N.J.), specifically made for proteomic studies was employed. Each P100 tube can hold 7-8 mL of whole blood. Blood samples were centrifuged at room temperature within 30 minutes of collection, and the plasma aliquoted into freezer vials (500 microliter each) and stored at −80° C. until used.

Sample hemolysis was assessed from the hemoglobin concentration as determined spectrometrically. A standard hemoglobin concentration curve was constructed using a serial dilution of lysed red blood cells (RBCs). Plasma samples of each subject in both groups demonstrated similar, minimal degrees of hemolysis (less than 0.1% for each subject).

Immunodepletion of Plasma:

Plasma samples in a group were pooled together and subjected to one of two immunodepletions protocols. In one protocol, samples were immunodepleted to remove albumin and immunoglobulin by Q-proteome spin column (Qproteome Albumin/IgG Depletion Kit, Qiagen, Carson City, Calif.) in accordance with the manufacturer's instructions.

In a second protocol, samples were depleted for the 12 most abundant plasma proteins and the approximately 50 moderately abundant plasma proteins using a sequential, antibody-affinity double resin column approach in which each resin column contained a different set of bound antibodies (IgY14 spin columns and Supermix immunoaffinity chromatography columns, Sigma Inc., St. Louis, Mo.) in accordance with the manufacturer's instructions.

An aliquot of 500 microliter of pooled plasma was diluted to 2.50 milliliter (mL) in dilution buffer, filtered through a 0.45 micron spin filter and then loaded into a 5 mL column Diluted plasma samples were injected into the liquid chromatography column as 10 separate, 230 microliter injections. The eluent for each 230 microliter injection was collected from 5.00 to 19.00 min, resulting in ~6.5 mL of immunodepleted plasma for each injection, for a total of about 65 mL diluted, immunodepleted plasma. The immunodepleted sample was immediately frozen at −80° C. Subsequently, the 65 ml of diluted, immunodepleted plasma for each group was thawed and concentrated down to 1 mL using a NANOSEP 3K spin column (Pall, Ann Arbor, Mass.) per manufacturer's protocol.

The Human IgY14 resin and Human Supermix resin antibody affinity column method of immunodepletion was more effective than the Qproteome spin column method in removing albumin and immunoglobulins. However, for both methods, the extent of immunodepletion was similar in the two study groups.

Protein Separation (1D):

Pooled samples were analyzed by gel electrophoresis-liquid chromatography mass spectroscopy (GeLC-MS) as follows.

Each of the pooled GOLD 0 and GOLD IV immunodepleted samples was diluted at a 1:2 ratio with Laemmli sample buffer (BioRad, Hercules, Calif.) containing 5% β-mercaptoethanol, heated for 10 minutes at 90° C. and loaded onto a 10-14% polyacrylamide gel. Electrophoresis was performed using a mini Protean II system (BioRad) at 200 V for 45 minutes. Separation was confirmed by staining with SimplyBlue SafeStain (Invitrogen). Each sample lanes was sliced into 20 sections, and each section further cut into ~1 mm$^3$ pieces in preparation for tryptic digestion.

Tryptic Digestion:

The resulting gel pieces were treated with 10 mM DTT in 50 mM ammonium bicarbonate for 30 min at 37° C., and the proteins were then alkylated with 50 mM iodoacetamide in 50 mM ammonium bicarbonate for 30 minutes at room temperature in the dark. After treatment with 50% (v/v) acetonitrile in 50 mM bicarbonate, and dehydration with pure acetonitrile, approximately 40 microliter of trypsin (12.5 microgram/microliter in 50 mM ammonium bicarbonate solution) was added to cover the gel pieces. Trypsin digestion, peptide extraction, and sample cleanup with desalting ZIPTIPS (Millipore, Billerica, Mass.) were performed as described (Duan et al., 2008, J Proteome Res. 7(11): 2438-2444).

2-DE Gel Separation and Image Analysis:

2-DE gel separation was used to study pooled samples immunodepleted by the Qproteome depletion method. The 2-DE gel separation and image analysis system employed was described previously (Kelsen et al, 2008, supra). In brief, the first dimension of separation was isoelectric focusing (IEF), which used narrow range IPG strips (pI 4-7 and 6-10). The second dimension of separation was SDS polyacrylamide gel electrophoresis. Proteins in the 2-DE gel were revealed by staining with SYPRO-Ruby fluorescent total protein stain (Molecular Probes, Eugene, Oreg.). Fluorescence images were captured and analyzed, and individual spot volumes were calculated by density/area integration and normalized for slight difference in protein loading across gels.

Protein spots were excised from the 2-DE gel and subjected to tryptic digestion as described in Kelsen et al. (2008, supra) and in Boden and Merali (2011, Methods Enzymol. 2011; 489:67-82).

Identification of Differentially Expressed Proteins:

The desalted tryptic peptides were dried in a vacuum centrifuge and resolubilized in 30 microliter of 0.1% (vol/vol) trifluoroacetic acid. The tryptic peptide sample was loaded onto a 2 microgram capacity peptide trap (Cap-Trap™; Michrom Bioresources, Auburn, Calif.), separated by a C18 capillary column (15 cm 75 μm, Agilent) at 300 nl/min (delivered by an Agilent 1100 LC pump). A mobile-phase gradient was run using mobile phase A (1% acetonitrile/0.1% formic acid) and B (80% acetonitrile/0.1% formic acid) from 0 to 10 min with 0-15% B followed by 10-60 min with 15-60% B and 60-65 min with 60-100% B.

Nanoelectrospray ionization (ESI) tandem MS was performed using a HCT Ultra ion trap mass spectrometer (Bruker). ESI was delivered using a distal-coating spray Silica tip (ID 20 μM, tip inner ID 10 μM, New Objective) at a spray voltage of −1300 V. Using an automatic switching between MS and MS/MS modes, MS/MS fragmentation was performed on the two most abundant ions on each spectrum using collision-induced dissociation with active exclusion (excluded after two spectra, and released after 2 min) The complete system was fully controlled by HyStar 3.1 software.

Mass spectra (MS) processing was performed using Brukers Biotools (Version 2.3.0.0) with search and quantitation toolbox options. The generated de-isotoped peak list was submitted to an in-house Mascot server 2.2 for searching against the Swiss-Prot database (version 56.6 of 16 Dec. 2008, 405506 sequences). Mascot search parameters were set as follows: Homo sapiens (20413 sequences); enzyme, trypsin with maximal 1 missed cleavage; fixed modification, cysteine carbamidomethylation; variable modification, methionine oxidation; 0.50 Da mass tolerance for precursor peptide ions; and 0.6 Da for MS/MS fragment ions. All peptide matches were filtered using an ion score cutoff of 10. The following two criteria were used to evaluate protein identification: one peptide with ion score ≥35, two or more peptides with at least one ion score ≥20 (p<0.05 threshhold) and the cumulative Mascot scores ≥35; for all the proteins with cumulative MOWSE scores ≥20 and ≤35, the theoretical and experimental gel molecular weights had to be consistent. When these criteria were used to search against a reversed decoy Swiss-Prot database, there was no false positive match (false discovery <0.5%). For added stringency, proteins with scores above 40 were used for comparisons between samples.

Quantification of Differentially Expressed Proteins:

Mascot Distiller based label-free quantitation was used to determine the relative abundance of each identified protein in a given sample. This is quantitation based on the search results and the relative intensities of extracted ion chromatograms for precursors in both GOLD 0 and GOLD IV, aligned using mass and elution time. Distiller takes the list of peptides returned by the Mascot search and looks for the precursors in each of the survey scans. In most cases, the majority of proteins are unchanged and only a small number are significantly different.

A combination of peptide number, emPAI, sequence coverage and modified peptide counting, APEX, was also used to find out the relative abundance and determine whether given protein was differentially expressed in the COPD group relative to control; that is, either increased or decreased relative expression. Ratios whose p value was <0.05 as provided by the APEX software were accepted as statistically significantly different.

Western Blot Analysis:

Proteins (30 to 80 micrograms) from the lysates as used for the 2-DE gels were separated by 10-14% gradient SDS-PAGE. The separated proteins were transferred to a nitrocellulose membrane in a semi-dry blotting chamber according to the manufacturer's protocol (Biorad, Hercules, Calif.). Blots were blocked with 5% milk in Tris-buffer saline solution (pH 7.6) containing 0.05% Tween-20 (TBS/T), and probed with the following rabbit anti-human antibodies from Santa Cruz Biotechnology (Santa Cruz, Calif.) at a concentration of 0.4 µg/mL: GRP78, IL1RAP and HGFL. Blots were incubated with primary antibody overnight at 4° C. at with gentle shaking and then incubated with a mouse anti-rabbit HRP-conjugated secondary Ab (1:10000) (Biomeda Corp Foster City, Calif.) for 1 hr at room temperature.

Blots were exposed using a chemiluminescent detection method (Enhanced ECL Detection System, Amersham Biosciences). Gels were scanned by FLA 5100 (FujiFilm, Edison, N.J.) and the density of bands observed was determined using NIH free-ware (ImageJ software).

Statistics:

Western blots for proteins of interest were scanned and differences in band density assessed statistically by Students' t-test. Statistical significance was accepted at the $p<0.05$ level.

ROC Curves:

Log-ratio data were used to construct receiver operating characteristic (ROC) curves for some of the biomarkers. Since both classes, GOLD O and GOLD IV, were very small for these data, random sampling could introduce random effects that could be too big to ignore. In order to improve AUC, leave-one-out cross-validation was performed to balance the training sets by oversampling. Oversampling means that sample replicates are drawn randomly from one of the classes such that the size of that class increases. Oversampling was performed in both classes as follows. If the data comprise 11 GOLD 0 samples and 14 GOLD IV samples, then for each GOLD 0 sample, 13 replicates were added (to increase the number to 14). For each GOLD IV, 10 replicates were added (to increase number to 11). In the obtained set, both classes had the same number of samples (14*11), and any two samples from the same class had the same number of replicates.

B. Results

GeLC-MS analysis of pooled plasma samples revealed four groups of proteins having difference in expression when comparing GOLD IV to GOLD 0. The first protein group consisted of proteins whose expression level was greater ("up regulated") in GOLD IV plasma compared to the level in GOLD 0 plasma. The data for these proteins are summarized in Table 6.

TABLE 6

| Protein Name | Protein ID | Molecular Weight | MOWSE score ratio | Peptides Ratio GOLD IV/GOLD 0 | Sequence coverage ratio | emPAI Ratio |
|---|---|---|---|---|---|---|
| Hepatocyte growth factor-like | HGFL | 80268 | 1.81 | 1.90 | 1.93 | 2.16 |
| Cell surface glycoprotein | MUC18 | 71563 | 2.7 | 3 | 2.4 | 3.5 |
| 79 kDa glucose-regulated protein | GRP78 | 72288 | 2.76 | 2 | 2.3 | 2.25 |
| Coagulation factor V | FA5 | 251514 | 3.6 | 4 | 5 | 4 |

The second protein group consisted of proteins that were exclusively expressed in GOLD IV plasma compared to GOLD 0 plasma. The data for the proteins in this group are summarized in Table 7.

TABLE 7

| Protein Name | Protein ID | Molecular Weight | MOWSE score ratio | Peptides Ratio GOLD IV/GOLD 0 | Sequence coverage ratio | emPAI Ratio |
|---|---|---|---|---|---|---|
| Lethal (3) malignant brain tumor-like 3 protein | LMBL3 | 88280 | 82 | 2 | 3 | 0.04 |

TABLE 7-continued

| Protein Name | Protein ID | Molecular Weight | MOWSE score ratio | Peptides Ratio GOLD IV/GOLD 0 | Sequence coverage ratio | emPAI Ratio |
|---|---|---|---|---|---|---|
| Cathelicidin antimicrobial peptide | CAMP | 19289 | 112 | 2 | 10 | 0.36 |
| Contactin-1 | CNTN1 | 113249 | 112 | 3 | 4.3 | 0.03 |
| Vascular cell adhesion protein 1 | VCAM1 | 81224 | 120 | 3 | 4.5 | 0.08 |
| Interleukin-1 receptor accessory protein | IL1RAP | 65377 | 145 | 5 | 7 | 0.10 |
| Dermcidin | DCD | 11277 | 70 | 1 | 10 | 0.08 |
| Vitamin K-dependent protein Z | PROZ | 44715 | 197 | 6 | 16.5 | 0.46 |

The third protein group consisted of proteins whose expression level was decreased ("down regulated") in GOLD IV plasma compared to the level in GOLD 0 plasma. The data for these proteins are summarized in Table 8.

TABLE 8

| Protein Name | Protein ID | Molecular Weight | MOWSE score ratio | Peptides Ratio GOLD IV/GOLD 0 | Sequence coverage ratio | emPAI Ratio |
|---|---|---|---|---|---|---|
| Scavenger receptor cysteine-rich type 1 protein M130 | C163A | 125355 | 0.37 | 0.25 | 0.25 | 0.25 |
| Neural cell adhesion molecule | NCAM1 | 94515 | 0.45 | 0.67 | 0.56 | 0.429 |
| Proteoglycan 4 | PRG4 | 150984 | 0.50 | 0.50 | 0.51 | 0.53 |
| Procollagen C-endopeptidase enhancer 1 | PCOC1 | 47942 | 0.56 | 0.5 | 0.59 | 0.583 |
| Plastin-2 OS Homo sapiens | PLSL | 70245 | 0.57 | 0.57 | 0.89 | 0.74 |
| Coagulation factor XIII A chain | F13A | 83215 | 0.60 | 0.33 | 0.36 | 0.429 |
| Fetuin-B | FETUB | 42028 | 0.65 | 0.31 | 0.54 | 0.589 |

The fourth protein group consisted of proteins that were exclusively expressed in GOLD 0 plasma compared to GOLD IV plasma. The data for these proteins are summarized in Table 9.

TABLE 9

| Protein Name | Protein ID | Molecular Weight | MOWSE score ratio | Peptides Ratio GOLD IV/GOLD 0 | Sequence coverage ratio | emPAI Ratio |
|---|---|---|---|---|---|---|
| Protein S100-A6 | S10A | 10173 | 57 | 2 | 16.7 | 0.32 |
| Metalloproteinase inhibitor 2 | TIMP2 | 24383 | 63 | 1 | 6.4 | 0.13 |
| Peroxiredoxin-1 | PRDX1 | 22096 | 64 | 2 | 10.6 | 0.31 |
| Macrophage colony-stimulating factor 1 receptor | CSF1R | 107915 | 76 | 2 | 3.7 | 0.03 |
| Probable G protein coupled receptor 25 | GPR25 | 38799 | 35 | 2 | 3.2 | 0.02 |
| Putative zinc-alpha-2-glycoprotein-like 1 | ZAGL1 | 22965 | 87 | 3 | 13.2 | 0.30 |
| HLA class I histocompatibility antigen, B-15 alpha chain | 1B15 | 40363 | 90 | 3 | 10.8 | 0.08 |
| Mannosyl-oligosaccharide 1,2-alpha-mannosidase IA | MA1A1 | 72922 | 107 | 4 | 5.8 | 0.09 |

TABLE 9-continued

| Protein Name | Protein ID | Molecular Weight | MOWSE score ratio | Peptides Ratio GOLD IV/GOLD 0 | Sequence coverage ratio | emPAI Ratio |
|---|---|---|---|---|---|---|
| Myelin P2 | MYP2 | 14900 | 112 | 2 | 13.6 | 0.48 |
| Metalloproteinase inhibitor 1 | TIMP1 | 23156 | 138 | 4 | 32.4 | 0.47 |
| HLA class I histocompatibility antigen, A-1 alpha chain | 1A01 | 40820 | 142 | 3 | 14 | 0.16 |

The results of the proteomic analysis were validated by subjecting 10 individual samples from each GOLD group to Western blot analysis. Bands were scanned densiometrically and normalized to IgG light chain.

Figure 4:
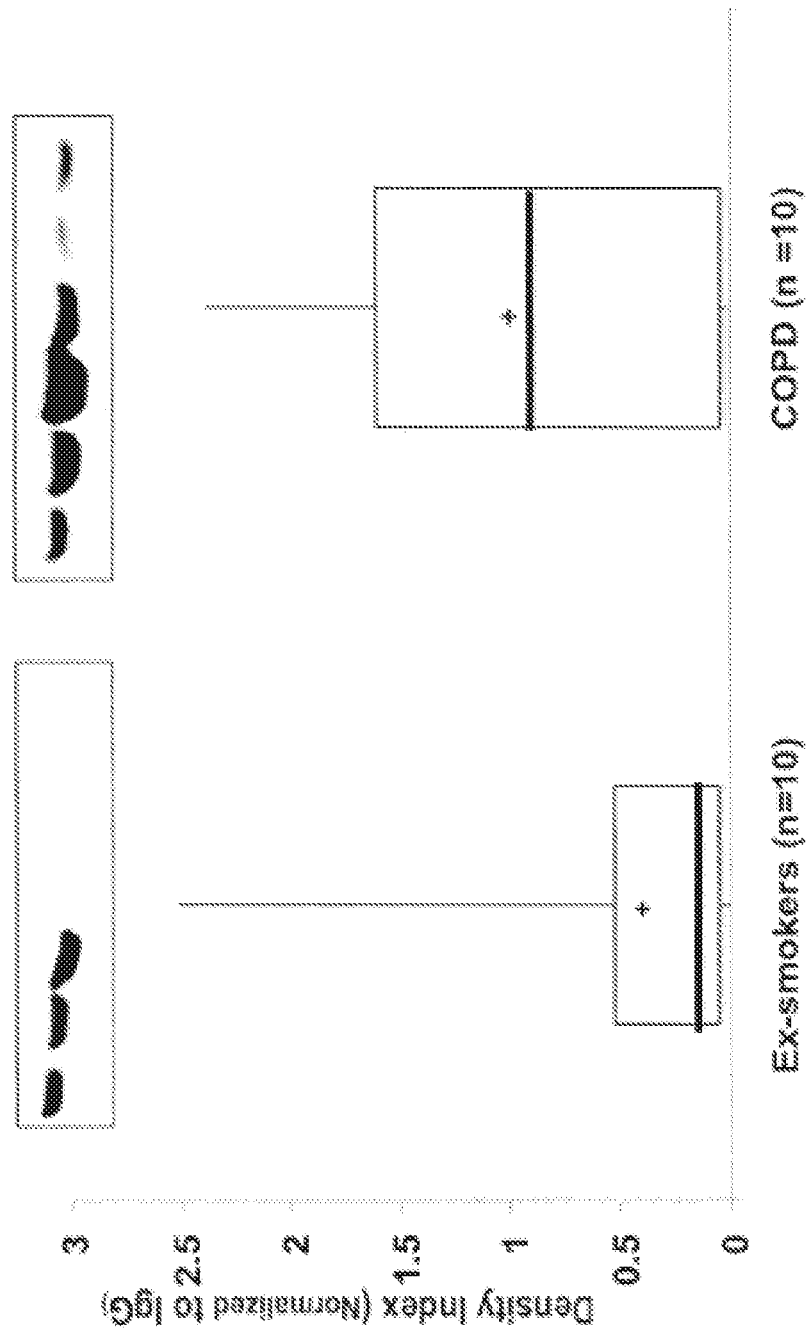
FIG. 4 depicts representative images of Western blots of plasma from GOLD 0 (left) and GOLD IV (right) subjects probed with an anti-HGFL antibody. Blots were quantitated using densitometry and normalized to IgG light chain. The quantitative data are plotted below the Western blot images as box plots, wherein the box represents the interquartile range.

Data for GRP78, IL1RAP and HGFL are depicted in FIGS. 2, 3, and 4, respectively. The data are presented as box plots. The first and third quartiles are the top and bottom edges of the box area, and defines a range of values known as the "interquartile range." The median for each data set is indicated by the center horizontal line in the box, and the mean is represented by a plus sign. The extreme values (with 1.5 times the interquartile range from the upper or lower quartile) are the ends of the lines extending from the interquartile range.

The box plots depicted in FIGS. 2, 3, and 4 exhibit little overlap of the data for GOLD IV with the data for GOLD 0. In particular, the interquartile range for GOLD IV shows virtually no overlap with the interquartile range for GOLD 0 for GRP78 and for IL1RAP. These data demonstrate the robustness of the method for identifying biomarkers distinguishing between subjects without COPD and subjects with very severe COPD. Without wishing to be bound by theory, it is believed that the robustness of the method stems in part from the very tightly matched subjects selected for the GOLD 0 and GOLD IV groups. It is further believed that this difference distinguishes these results from prior art methods and results. Moreover, these results support that each of these biomarkers can be used to assess susceptibility to COPD, assess disease severity, to monitor disease progression, and to monitor therapeutic efficacy.

2-DE gel separation was used to study pooled samples immunodepleted by the Qproteome depletion method. 2-DE gel separation represents a powerful way to examine different isoforms of the same protein and, hence, detect protein post-translational modifications. The "less immunodepleted" sample was used to assess potential differences in the highly abundant proteins that remained in the Qproteome sample.

Figure 5:
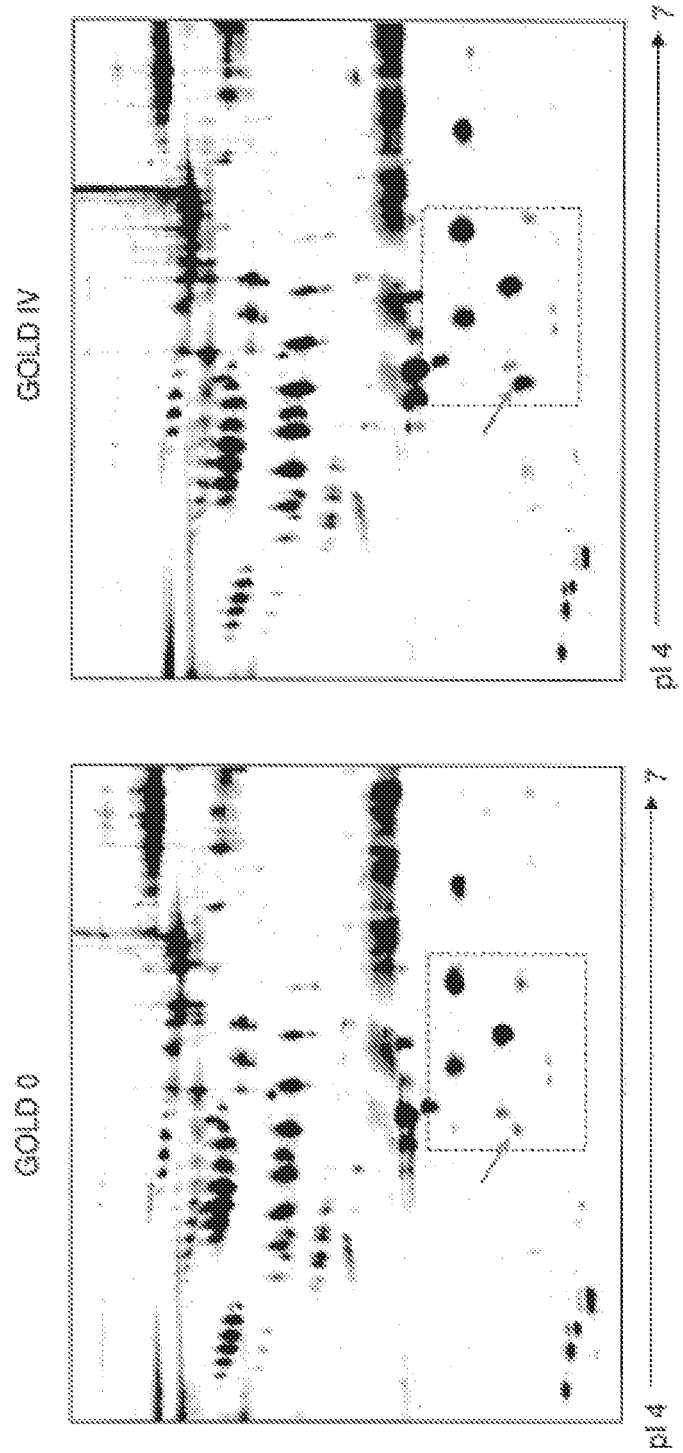
FIG. 5 depicts images of 2-DE gels of pooled protein extracts from GOLD 0 (left panel) and GOLD IV (right panel) subjects. The arrows point to three haptoglobin-alpha isoforms, one of which was found to be up-regulated in GOLD IV as compared to GOLD 0.

The 2-DE gel electrophoresis data demonstrated three haptoglobin-alpha isoforms with one of these being up-regulated. See FIG. 5. The up-regulated haptoglobin-alpha isoform was identified by mass spectroscopy as the type 2 isoform of haptoglobin-alpha (designated herein as "HPT2a"). Up-regulation of HPT2a□ observed in the pooled sample was confirmed in ten individual subjects from each of the two groups. See FIG. 6A. The amount of haptoglobin-alpha isoform 2 was 3.3 fold greater (mean) in GOLD IV than GOLD 0 (FIG. 6B; p<0.02). In addition, the interquartile range for GOLD IV shows virtually no overlap with the interquartile range for GOLD 0 for HPT2a. As for GeLC-MS, these data demonstrate the robustness of the 2-DE method using immunodepleted plasma for identifying biomarkers distinguishing between subjects without COPD and subjects with very severe COPD.

Mass spectroscopy evaluation of haptoglobin-alpha isoform 2 revealed several post-translation modifications present in the GOLD IV group that were not detected in the GOLD 0 group. These modifications are: acetylation of lysine 76, carbamidomethylation of cysteine 68, and methylation of the aspartic acids at positions 71 and 72 (numbering in SEQ ID No. 12). These post-translation modifications of haptoglobin-alpha isoform 2 are unique to the GOLD IV samples and therefore, can serve as an additional discriminating marker for assessing susceptibility for COPD in an at-risk subject and severity of COPD in a COPD patient. The use of post-translation modifications as disease markers is generally known in the art (see, for instance, Karsdal et al., 2008, Clin Biochem. 2010 July; 43 (10-11): 793-804. Epub 2010 Apr. 8).

Receiver operating characteristic ("ROC") curves are graphical depictions of true positive rate versus true negative rate, and are therefore useful for assessing the accuracy of predictions. The point at (0,1) in such curves is the perfect classification: 100% sensitivity (i.e., no false negatives) and 100% specificity (i.e., no false positives). Thus, ROC curves that approach (0,1) are desirable. Area under the curve, AUC, is a useful parameter for ROC curves. Predicters are expected to have an AUC >0.5. The larger the AUC for a biomarker, the better that biomarker is expected to be as a predicter.

Figure 7A:
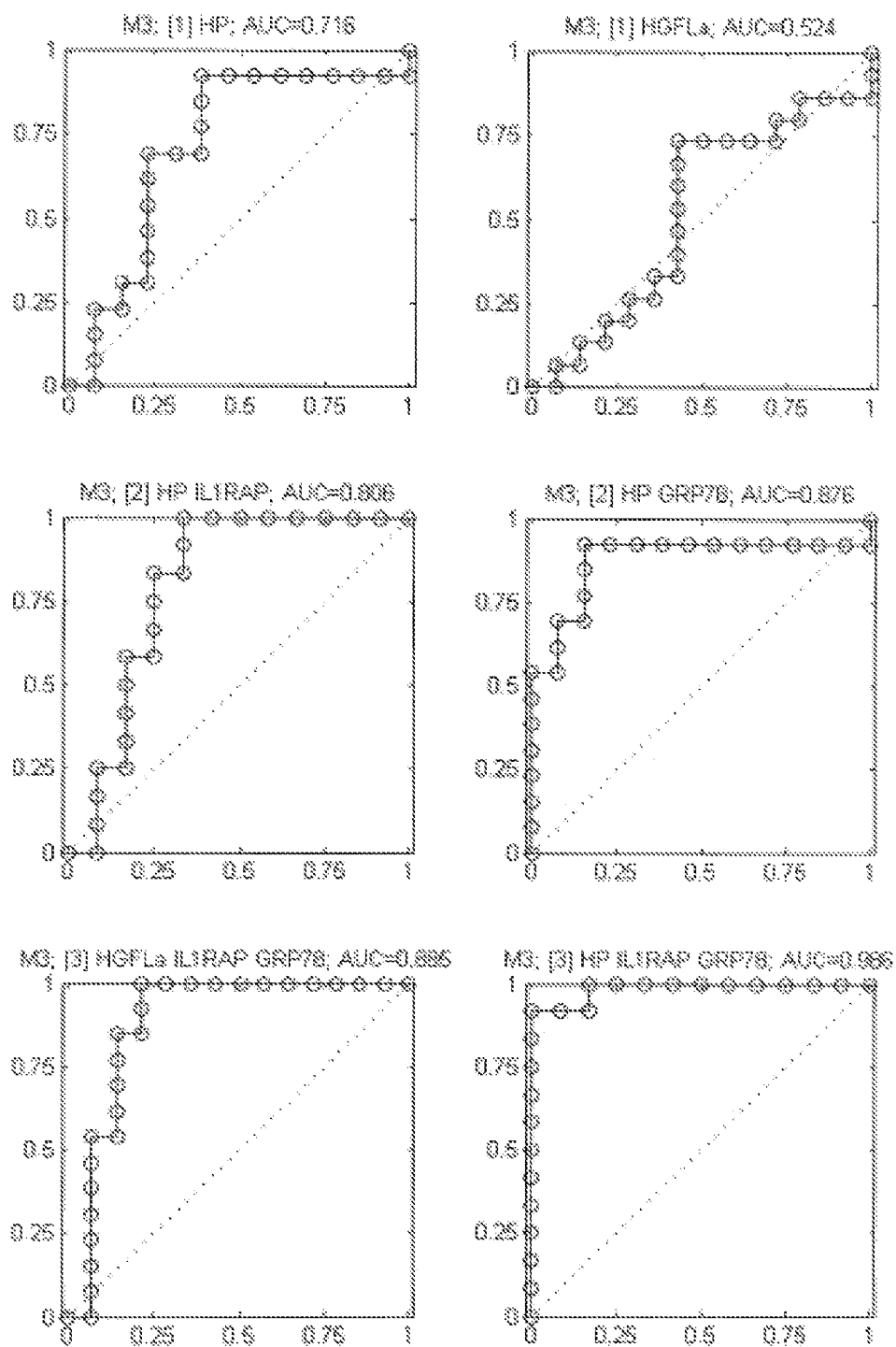
FIGS. 7A, 7B and 7C depict a series of receiver operating characteristic ("ROC") curves. ROC curves are shown for four individual biomarkers, and combinations of these biomarkers. The biomarkers are: HPT2a (labeled HP in the figure) GRP78, IL1RAP, and HGFL (labeled HGFLa in the figure). AUC=area under curve.
Figure 7B:
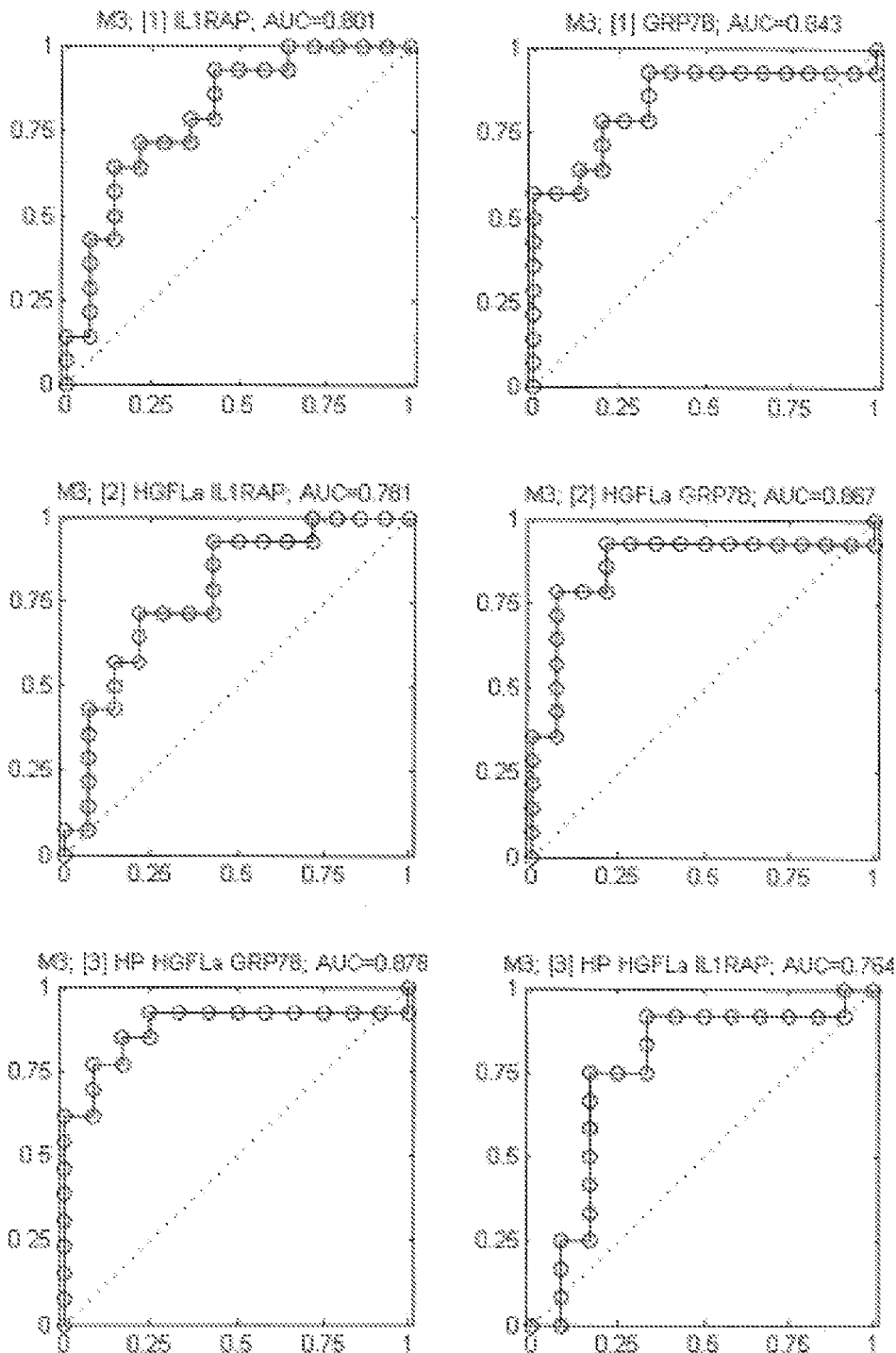
Figure 7C:
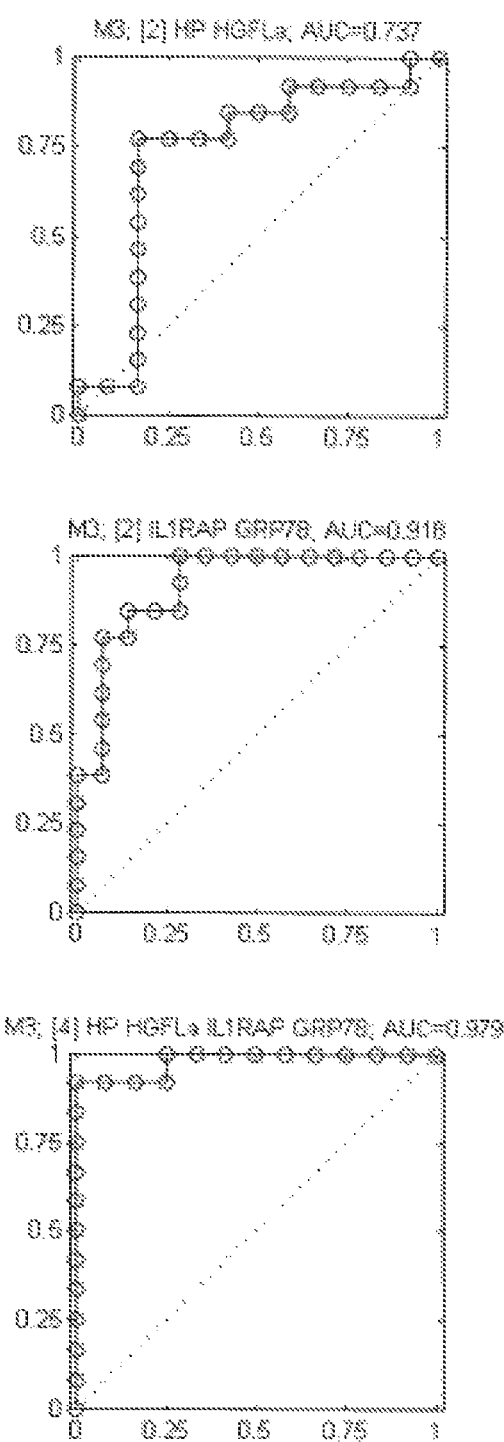

ROC curves were determined for four biomarkers individually and in combinations of two or three biomarker. The four biomarkers are: HPT, GRP78, IL1RAP and HGFL. The curves are depicted in FIGS. 7A, 7B and 7C. All four biomarkers have AUC values >0.5. Notably, the AUC value for GRP78 is 0.843 (FIG. 7B). In addition, combinations of two, three or all four of the biomarkers also all have AUC values >0.5. The following combinations have AUC values in excess of 0.8: HPT2a and IL1RAP (FIG. 7A); HPT2a and GRP78 (FIG. 7A); HGFL and GRP78 (FIG. 7B); HGFL, IL1RAP and GRP78 (FIG. 7A); HPT2a, HGFL and GRP78 (FIG. 7B); IL1RAP and GRP78 (FIG. 7C); HPT2a, IL1RAP, and GRP78 (FIG. 7A); and HPT2a, HGFL, IL1RAP, and GRP78 (FIG. 7C). Notably, the following combinations have AUC values in excess of 0.9: IL1RAP and GRP78; HPT2a, IL1RAP, and GRP78; and HPT2a, HGFL and IL1RAP, and GRP78.

Analysis was also performed to assess whether any of the identified biomarkers could predict the extent of $FEV_1$ impairment in COPD disease. $FEV_1$ is the maximal amount of air one can forcefully exhale in one second. The measure is converted to a percentage of normal ("$FEV_1$ (% predicted)") which is a measure of the degree of obstruction, as summarized in Table 10.

TABLE 10

| | |
|---|---|
| $FEV_1$ greater than 80% of predicted | Normal |
| $FEV_1$ 60% to 79% of predicted | Mild obstruction |
| $FEV_1$ 40% to 59% of predicted | Moderate obstruction |
| $FEV_1$ less than 40% of predicted | Severe obstruction |

The plasma concentration of three of the identified biomarkers, GRP78, sCD163 (which is C163A without its N-terminal signal sequence), and HGFL significantly correlated ($r \geq 0.28$; $p \leq 0.013$) with percent predicted $FEV_1$. See FIGS. 8A, 8B and 8D. In contrast, the plasma concentration of IL1RAP did not correlate significantly with FEV1. See FIG. 8C. Using multi-variate analysis, the combination of GRP78 and sCD163 was found to perform significantly better ($r=0.46$; $p=0.001$) than either one alone regarding percent predicted $FEV_1$.

The disclosures of each and every patent, patent application, and publication cited herein are hereby incorporated herein by reference in their entirety.

While the methods and kits have been disclosed with reference to specific embodiments, it is apparent that other embodiments and variations may be devised by others skilled in the art without departing from the true spirit and scope of the described methods and kits. The appended claims are intended to be construed to include all such embodiments and equivalent variations.

TABLE 11

| Seq ID No. | Protein Name | Protein ID | SwissProt Accession No. | Sequence Header info |
|---|---|---|---|---|
| 1 | Lethal (3) malignant brain tumor-like 3 protein | LMBL3 | Q96JM7 | OS = *Homo sapiens* <br> GN = L3MBTL3 <br> PE = 1 <br> SV = 2 |
| 2 | Cathelicidin antimicrobial peptide | CAMP | P49913 | OS = *Homo sapiens* <br> GN = CAMP <br> PE = 1 <br> SV = 1 |
| 3 | Contactin-1 | CNTN1 | Q12860 | sp\|Q12860\|CNTN1_HUMAN Contactin-1 <br> OS = *Homo sapiens* <br> GN = CNTN1 <br> PE = 1 <br> SV = 1 |
| 4 | Vascular cell adhesion protein 1 | VCAM1 | P19320 | OS = *Homo sapiens* <br> GN = VCAM1 <br> PE = 1 <br> SV = 1 |
| 5 | Interleukin-1 receptor accessory protein | IL1RAP | Q9NPH3 | OS = *Homo sapiens* <br> GN = IL1RAP <br> PE = 1 <br> SV = 2 |
| 6 | Dermcidin | DCD | P81605 | OS = *Homo sapiens* <br> GN = DCD <br> PE = 1 <br> SV = 2 |
| 7 | Vitamin K-dependent protein Z | PROZ | P22891 | OS = *Homo sapiens* <br> GN = PROZ <br> PE = 1 <br> SV = 2 |
| 8 | Hepatocyte growth factor-like | HGFL | P26927 | OS = *Homo sapiens* <br> GN = MST1 <br> PE = 1 <br> SV = 2 |
| 9 | Cell surface glycoprotein | MUC18 | P43121 | OS = *Homo sapiens* <br> GN = MCAM <br> PE = 1 <br> SV = 2 |
| 10 | 79 kDa glucose-regulated protein | GRP78 | P11021 | OS = *Homo sapiens* <br> GN = HSPA5 <br> PE = 1 <br> SV = 2 |
| 11 | Coagulation factor V | FA5 | P12259 | OS = *Homo sapiens* <br> GN = F5 <br> PE = 1 <br> SV = 4 |
| 12 | Haptoglobin-alpha isoform 2 | HPT2a† | P00738 | Residues 19-160 of P00738.1 (SEQ ID NO: 31) |
| 13 | Scavenger receptor cysteine-rich type 1 protein M130 | C163A | Q86VB7 | OS = *Homo sapiens* <br> GN = CD163 <br> PE = 1 <br> SV = 2 |
| 14 | Neural cell adhesion molecule | NCAM1 | P13591 | OS = *Homo sapiens* <br> GN = NCAM1 <br> PE = 1 <br> SV = 3 |
| 15 | Proteoglycan 4 | PRG4 | Q92954 | OS = *Homo sapiens* <br> GN = PRG4 <br> PE = 1 <br> SV = 2 |

TABLE 11-continued

| Seq ID No. | Protein Name | Protein ID | SwissProt Accession No. | Sequence Header info |
|---|---|---|---|---|
| 16 | Procollagen C-endopeptidase enhancer 1 | PCOC1 | Q15133 | OS = *Homo sapiens*<br>GN = PCOLCE<br>PE = 1<br>SV = 2 |
| 17 | Plastin-2 OS *Homo sapiens* | PLSL | P13796 | OS = *Homo sapiens*<br>GN = LCP1<br>PE = 1<br>SV = 6 |
| 18 | Coagulation factor XIII A chain | F13A | P00488 | OS = *Homo sapiens*<br>GN = F13A1<br>PE = 1<br>SV = 4 |
| 19 | Fetuin-B | FETUB | Q9UGM5 | OS = *Homo sapiens*<br>GN = FETUB<br>PE = 1<br>SV = 2 |
| 20 | Protein S100-A6 | S10A | P06703 | OS = *Homo sapiens*<br>GN = S100A6<br>PE = 1<br>SV = 1 |
| 21 | Metalloproteinase inhibitor 2 | TIMP2 | P16035 | OS = *Homo sapiens*<br>GN = TIMP2<br>PE = 1<br>SV = 2 |
| 22 | Peroxiredoxin-1 | PRDX1 | Q06830 | OS = *Homo sapiens*<br>GN = PRDX1<br>PE = 1<br>SV = 1 |
| 23 | Macrophage colony-stimulating factor 1 receptor | CSF1R | P07333 | OS = *Homo sapiens*<br>GN = CSF1R<br>PE = 1<br>SV = 2 |
| 24 | Probable G protein coupled receptor 25 | GPR25 | O00155 | OS = *Homo sapiens*<br>GN = GPR25<br>PE = 2<br>SV = 2 |
| 25 | Putative zinc-alpha-2-glycoprotein-like 1 | ZAGL1 | A8MT79 | OS = *Homo sapiens*<br>PE = 5<br>SV = 2 |
| 26 | HLA class I histocompatibility antigen, B-15 alpha chain | 1B15 | P30464 | OS = *Homo sapiens*<br>GN = HLA-B<br>PE = 1<br>SV = 2 |
| 27 | Mannosyl-oligosaccharide1,2-alpha-mannosidase IA | MA1A1 | P33908 | OS = *Homo sapiens*<br>GN = MAN1A1<br>PE = 1<br>SV = 3 |
| 28 | Myelin P2 | MYP2 | P02689 | OS = *Homo sapiens*<br>GN = PMP2<br>PE = 1<br>SV = 3 |
| 29 | Metalloproteinase inhibitor 1 | TIMP1 | P01033 | OS = *Homo sapiens*<br>GN = TIMP1<br>PE = 1<br>SV = 1 |
| 30 | HLA class I histocompatibility antigen, A-1 alpha chain | 1A01 | P30443 | OS = *Homo sapiens*<br>GN = HLA-A<br>PE = 1<br>SV = 1 |
| 31 | Haptoglobin-alpha isoform 2 preproprotein | HPT2 | P00738 | Signal sequence: residues 1-18<br>Haptoglobin alpha: residues 19-160<br>Haptoglobin beta: residues 162-406 |
| 32 | Haptoglobin-alpha isoform 2 having a post-translational modification | HPT2a-PTM | n/a | Peptide sequence within SEQ ID No. 12 in which post-translational modifications (PTMs) uniquely present in GOLD IV subjects; PTMs are:<br>C1 = carbamidomethylation;<br>D4 = methylation;<br>D5 = methylation;<br>K9 = acetylation |

What is claimed is:

1. A method of treating chronic obstructive pulmonary disease (COPD) in a subject in need of such treatment, the method comprising:
   (a) measuring the level of at least 79 kDa glucose-regulated protein (GRP78) in a biological fluid test sample selected from peripheral whole blood, serum or plasma from a subject at risk for developing COPD;
   (b) comparing the level of GRP78 in the test sample with the level of GRP78 in a normal reference sample;
   (c) diagnosing the subject as having COPD upon detecting an elevated level of GRP78 in the test sample as compared to the level of GRP78 in the reference sample; and
   (d) administering a treatment to the diagnosed subject comprising one or more pharmaceutical agents that promote the expression of GRP78 in lung tissue.

2. The method according to claim 1 wherein the biological fluid sample is serum or plasma.

3. The method according to claim 1 wherein the reference sample is from an individual that does not manifest clinical symptoms of COPD.

4. The method according to claim 1 wherein the pharmaceutical agent is tunicamycin.

5. The method according to claim 1 wherein the pharmaceutical agent is thapsigargin.

6. A method of treating COPD comprising:
   administering a COPD treatment to a subject diagnosed with COPD on the basis that an elevated level of 79 kDa glucose-regulated protein (GRP78) is detected in a biological fluid obtained from the subject, as compared to the level of GRP78 in a normal reference, thereby diagnosing the subject with COPD, said sample selected from peripheral whole blood, serum or plasma from the subject, and said COPD treatment comprising one or more pharmaceutical agents that promote the expression of GRP78 in lung tissue.

7. The method according to claim 6 wherein the biological fluid test sample is serum or plasma.

8. The method according to claim 6 wherein the reference sample is from an individual that does not manifest clinical symptoms of COPD.

9. The method according to claim 6 wherein the pharmaceutical agent is tunicamycin.

10. The method according to claim 6 wherein the pharmaceutical agent is thapsigargin.

* * * * *

UNITED STATES PATENT AND TRADEMARK OFFICE
CERTIFICATE OF CORRECTION

PATENT NO. : 10,471,086 B2
APPLICATION NO. : 15/081073
DATED : November 14, 2017
INVENTOR(S) : Salim Merali, Steven G. Kelsen and Carlos A. Barrero Page 1 of 1

It is certified that error appears in the above-identified patent and that said Letters Patent is hereby corrected as shown below:

In the Specification

In Column 1, under the "Reference to Government Grant", please replace the text on Lines 17-20 with the following:
-- The invention was made with government support under HL101713 awarded by the National Institutes of Health. The government has certain rights in this invention. --

Signed and Sealed this
Twenty-first Day of November, 2023

Katherine Kelly Vidal
*Director of the United States Patent and Trademark Office*